United States Patent
Reeder et al.

(10) Patent No.: US 9,918,997 B2
(45) Date of Patent: Mar. 20, 2018

(54) COMPOSITIONS AND METHODS FOR THE TREATMENT OF NEURODEGENERATIVE AND OTHER DISEASES

(71) Applicants: Thaddeus Cromwell Reeder, San Carlos, CA (US); Mark Wade Moore, Greenbrae, CA (US); Douglas Alan Lorenz, Bend, OR (US); David Keith Lyon, Bend, OR (US)

(72) Inventors: Thaddeus Cromwell Reeder, San Carlos, CA (US); Mark Wade Moore, Greenbrae, CA (US); Douglas Alan Lorenz, Bend, OR (US); David Keith Lyon, Bend, OR (US)

(73) Assignee: GLIALOGIX, INC., San Anselmo, CA (US)

( * ) Notice: Subject to any disclaimer, the term of this patent is extended or adjusted under 35 U.S.C. 154(b) by 80 days.

(21) Appl. No.: 15/430,294

(22) Filed: Feb. 10, 2017

(65) Prior Publication Data

US 2017/0165279 A1 Jun. 15, 2017

Related U.S. Application Data

(63) Continuation of application No. 15/365,843, filed on Nov. 30, 2016, which is a continuation of application No. 14/170,405, filed on Jan. 31, 2014, now Pat. No. 9,597,339.

(60) Provisional application No. 61/780,340, filed on Mar. 13, 2013, provisional application No. 61/759,933, filed on Feb. 1, 2013.

(51) Int. Cl.
  *A61K 31/635* (2006.01)
  *A61K 47/32* (2006.01)
  *A61K 9/16* (2006.01)
  *A61K 9/00* (2006.01)

(52) U.S. Cl.
  CPC .......... *A61K 31/635* (2013.01); *A61K 9/0053* (2013.01); *A61K 9/1635* (2013.01); *A61K 47/32* (2013.01)

(58) Field of Classification Search
  CPC ............................ A61K 31/635; A61K 47/32
  See application file for complete search history.

(56) References Cited

U.S. PATENT DOCUMENTS 2,396,145 A   3/1946  Askelof et al.
6,521,640 B1  2/2003  Gwag et al.
(Continued)

FOREIGN PATENT DOCUMENTS

WO   WO1998/020864     5/1998
WO   WO2001072308 A1  10/2001
(Continued)

OTHER PUBLICATIONS

Compston et al., Multiple Sclerosis, Lancet 2008; 372:1502-17.
(Continued)

*Primary Examiner* — San-Ming Hui
(74) *Attorney, Agent, or Firm* — Sam L. Nguyen; Hamilton DeSanctis & Cha, LLP

(57) ABSTRACT

In one embodiment, the present application discloses methods of treating diseases and disorders with sulfasalazine and pharmaceutical formulations of sulfasalazine where the bioavailability of the sulfasalazine is increased. In another embodiment, the present application also provides dosing regimens for treating neurodegenerative diseases and disorders with compositions comprising sulfasalazine.

11 Claims, 9 Drawing Sheets

(56) References Cited

U.S. PATENT DOCUMENTS

| | | | |
|---|---|---|---|
| 7,964,585 | B2 | 6/2011 | Berti-Mattera et al. |
| 2003/0186950 | A1 | 10/2003 | Gout |
| 2006/0045865 | A1 | 3/2006 | Jacob et al. |
| 2007/0053869 | A1 | 3/2007 | Sugiyama |
| 2008/0069878 | A1 | 3/2008 | Venkatesh et al. |
| 2013/0202659 | A1 | 8/2013 | Crawford et al. |
| 2015/0182457 | A1 | 7/2015 | Huang et al. |

FOREIGN PATENT DOCUMENTS

| | | |
|---|---|---|
| WO | WO2006/049957 | 5/2006 |
| WO | WO2007088034 A2 | 8/2007 |
| WO | WO2009108077 A2 | 9/2009 |
| WO | WO2010033587 A2 | 3/2010 |

OTHER PUBLICATIONS

Trapp et al., Multiple Sclerosis: An Immune or Neurodegenerative Disorder?, Annu. Rev. Neurosci. 2008; 31:247-69.
Kremenchutzky et al., The natural history of multiple sclerosis: a geographically based study 9: Observations on the progressive phase of the disease, Brain 2006; 129: 584-594.
Lassman et al., Progressive multiple sclerosis: pathology and pathogenesis, 2012, Nat. Rev. Neurol. 2012; 8:647-656.
Stys et al., Will the real multiple sclerosis please stand up?, Nat. Rev. Neurosc. 2012; 13:507-514.
Fox et al., Setting a research agenda for progressive multiple sclerosis: The International Collaborative on Progressive MS, Multiple Sclerosis Journal 2012; 18(11):1534-15.
Fitzner et al., Chronic Progressive Multiple Sclerosis-Pathogenesis of Neurodegeneration and Therapeutic Strategies, Current Neuropharmacology 2010; 8:305-315.
Weiner et al., A shift from adaptive to innate immunity: a potential mechanism of disease progression in multiple sclerosis, J. Neurol. 2008; 255[Suppl 1]:3-11.
Burns et al., Mitoxantrone repression of astrocyte activation: Relevance to multiple sclerosis, Brain Res. 2012; 1473:236-241.
Frigo et al., Glutamate and Multiple Sclerosis, Current Medicinal Chemistry 2012; 19:1295-1299.
Matute et al., Glutamate and ATP signalling in white matter pathology, J. Anat. (2011).
Sarchielli et al., Excitatory amino acids and multiple sclerosis, Arch. Neurol. 2003; 60:1082-1088.
Eriksson et al., Epileptic seizure, cranial neurolgias and paroxysmal symptoms in remitting and progressive multiple sclerosis, Multiple Sclerosis (2002) 8, 495-499.
Svendsen et al., Sensory function and quality of life in patients with multiple sclerosis and pain, Pain 2005; 114:473-481.
Bogaert et al., Amyotrophic Lateral Sclerosis and Excitotoxicity: From Pathological Mechanism to Therapeutic Target, CNS & Neurol. Disorders—Drug Targets 2010; 9:297-304.
Philips et al., Neuroinflammation in amyotrophic lateral sclerosis: role of glial activation in motor neuron disease, Lancet Neurol. 2011; 10:253-63.
Ilieva et al., Non-cell autonomous toxicity in neurodegenerative disorders: ALS and beyond, J. Cell Biol. vol. 187, No. 6, 761-772.
Jin et al., The Interaction of the Neuroprotective Compounds Riluzole and Phenobarbital with AMPA-Type Glutamate Receptors: A Patch-Clamp Study, Pharmacology, 2010; 85: 54-62.
Baron et al., Neuropathic pain: diagnosis, pathophysiological mechanisms, and treatment, Lancet Neurol. 2010; 9:807-19.
Berti-Mattera et al., Sulfasalazine Blocks the Development of Tactile Allodynia in Diabetic Rats, Diabetes 2008, 57:2801-2808.
Ungard et al., Inhibition of breast cancer-cell glutamate release with sulfasalazine limits cancer-induced bone pain, Pain 2014; 155:28-36.
Weaver et al., Improved Gastrointestinal Tolerance and Patient Preference of Enteric Uncoated Sulfasalazrne Tablets in Patients with RA, J.Clin. Rheumat. 1999; 5:193-200.
Peppercorn et al., Sulfasalazine and Related New Drugs, J.Clin. Pharmacol. 1987; 27:260-265.
Watkinson et al., Sulphasalazine: A Review of 40 Years' Experience, Drugs 1986; 32 (Suppl.1):1-11.
Noseworthy et al., The Mayo Clinic-Canadian cooperative trial of sulfasalazine in active multiple sclerosis, Neurol. 1998; 51:1342-1352.
Khan et al., Optimum dose of sulphasalazine for maintenance treatment in ulcerative colitis, Gut, 1980; 21:232-240.
Yamasaki et al., Pharmacogenetic Characterization of Sulfasalazine Disposition Based on NAT2 and ABCG2 (BCRP) Gene Polymorphisms . . . , Clin. Pharmac.&Thera. 2007; 84 (1):95-103.
De Jong et al., ABCG2 Pharmacogenetics : Ethnic Differences in Allele Frequency and Assessment of Influence on Irinotecan Disposition, Clin. Cancer Res. 2004;10:5889 5894.
Buckingham et al., Glutamate release by primary brain tumors induces epileptic activity, Nat. Medicine 2011, Advanced Online Publication.
Gurney et al., Motor Neuron Degeneration in Mice That Express a Human Cu,Zn Superoxide Dismutase Mutation, Science 1994; 264:1772-1774.
Scott et al., Design, power, and interpretation of studies in the standard murine model of ALS, Amyotrophic Lateral Sclerosis. 2008; 9:4-15.
Shin, AAD-2004, a potent spin trapping molecule and microsomal prostaglandin E synthase—1 inhibitor, shows safety and efficacy in a mouse model of ALS, J. Neurochem. 2012.
Lincecum et al., From transcriptome analysis to therapeutic anti-CD40L treatment in the SOD1model of amyotrophic lateral sclerosis, Nat. Genetics 2010; 42(5):392-400.
Zaher et al., Breast Cancer Resistance Protein (Bcrp/abcg2) Is a Major Determinant of Sulfasalazine Absorption and Elimination in the Mouse, Mol Pharmaceutics 2005; 3(1)55: 61.
Pfizer, Azulfidine EN-tabs sulfasalazine delayed release tablets, USP, 2013.
Pfizer, Azulfidine sulfasalazine tablets, USP, 2009.
Albrecht, Mechanisms of Oxidative Glutamate Toxicity: The Glutamate/Cystine Antiporter System Xc as a Neuroprotective . . . ,CNS & Neurol. Disord.-Drug Targets 2010; 9: 373-382.
Barger, Activation of microglia by secreted amyloid precursor protein evokes release of glutamate by cystine exchange and attenuates . . . , J of Neurochem 2001; 76:846-854.
Bridges, System Xc-cystine/glutamate antiporter: an update on molecular pharmacology and roles within the CNS, Brit. J of Pharmacol 2012; 165:20-34.
Correale, Sulfasalazine aggravates experimental autoimmune encephalomyelitis and causes an increase in the number of autoreactive T cells ,J of Neuroimmol 1991; 34:109-120.
Costigan, Analgesia by inhibiting tetrahydobiopterin synthesis, Curr Opin Pharmacol. 2012; 12(1):92 - 99.
Dahan, Small intestinal efflux mediated by MRP2 and Bcrp shifts sulfasalazine intestinal permeability from high . . . , Am J Physiol Gastrointest Liver Physiol 2009; 297:G371-G377.
DAS, Solid Dispersions : An Approach to Enhance the Bioavailability of Poorly Water-Soluble Drugs, Int. J of Pharmacol and Pharmaceut Tech. ISSN: 2277-3436; 1(1): 37-46.
Domercq, System Xc and Glutamate Transporter Inhibition Mediates Microglial Toxicity to Oligodendrocytes, J Immunol 2007;178:6549-6556.
Kurose, Population Differences in . . . ,Drug Metab. Pharmacokinet. 2012; 27(1):9-54.
Lasiene, Glial Cells inAmyotrophic Lateral Sclerosis, Neurol Res Intl 2011; vol. 2011, Article ID 718987.
Lewerenz, The Cystine/Glutamate Antiporter System Xc-in Health and Disease: . . . ,Antioxi.&Redox Signal. 2013; 18(5):522-555.
Lo, The xc Cystine/Glutamate Antiporter: A Potential Target for Therapy of Cancer and Other Diseases, J. Cell. Physiol. 2008; 215:593-602.
Massie, Dopaminergic neurons of system xc-deficient mice are highly protected, The FASEB Journal 2011; 25:1-11.
Pampliega, Increased expression of cystine/glutamate antiporter in multiple sclerosis, J of Neuroinflam. 2011; 8:63.

(56) References Cited

OTHER PUBLICATIONS

Duarte, Overcoming poor bioavailability through amorphous solid dispersions, Indus. Pharmacy 2011; 30:4-6.
Uitdehaag, Failure of sulfasalazine to influence autoimmune encephalomyelitis, Acta Neurol Scand 1991, 173.
Urquhart, Breast cancer resistance protein (ABCG2) and drug disposition: . . . , Pharmacogenetics and Genomics 2008, 18:439-44.
Zajicek, Diagnosis and disease modifying treatments in multiple sclerosis, Postgrad Med J 2005;81:556-561.

A. xCT levels in day 85 cervical region

B. xCT levels in day 85 lumbar region

C. xCT levels in day 100 cervical region

D. xCT levels in day 100 lumbar region

COMPOSITIONS AND METHODS FOR THE TREATMENT OF NEURODEGENERATIVE AND OTHER DISEASES

This application is a continuation of application Ser. No. 15/365,843 filed Nov. 30, 2016 which is a continuation of application Ser. No. 14/170,405 filed Jan. 31, 2014 which claims the benefit of U.S. Provisional Application No. 61/759,933 filed Feb. 1, 2013, and U.S. Provisional Application No. 61/780,340 filed Mar. 13, 2013, all of which are incorporated herein by reference.

FIELD OF THE INVENTION

In one embodiment, the present invention relates to methods of treating diseases and disorders with sulfasalazine and pharmaceutical formulations of sulfasalazine where the bioavailability of the sulfasalazine is increased. In another embodiment, the present invention also provides dosing regimens for treating neurodegenerative diseases or disorders, such as P-MS and ALS with compositions comprising sulfasalazine.

BACKGROUND OF THE INVENTION

Neurodegenerative diseases are collectively a leading cause of death and disability. Examples of neurodegenerative diseases include progressive multiple sclerosis, amyotrophic lateral sclerosis, Alzheimer's disease, Parkinson's disease, epilepsy, neuropathic pain, Huntington's disease and traumatic brain injury. While the ultimate causes and natural histories of the individual neurodegenerative diseases differ, common pathological processes occur in most, if not all, neurodegenerative diseases. These common pathological processes include high levels of activated glial cells ("neuroinflammation"), dysregulated glutamate signaling and chronic damage to axons and neurons.

Progressive multiple sclerosis (P-MS) is a devastating neurodegenerative disease that affects approximately 120,000 people in the United States and 350,000 people in the developed world. P-MS patients progressively accumulate disabilities, including changes in sensation (hypoesthesia), muscle weakness, abnormal muscle spasms, or difficulty moving; difficulties with coordination and balance; problems in speech (dysarthria) or swallowing (dysphagia); visual problems (nystagmus, optic neuritis, phosphenes or diplopia), fatigue and acute or chronic pain syndromes, bladder and bowel difficulties, cognitive impairment, or emotional symptomatology (mainly major depression). The only drug currently approved to treat P-MS in the United States is mitoxantrone (Novantrone), a cytotoxic agent that is also used to treat cancers. Mitoxantrone has a serious adverse effect profile and carries a lifetime limit on exposure. The treatment of P-MS remains a significant unmet medical need.

There are three major sub-types of P-MS recognized by the National Multiple Sclerosis Society (US): Primary Progressive Multiple Sclerosis (PP-MS), Secondary Progressive Multiple Sclerosis (SP-MS) and Progressive-Relapsing Multiple Sclerosis (PR-MS). Approximately 85% of multiple sclerosis patients clinically present with Relapse Remitting Multiple Sclerosis (RR-MS), characterized by episodes of acute neurological deficits (relapses), followed by partial or complete recovery of the deficits. After a median time to conversion of around 19 years, approximately 70% of RR-MS patients develop a progressive neurological decline, clinically recognized as SP-MS. Approximately 10% of multiple sclerosis patients clinically present with PP-MS, characterized by a progressive neurological decline with few to no preceding episodes of neurological deficits (relapses), while 5% present with PR-MS, characterized by a steady worsening disease from the onset but also have clear acute flare-ups (relapses), with or without recovery, e.g. Compton et al, *Lancet* 372:1502-1517 (2008); Trapp et al, *Annu. Rev. Neurosci.* 31:247-269 (2008). Here, PP-MS, SP-MS and PR-MS are grouped together as P-MS, as they share many similarities, including natural history, clinical manifestations and pathology, e.g. Kremenchutsky et al, *Brain* 129:584-594 (2006); Lassmann et al, *Nat. Rev. Neurology* 8:647-656 (2012); Stys et al, *Nat. Rev. Neuroscience* 13:507-514 (2012).

Thus far, drugs that are effective for RR-MS have not shown efficacy in P-MS, e.g. Fox et al, *Multiple Sclerosis Journal* 18:1534-1540 (2012). This is believed to be due to current RR-MS drugs primarily targeting the peripheral immune system (B and T-cells) while P-MS is instead driven by resident CNS inflammatory cells, including microglia and astrocytes, e.g. Fitzner et al, *Curr. Neuropharmacology* 8:305-315 (2008); Weiner, J. *Neurology* 255, Suppl. 1:3-11 (2008); Lassman *Neurology* 8:647-656 (2012). Recent evidence suggests that the efficacy of mitoxantrone in P-MS may be due to inhibition of activation of astrocytes, thereby linking anti-neuroinflammation with efficacy in P-MS, e.g. Burns et al, *Brain Res.* 1473: 236-241 (2012).

In addition to resident CNS neuroinflammation, P-MS is also accompanied by the loss of axons and ultimately death of neuronal cells. The mechanisms that drive axonal and neuronal damage are not completely understood, although glutamate excitotoxicity is one of the leading suspects in human P-MS, e.g. Frigo, *Curr. Medicin. Chem.* 19:1295-1299 (2012). In particular, oligodendrocytes are especially sensitive to elevated levels of glutamate, e.g. Matute, *J. Anatomy* 219:53-64 (2011). Subsets of MS patients have been demonstrated to have elevated extracellular glutamate levels in the cerebrospinal fluid, e.g. Sarchielli et al, *Arch. Neurol.* 60:1082-1088 (2003) and P-MS patients have an increased incidence of seizures and neuropathic pain; both conditions may derive from excessive glutamate signaling and are treated clinically with anti-glutamatergics, e.g. Eriksson et al, *Mult. Scler.* 8:495-499 (2002); Svendsen et al, *Pain* 114: 473-481 (2004).

Another neurodegenerative disease thought to involve excessive glutamatergic signaling is amyotrophic lateral sclerosis (ALS), which affects approximately 100,000 patients in the developed world. ALS patients progressively lose motor neuron function, causing muscular atrophy, paralysis and death. The average lifespan after diagnosis is only 3-5 years. Riluzole (Rilutek) is the only known treatment that has been found to improve survival in ALS patients; however, the treatment is effective only to a modest extent by lengthening the survival time by only several months. Thus treatment of ALS remains a significant unmet medical need.

At the molecular level, ALS is characterized by excessive glutamatergic signaling leading to neuroexcitotoxicity and motor neuron death; see, e.g. Bogaert et al, *CNS Neurol. Disord. Drug Targets* 9:297-304 (2010). Affected tissues in the spinal cord also have high levels of activated microglia and activated astrocytes, collectively recognized as neuroinflammation; see, e.g. Philips et al, *Lancet Neurol.* 10:253-263 (2011) and neuroinflammatory cells have been shown to drive disease progression in ALS animal models; see, e.g. Ilieva et al, *J. Cell Biol.* 187: 761-772 (2009). The glutamate pathway has been clinically validated in ALS, as Riluzole inhibits multiple glutamate activities, including the activity of AMPA glutamate receptor; see, e.g., Lin et al, *Pharmacology* 85:54-62 (2010).

Approximately 10% of ALS cases are familial, while the remainders are believed to be sporadic, with no clear genetic cause to date. Among the familial cases, approximately 20% are due to mutations in the SOD1 gene. Mice and rats genetically altered to contain the mutant human SOD1 gene develop motor neuron disease that phenotypically resembles human ALS. Because of this, most potential ALS therapies are tested in the SOD1 mouse or rat model for efficacy.

Excessive glutamatergic signaling is believed to play a causal role in neurodegenerative diseases besides P-MS and ALS. For instance, neuropathic pain is a chronic condition caused by damage or disease that affects the somatosensory system. Neuropathic pain is associated with neuronal hyperexcitability, a common consequence of excessive glutamate signaling, see, e.g. Baron et al, Lancet Neurology 9: 807-819 (2010). Neuropathic pain may manifestin abnormal sensations called dysesthesia and pain produced by normally non-painful stimuli (allodynia). Neuropathic pain may have continuous and/or episodic (paroxysmal) components. The latter are likened to an electric shock. Common qualities include burning or coldness, "pins and needles" sensations, numbness and itching. Neuropathic pain is clinically treated with compounds that possess anti-glutamatergic activity (e.g. Topamax, Pregabalin). Importantly, sulfasalazine has previously been shown to have efficacy in models of diabetic neuropathy (e.g. Berti-Mattera et al, *Diabetes* 57: 2801-2808 (2008); U.S. Pat. No. 7,964,585) and cancer-induced bone pain (e.g. Ungard et al, *Pain* 155: 28-36 (2014)), and is currently being evaluated in clinical trials of painful diabetic neuropathy (see Massachusetts General Hospital, Clinical Trials Identifier NCT01667029).

Other neurodegenerative diseases where compounds with anti-glutamatergic activity are used clinically include Parkinson's disease (Amantadine and Budipine), Alzheimer's disease (Memantine), and epilepsy (Carbamazepine, Lamictal, and Keppra). Anti-glutamatergics are being investigated for treatment of traumatic brain injury, Huntington's disease, multiple sclerosis, and ischemic stroke. In many cases, these neurological diseases are also accompanied by high levels of neuroinflammation. Other neurological diseases that are linked to excessive glutamate signaling and neuroinflammation include Rett Syndrome, Frontotemporal Dementia, HIV-associated Dementia, Tuberous Sclerosis and Alexander disease.

The system $x_c^-$ glutamate-cysteine exchange transporter (herein "system $x_c^-$") is the only glutamate transporter that normally functions to release glutamate into the extracellular space. The amount of glutamate released by system $x_c^-$ is sufficient to stimulate multiple ionotropic and metabotropic glutamate receptors in vivo. Current anti-glutamatergics target either the vesicular release of glutamate or individual glutamate receptors that lie downstream of glutamate release (e.g., riluzole to the AMPA receptor). In contrast, system $x_c^-$ is responsible for the non-vesicular release of glutamate and lies upstream of the individual glutamate receptors. The protein xCT (SLC7A11) is the only currently identified catalytic component of system $x_c^-$.

Sulfasalazine (also referred to as 2-hydroxy-5-[(E)-2-{4-[(pyridin-2-yl) sulfamoyl] phenyl}diazen-1-yl]benzoic acid, 5-([p(2-pyridylsulfamoyl) phenyl]azo) salicylic acid or salicylazosulfapyridine) is a conjugate of 5-aminosalicylate and sulfapyridine, and is widely prescribed for inflammatory bowel disease, rheumatoid arthritis, and ankylosing spondylitis. Sulfasalazine is degraded by intestinal bacteria into its metabolites, 5-aminosalicylate and sulfapyridine. The mechanism of action in inflammatory bowel disease and rheumatoid arthritis is unknown, although action in the colon may be mediated by a metabolite, 5-aminosalicylate. Sulfasalazine has been shown to be an inhibitor of system $x_c^-$.

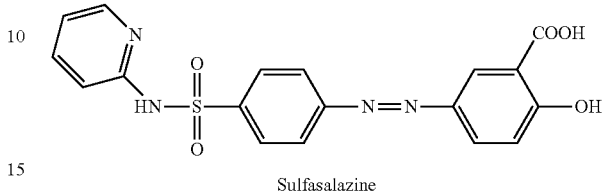

Sulfasalazine

The current U.S. on-market formulations of sulfasalazine (e.g. Azulfidine®) have poor bioavailability, with only approximately 15% of the compound reaching the circulation following oral dosing (see, for example, Label for Azulfidine®sulfasalazine tablets, USP). A major toxicity concern is exposure of the gastrointestinal tract to sulfasalazine, where it causes nausea, diarrhea and cramping in a dose-dependent manner, see e.g. Weaver, J. *Clin. Rheumatol.* 5: 193-200 (1999). An additional toxicity concern is sulfapyridine, one of the metabolites of sulfasalazine. Sulfapyridine is highly (>70%) bioavailable and is believed to be produced by intestinal bacteria, see, e.g., Peppercorn, M., J. *Clin. Pharmacol.* 27: 260-265 (1987); Watkinson, G., *Drugs* 32: Suppl 1:1-11 (1986).

SUMMARY OF THE INVENTION

The present application provides methods targeting system $x_c^-$ as a therapeutic approach to diseases involving excessive glutamatergic signaling. The present application describes administering an inhibitor of system $x_c^-$, such as sulfasalazine, to treat neurodegenerative diseases involving excessive glutamatergic signaling, such as P-MS and ALS. Without being bound by any theory asserted herein, the working hypothesis is that system $x_c^-$, by releasing excessive amounts of glutamate, causes neuronal damage, thereby activating neuroinflammatory cells. This in turn elevates levels of system $x_c^-$, causing a positive feedback loop that damages and ultimately kills axons and neurons, including motor neurons. Inhibiting system $x_c^-$ with an inhibitor such as sulfasalazine can interrupt this feedback loop and can reduce damage to the axons and neurons, including motor neurons.

Thus, the present application provides methods of treatment of various diseases using system $x_c^-$ inhibitors, including methods using improved dosing regimens. In addition, the present application describes formulations of a system $x_c^-$ inhibitor, sulfasalazine, where those formulations increase the bioavailability of orally-administered sulfasalazine. Those formulations can be used in the treatment of neurodegenerative diseases and disorders as well as other diseases and disorders, including rheumatoid arthritis and ankylosing spondylitis (diseases for which sulfasalazine is currently approved in various markets).

Experiments described herein using a mouse model of neurodegeneration demonstrate that treatment with sulfasalazine significantly reduces levels of neuroinflammatory cells in the spinal cord (see Example 3), including both activated microglia and activated astrocytes. In addition, experiments described herein using a mouse model of ALS demonstrate that the administration of sulfasalazine increases absolute survival and the survival after onset of definitive neurological disease in the SOD1 mouse model of ALS (see Example 1). Thus, in various embodiments, the present invention provides methods for treating P-MS, ALS, and other neurodegenerative diseases by administering to the patient a pharmaceutical composition comprising a therapeutically effective amount of sulfasalazine and a pharmaceutically acceptable excipient. In certain embodiments, methods are provided for treating other neurodegenerative diseases involving excessive glutamatergic signaling comprising administering to the patient with such a neurodegenerative disease a pharmaceutical composition comprising a therapeutically effective amount of sulfasalazine and a pharmaceutically acceptable excipient, wherein the neurodegenerative disease is selected from Parkinson's disease, Alzheimer's disease, epilepsy, neuropathic pain, traumatic brain injury, Huntington's disease, ischemic stroke, Rett Syndrome, Frontotemporal Dementia, HIV-associated Dementia, Tuberous Sclerosis and Alexander disease.

Increasing the Bioavailability of Sulfasalazine

One challenge with treating P-MS, ALS and other diseases with pharmaceutical compositions comprising sulfasalazine is the poor oral bioavailability of the standard formulations of sulfasalazine. For example, only 15% of the sulfasalazine in an orally administered dose of Azulfidine is absorbed into the bloodstream(see Azulfidine Sulfasalazine Tablets Label, LAB-0241-3.0, revised October 2009). Because the level of sulfasalazine at the sites of action relevant to neurodegenerative diseases (such as the spinal cord) is proportional to the amount of sulfasalazine in the plasma (see Example 4), the poor bioavailability of the current oral formulation of sulfasalazine limits the amount of sulfasalazine that reaches such sites of action. Thus, use of a standard formulation of sulfasalazine to treat neurodegenerative diseases would require large oral doses of sulfasalazine to be administered. This would expose patients to high levels of sulfasalazine in the gastrointestinal tract and generate high levels of sulfapyridine in the plasma, thereby increasing toxicity. One of the aims of this invention is to address these issues by improving the oral bioavailability of sulfasalazine for the treatment of P-MS, ALS or other diseases, including non-neurodegenerative diseases. Increasing such bioavailability would allow dosing levels of sulfasalazine to be lower, with the further benefit of limiting gastrointestinal exposure to sulfasalazine and systemic exposure to sulfapyridine. The formulations provided herein are predicted to increase the therapeutic index for sulfasalazine in the treatment of various diseases.

The present invention provides various methods of treating various diseases and disorders using the compositions described herein in which the solubility and/or bioavailability of sulfasalazine has been increased. Such methods are described below.

In certain embodiments, there are provided methods for treating a disease or disorder in a patient comprising orally administering to the patient a pharmaceutical composition comprising a therapeutically effective amount of sulfasalazine and a pharmaceutically acceptable excipient, wherein the pharmaceutical composition is formulated such that oral administration of the formulated pharmaceutical composition to a rat results in a plasma level of sulfasalazine thirty minutes after such administration that is at least 25%, at least 50%, at least 100%, at least 150%, at least 200%, at least 250% or at least 300% higher than the plasma level of sulfasalazine thirty minutes after administration of the same dose level of crystalline sulfasalazine to a rat as determined by the method of Example 10. In certain embodiments, there are provided methods for treating a disease or disorder in a patient comprising orally administering to the patient a pharmaceutical composition comprising a therapeutically effective amount of sulfasalazine and a pharmaceutically acceptable excipient, wherein the pharmaceutical composition is formulated such that oral administration of the formulated pharmaceutical composition to a rat results in a plasma level of sulfasalazine thirty minutes after such administration that is about 25%, about 50%, about 100%, about 150%, about 200%, about 250% or about 300% higher than the plasma level of sulfasalazine thirty minutes after administration of the same dose level of crystalline sulfasalazine to a rat as determined by the method of Example 10. In yet other embodiments, there are provided methods for treating a disease or disorder in a patient comprising orally administering to the patient a pharmaceutical composition comprising a therapeutically effective amount of sulfasalazine and a pharmaceutically acceptable excipient, wherein the pharmaceutical composition is formulated such that oral administration of the formulated pharmaceutical composition to a rat results in a plasma level of sulfasalazine thirty minutes after such administration that is between about 25% and about 500%, inclusive, higher than the plasma level of sulfasalazine thirty minutes after administration of the same dose level of crystalline sulfasalazine to a rat as determined by the method of Example 10. In certain of those embodiments, the pharmaceutical composition is formulated such that oral administration of the formulated pharmaceutical composition to a rat results in a plasma level of sulfasalazine thirty minutes after such administration that is between about 75% and about 300%, inclusive, higher than the plasma level of sulfasalazine thirty minutes after administration of the same dose level of crystalline sulfasalazine to a rat as determined by the method of Example 10. In certain other of the embodiments, the pharmaceutical composition is formulated such that oral administration of the formulated pharmaceutical composition to a rat results in a plasma level of sulfasalazine thirty minutes after such administration that is between about 100% and about 200%, inclusive, higher than the plasma level of sulfasalazine thirty minutes after administration of the same dose level of crystalline sulfasalazine to a rat as determined by the method of Example 10. In certain of the embodiments described in this paragraph, the disease or disorder is a neurodegenerative disease or disorder such as P-MS or ALS. In certain of the embodiments described in this paragraph, the disease or disorder is other than a neurodegenerative disease or disorder. In certain of those embodiments, the disease or disorder is rheumatoid arthritis or ankylosing spondylitis. In certain embodiments described in this paragraph, the pharmaceutical composition is one of the pharmaceutical compositions provided by the present application. In certain of those embodiments, the pharmaceutical composition is in an oral dosage form or in a spray dried dispersion form.

In yet other embodiments, there are provided methods for treating P-MS in a patient comprising orally administering to the patient a pharmaceutical composition comprising a therapeutically effective amount of sulfasalazine and a pharmaceutically acceptable excipient, wherein the pharmaceutical composition is formulated such that oral administration of the formulated pharmaceutical composition to a rat results in a plasma level of sulfasalazine thirty minutes after such administration that is at least 25%, at least 50%, at least 100%, at least 150%, at least 200%, at least 250% or at least 300% higher than the plasma level of sulfasalazine thirty minutes after administration of the same dose level of crystalline sulfasalazine to a rat as determined by the method of Example 10. In certain embodiments, there are provided methods for treating P-MS in a patient comprising orally administering to the patient a pharmaceutical composition comprising a therapeutically effective amount of sulfasalazine and a pharmaceutically acceptable excipient, wherein the pharmaceutical composition is formulated such that oral administration of the formulated pharmaceutical composition to a rat results in a plasma level of sulfasalazine thirty minutes after such administration that is about 25%, about 50%, about 100%, about 150%, about 200%, about 250% or about 300% higher than the plasma level of sulfasalazine thirty minutes after administration of the same dose level of crystalline sulfasalazine to a rat as determined by the method of Example 10. In yet other embodiments, there are provided methods for treating P-MS in a patient comprising orally administering to the patient a pharmaceutical composition comprising a therapeutically effective amount of sulfasalazine and a pharmaceutically acceptable excipient, wherein the pharmaceutical composition is formulated such that oral administration of the formulated pharmaceutical composition to a rat results in a plasma level of sulfasalazine thirty minutes after such administration that is between about 25% and about 500%, inclusive, higher than the plasma level of sulfasalazine thirty minutes after administration of the same dose level of crystalline sulfasalazine to a rat as determined by the method of Example 10. In certain of those embodiments, the pharmaceutical composition is formulated such that oral administration of the formulated pharmaceutical composition to a rat results in a plasma level of sulfasalazine thirty minutes after such administration that is between about 75% and about 300%, inclusive, higher than the plasma level of sulfasalazine thirty minutes after administration of the same dose level of crystalline sulfasalazine to a rat as determined by the method of Example 10. In certain of those embodiments, the pharmaceutical composition is formulated such that oral administration of the formulated pharmaceutical composition to a rat results in a plasma level of sulfasalazine thirty minutes after such administration that is between about 100% and about 200%, inclusive, higher than the plasma level of sulfasalazine thirty minutes after administration of the same dose level of crystalline sulfasalazine to a rat as determined by the method of Example 10. In certain embodiments described in this paragraph, the pharmaceutical composition is one of the pharmaceutical compositions provided by the present application. In certain of those embodiments, the pharmaceutical composition is in an oral dosage form or in a spray dried dispersion form.

In yet other embodiments, there are provided methods for treating ALS in a patient comprising orally administering to the patient a pharmaceutical composition comprising a therapeutically effective amount of sulfasalazine and a pharmaceutically acceptable excipient, wherein the pharmaceutical composition is formulated such that oral administration of the formulated pharmaceutical composition to a rat results in a plasma level of sulfasalazine thirty minutes after such administration that is at least 25%, at least 50%, at least 100%, at least 150%, at least 200%, at least 250% or at least 300% higher than the plasma level of sulfasalazine thirty minutes after administration of the same dose level of crystalline sulfasalazine to a rat as determined by the method of Example 10. In certain embodiments, there are provided methods for treating ALS in a patient comprising orally administering to the patient a pharmaceutical composition comprising a therapeutically effective amount of sulfasalazine and a pharmaceutically acceptable excipient, wherein the pharmaceutical composition is formulated such that oral administration of the formulated pharmaceutical composition to a rat results in a plasma level of sulfasalazine thirty minutes after such administration that is about 25%, about 50%, about 100%, about 150%, about 200%, about 250% or about 300% higher than the plasma level of sulfasalazine thirty minutes after administration of the same dose level of crystalline sulfasalazine to a rat as determined by the method of Example 10. In yet other embodiments, there are provided methods for treating ALS in a patient comprising orally administering to the patient a pharmaceutical composition comprising a therapeutically effective amount of sulfasalazine and a pharmaceutically acceptable excipient, wherein the pharmaceutical composition is formulated such that oral administration of the formulated pharmaceutical composition to a rat results in a plasma level of sulfasalazine thirty minutes after such administration that is between about 25% and about 500%, inclusive, higher than the plasma level of sulfasalazine thirty minutes after administration of the same dose level of crystalline sulfasalazine to a rat as determined by the method of Example 10. In certain of those embodiments, the pharmaceutical composition is formulated such that oral administration of the formulated pharmaceutical composition to a rat results in a plasma level of sulfasalazine thirty minutes after such administration that is between about 75% and about 300%, inclusive, higher than the plasma level of sulfasalazine thirty minutes after administration of the same dose level of crystalline sulfasalazine to a rat as determined by the method of Example 10. In certain of those embodiments, the pharmaceutical composition is formulated such that oral administration of the formulated pharmaceutical composition to a rat results in a plasma level of sulfasalazine thirty minutes after such administration that is between about 100% and about 200%, inclusive, higher than the plasma level of sulfasalazine thirty minutes after administration of the same dose level of crystalline sulfasalazine to a rat as determined by the method of Example 10. In certain embodiments described in this paragraph, the pharmaceutical composition is one of the pharmaceutical compositions provided by the present application. In certain of those embodiments, the pharmaceutical composition is in an oral dosage form or in a spray dried dispersion form.

In yet other embodiments, there are provided methods for treating neuropathic pain in a patient comprising orally administering to the patient a pharmaceutical composition comprising a therapeutically effective amount of sulfasalazine and a pharmaceutically acceptable excipient, wherein the pharmaceutical composition is formulated such that oral administration of the formulated pharmaceutical composition to a rat results in a plasma level of sulfasalazine thirty minutes after such administration that is at least 25%, at least 50%, at least 100%, at least 150%, at least 200%, at least 250% or at least 300% higher than the plasma level of sulfasalazine thirty minutes after administration of the same dose level of crystalline sulfasalazine to a rat as determined by the method of Example 10. In certain embodiments, there are provided methods for treating neuropathic pain in a patient comprising orally administering to the patient a pharmaceutical composition comprising a therapeutically effective amount of sulfasalazine and a pharmaceutically acceptable excipient, wherein the pharmaceutical composition is formulated such that oral administration of the formulated pharmaceutical composition to a rat results in a plasma level of sulfasalazine thirty minutes after such administration that is about 25%, about 50%, about 100%, about 150%, about 200%, about 250% or about 300% higher than the plasma level of sulfasalazine thirty minutes after administration of the same dose level of crystalline sulfasalazine to a rat as determined by the method of Example 10. In yet other embodiments, there are provided methods for treating neuropathic pain in a patient comprising orally administering to the patient a pharmaceutical composition comprising a therapeutically effective amount of sulfasalazine and a pharmaceutically acceptable excipient, wherein the pharmaceutical composition is formulated such that oral administration of the formulated pharmaceutical composition to a rat results in a plasma level of sulfasalazine thirty minutes after such administration that is between about 25% and about 500%, inclusive, higher than the plasma level of sulfasalazine thirty minutes after administration of the same dose level of crystalline sulfasalazine to a rat as determined by the method of Example 10. In certain of those embodiments, the pharmaceutical composition is formulated such that oral administration of the formulated pharmaceutical composition to a rat results in a plasma level of sulfasalazine thirty minutes after such administration that is between about 75% and about 300%, inclusive, higher than the plasma level of sulfasalazine thirty minutes after administration of the same dose level of crystalline sulfasalazine to a rat as determined by the method of Example 10. In certain of those embodiments, the pharmaceutical composition is formulated such that oral administration of the formulated pharmaceutical composition to a rat results in a plasma level of sulfasalazine thirty minutes after such administration that is between about 100% and about 200%, inclusive, higher than the plasma level of sulfasalazine thirty minutes after administration of the same dose level of crystalline sulfasalazine to a rat as determined by the method of Example 10. In some of the embodiments in this paragraph, the neuropathic pain results from painful diabetic neuropathy. In certain embodiments, the neuropathic pain manifests as dysesthesia. In certain embodiments, the neuropathic pain manifests as allodynia. In certain embodiments described in this paragraph, the pharmaceutical composition is one of the pharmaceutical compositions provided by the present application. In certain of those embodiments, the pharmaceutical composition is in an oral dosage form or in a spray dried dispersion form.

Formulations of the Invention

The present invention provides various pharmaceutical compositions comprising sulfasalazine that have been formulated to increase the bioavailability of the sulfasalazine. One way to increase the bioavailability of an orally-administered poorly soluble drug such as sulfasalazine is to increase the solubility of the drug. The invention provides various reformulations of sulfasalazine that increase the solubility of sulfasalazine (for three non-limiting examples, see Example 6 herein).

In some embodiments, there is provided a pharmaceutical composition comprising sulfasalazine and a pharmaceutically acceptable excipient, wherein the pharmaceutical composition has been formulated such that the in vitro solubility of the sulfasalazine is at least 2300 μg/ml at a pH of 5.5 determined as in Example 9. For the purposes of this application, the "in vitro solubility" of sulfasalazine will be considered to be the $C_{max}$ IB at 90 minutes as shown in Example 9 and Table 9 of this application. In other embodiments, there is provided a pharmaceutical composition comprising sulfasalazine and a pharmaceutically acceptable excipient, wherein the pharmaceutical composition has been formulated such that the in vitro solubility of the sulfasalazine is at least 500 μg/ml or at least 1200 μg/ml at a pH of 5.5 determined as in Example 9. In some embodiments, there is provided a pharmaceutical composition comprising sulfasalazine and a pharmaceutically acceptable excipient, wherein the pharmaceutical composition has been formulated such that the in vitro solubility of the sulfasalazine is about 500 μg/ml, about 1200 μg/ml, or about 2300 μg/ml at a pH of 5.5 determined as in Example 9. In some embodiments, there is provided a pharmaceutical composition comprising sulfasalazine and a pharmaceutically acceptable excipient, wherein the pharmaceutical composition has been formulated such that the in vitro solubility of the sulfasalazine is between about 500 μg/ml and about 11,500 μg/ml, inclusive, at a pH of 5.5 determined as in Example 9. In another embodiment of the composition, the in vitro solubility of the sulfasalazine is between about 500 μg/ml and about 7,500 μg/ml, inclusive, at a pH of 5.5 determined as in Example 9. In yet another embodiment of the composition, the in vitro solubility of the sulfasalazine is between about 500 μg/ml and about 5,500 μg/ml, inclusive, at a pH of 5.5 determined as in Example 9. In certain of those embodiments, the pharmaceutical composition has been formulated such that the in vitro solubility of the sulfasalazine is between about 500 μg/ml and about 2500 μg/ml, inclusive, at a pH of 5.5 determined as in Example 9. In certain of those embodiments, the pharmaceutical composition has been formulated such that the in vitro solubility of the sulfasalazine is between about 2300 μg/ml and about 11,500 μg/ml, inclusive, at a pH of 5.5 determined as in Example 9. In certain embodiments in this paragraph, the sulfasalazine is in an essentially amorphous form.

In some embodiments, there is provided an oral dosage form for sulfasalazine comprising a therapeutically effective amount of sulfasalazine and a pharmaceutically acceptable excipient, wherein the oral dosage form has been formulated such that the in vitro solubility of the sulfasalazine is at least 2300 μg/ml at a pH of 5.5 determined as in Example 9. In other embodiments, there is provided an oral dosage form for sulfasalazine comprising a therapeutically effective amount of sulfasalazine and a pharmaceutically acceptable excipient, wherein the oral dosage form has been formulated such that the in vitro solubility of the sulfasalazine is at least 500 μg/ml or at least 1200 μg/ml, inclusive, at a pH of 5.5 determined as in Example 9. In some embodiments, there is provided an oral dosage form for sulfasalazine comprising a therapeutically effective amount of sulfasalazine and a pharmaceutically acceptable excipient, wherein the oral dosage form has been formulated such that the in vitro solubility of the sulfasalazine is about 500 μg/ml, about 1200 μg/ml, or about 2300 μg/ml at a pH of 5.5 determined as in Example 9. In some embodiments, there is provided an oral dosage form for sulfasalazine comprising a therapeutically effective amount of sulfasalazine and a pharmaceutically acceptable excipient, wherein the oral dosage form has been formulated such that the in vitro solubility of the sulfasalazine is between about 500 μg/ml and about 11,500 μg/ml, inclusive, at a pH of 5.5 determined as in Example 9. In certain other embodiments, the oral dosage form has been formulated such that the in vitro solubility of the sulfasalazine is between about 500 μg/ml and about 2500 μg/ml at a pH of 5.5 determined as in Example 9. In certain of those embodiments, the oral dosage form has been formulated such that the in vitro solubility of the sulfasalazine is between about 2300 μg/ml and about 11,500 μg/ml, inclusive, at a pH of 5.5 determined as in Example 9. In another embodiment, the oral dosage form has been formulated such that the in vitro solubility of the sulfasalazine is between about 2300 μg/ml and about 7,500 μg/ml, inclusive, at a pH of 5.5 determined as in Example 9. In another embodiment, the oral dosage form has been formulated such that the in vitro solubility of the sulfasalazine is between about 2300 μg/ml and about 5,500 μg/ml, inclusive, at a pH of 5.5 determined as in Example 9. In certain embodiments in this paragraph, the sulfasalazine is in an essentially amorphous form.

In some embodiments, there is provided a pharmaceutical composition comprising sulfasalazine and a pharmaceutically acceptable excipient, wherein the pharmaceutical composition has been formulated such that the in vitro solubility of the sulfasalazine at a pH of 5.5 as determined as in Example 9 is at least 2 times higher than the in vitro solubility of crystalline sulfasalazine in aqueous solution at a pH of 5.5. In certain of those embodiments, the pharmaceutical composition is formulated such that the in vitro solubility of the sulfasalazine at a pH of 5.5 as determined in Example 9 is at least 5 times or at least 8.8 times higher than the in vitro solubility of crystalline sulfasalazine at a pH of 5.5 by AUC analysis. In some embodiments, there is provided a pharmaceutical composition comprising sulfasalazine and a pharmaceutically acceptable excipient, wherein the pharmaceutical composition is formulated such that the in vitro solubility of the sulfasalazine at a pH of 5.5 as determined as in Example 9 is about 2 times, about 5 times, or about 8.8 times higher than the in vitro solubility of crystalline sulfasalazine at a pH of 5.5 by AUC analysis. In some embodiments, there is provided a pharmaceutical composition comprising sulfasalazine and a pharmaceutically acceptable excipient, wherein the pharmaceutical composition is formulated such that the in vitro solubility of the sulfasalazine at a pH of 5.5 as determined as in Example 9 is between about 2 times and about 44 times, inclusive, higher than the in vitro solubility of crystalline sulfasalazine at a pH of 5.5 by AUC analysis. In certain of those embodiments, pharmaceutical composition is formulated such that the in vitro solubility of the sulfasalazine at a pH of 5.5 as determined as in Example 9 is between about 2 times and about 8.8 times, inclusive, higher than the in vitro solubility of crystalline sulfasalazine at a pH of 5.5 by AUC analysis. In certain other embodiments, pharmaceutical composition is formulated such that the in vitro solubility of the sulfasalazine at a pH of 5.5 as determined as in Example 9 is between about 8.8 times and about 44 times, inclusive, higher than the in vitro solubility of crystalline sulfasalazine at a pH of 5.5 by AUC analysis. In certain embodiments in this paragraph, the sulfasalazine is in an essentially amorphous form.

In some embodiments, there is provided an oral dosage form for sulfasalazine comprising a therapeutically effective amount of sulfasalazine and a pharmaceutically acceptable excipient, wherein the oral dosage form is formulated such that the in vitro solubility of the sulfasalazine at a pH of 5.5 as determined as in Example 9 is at least 2 times higher than the in vitro solubility of crystalline sulfasalazine at a pH of 5.5. In certain of those embodiments, the pharmaceutical composition is formulated such that the in vitro solubility of the sulfasalazine at a pH of 5.5 as determined in Example 9 is at least 5 times or at least 8.8 times higher than the in vitro solubility of crystalline sulfasalazine at a pH of 5.5 by AUC analysis. In some embodiments, there is provided an oral dosage form for sulfasalazine comprising a therapeutically effective amount of sulfasalazine and a pharmaceutically acceptable excipient, wherein the oral dosage form is formulated such that the in vitro solubility of the sulfasalazine at a pH of 5.5 as determined as in Example 9 is about 2 times, about 5 times, or about 8.8 times higher than the in vitro solubility of crystalline sulfasalazine at a pH of 5.5 by AUC analysis. In some embodiments, there is provided an oral dosage form for sulfasalazine comprising a therapeutically effective amount of sulfasalazine and a pharmaceutically acceptable excipient, wherein the oral dosage form is formulated such that the in vitro solubility of the sulfasalazine at a pH of 5.5 as determined as in Example 9 is between about 2 times and about 44 times, inclusive, higher than the in vitro solubility of crystalline sulfasalazine at a pH of 5.5 by AUC analysis. In certain of those embodiments, the oral dosage form is formulated such that the in vitro solubility of the sulfasalazine at a pH of 5.5 as determined as in Example 9 is between about 2 times and about 8.8 times, inclusive, higher than the in vitro solubility of crystalline sulfasalazine at a pH of 5.5 by AUC analysis. In certain other embodiments, the oral dosage form is formulated such that the in vitro solubility of the sulfasalazine at a pH of 5.5 as determined as in Example 9 is between about 8.8 times and about 44 times, inclusive, higher than the in vitro solubility of crystalline sulfasalazine at a pH of 5.5 by AUC analysis. In certain embodiments in this paragraph, the sulfasalazine is in an essentially amorphous form.

In some embodiments, there is provided a pharmaceutical composition comprising sulfasalazine and a pharmaceutically acceptable excipient, wherein the pharmaceutical composition has been formulated such that oral administration of such formulated pharmaceutical composition to a rat results in a plasma level of sulfasalazine thirty minutes after such administration that is at least 25%, at least 50%, at least 100%, at least 150%, at least 200%, at least 250%, or at least 300% higher than the plasma level of sulfasalazine thirty minutes after administration of the same dose level of crystalline sulfasalazine to a rat as determined in Example 10. In some embodiments, there is provided a pharmaceutical composition comprising sulfasalazine and a pharmaceutically acceptable excipient, wherein the pharmaceutical composition has been formulated such that oral administration of the formulated pharmaceutical composition to a rat results in a plasma level of sulfasalazine thirty minutes after such administration that is about 25%, about 50%, about 100%, about 150%, about 200%, about 250% or about 300% higher than the plasma level of sulfasalazine thirty minutes after administration of the same dose level of crystalline sulfasalazine to a rat as determined by the method of Example 10. In some embodiments, there is provided a pharmaceutical composition comprising sulfasalazine and a pharmaceutically acceptable excipient, wherein the pharmaceutical composition has been formulated such that oral administration of such formulated pharmaceutical composition to a rat results in a plasma level of sulfasalazine thirty minutes after such administration that is between about 25% and about 500%, inclusive, higher than the plasma level of sulfasalazine thirty minutes after administration of the same dose level of crystalline sulfasalazine to a rat as determined in Example 10. In certain of those embodiments, the pharmaceutical composition has been formulated such that oral administration of such formulated pharmaceutical composition to a rat results in a plasma level of sulfasalazine thirty minutes after such administration that is between about 75% and about 300%, inclusive, higher than the plasma level of sulfasalazine thirty minutes after administration of the same dose level of crystalline sulfasalazine to a rat as determined in Example 10. In certain of those embodiments, the pharmaceutical composition has been formulated such that oral administration of such formulated pharmaceutical composition to a rat results in a plasma level of sulfasalazine thirty minutes after such administration that is between about 300% and about 500%, inclusive, higher than the plasma level of sulfasalazine thirty minutes after administration of the same dose level of crystalline sulfasalazine to a rat as determined in Example 10. In certain embodiments in this paragraph, the sulfasalazine is in an essentially amorphous form.

In some embodiments, there is provided an oral dosage form for sulfasalazine comprising a therapeutically effective amount of sulfasalazine and a pharmaceutically acceptable excipient, wherein the oral dosage form is formulated such that oral administration of such formulated oral dosage form to a rat results in a plasma level of sulfasalazine thirty minutes after such administration that is at least 25%, at least 50%, at least 100%, at least 150%, at least 200%, at least 250%, or at least 300% higher than the plasma level of sulfasalazine thirty minutes after administration of the same dose level of crystalline sulfasalazine to a rat as determined in Example 10. In some embodiments, there is provided an oral dosage form for sulfasalazine comprising a therapeutically effective amount of sulfasalazine and a pharmaceutically acceptable excipient, wherein the oral dosage form is formulated such that oral administration of such formulated oral dosage form to a rat results in a plasma level of sulfasalazine thirty minutes after such administration that is between about 25% and about 500%, inclusive, higher than the plasma level of sulfasalazine thirty minutes after administration of the same dose level of crystalline sulfasalazine to a rat as determined in Example 10. In certain of those embodiments, the oral dosage form is formulated such that oral administration of such formulated oral dosage form to a rat results in a plasma level of sulfasalazine thirty minutes after such administration that is between about 75% and about 300%, inclusive, higher than the plasma level of sulfasalazine thirty minutes after administration of the same dose level of crystalline sulfasalazine to a rat as determined in Example 10. In certain of those embodiments, the oral dosage form is formulated such that oral administration of such formulated oral dosage form to a rat results in a plasma level of sulfasalazine thirty minutes after such administration that is between about 300% and about 500% higher, inclusive, than the plasma level of sulfasalazine thirty minutes after administration of the same dose level of crystalline sulfasalazine to a rat as determined in Example 10. In certain embodiments in this paragraph, the sulfasalazine is in an essentially amorphous form.

In certain embodiments of the compositions and methods described in this application, the composition comprises a pharmaceutically acceptable polymer. In certain embodiments, the pharmaceutically acceptable polymer may be selected from polyvinylpyrrolidone (PVP, including PVP VA64, homo- and copolymers of polyvinylpyrrolidone and homopolymers or copolymers of N-vinylpyrrolidone); crospovidone; polyoxyethylene-polyoxypropylene copolymers (also known as poloxamers); cellulose derivatives (including hydroxypropyl methyl cellulose acetate succinate (HPMCAS), hydroxypropyl methyl cellulose phthalate (HP-MCP), hydroxypropyl methylcellulose (HPMC), cellulose acetate phthalate (CAP), cellulose acetate trimellitate (CAT), hydroxypropyl methyl cellulose acetate phthalate, hydroxypropyl methyl cellulose acetate trimellitate, cellulose acetate succinate, methylcellulose acetate succinate, carboxymethyl ethyl cellulose (CMEC), hydroxypropyl methyl cellulose, hydroxypropyl methyl cellulose acetate, hydroxyethylcellulose and others); dextran; cyclodextrins; homo- and copolymers of vinyllactam, and mixtures thereof; gelatins; hypromellose phthalate; sugars; polyhydric alcohols; polyethylene glycol (PEG); polyethylene oxides; polyoxyethylene derivatives; polyvinyl alcohol; propylene glycol derivatives and the like; SLS; Tween; EUDRAGIT (a methacrylic acid and methyl methacrylate copolymer); and combinations thereof. The polymer may be water soluble or water insoluble. In certain embodiments, the ratio of the sulfasalazine to polymer in the composition is about 5:95 wt/wt to 50:50 wt/wt.

In certain embodiments, pharmaceutical compositions comprising amorphous or essentially amorphous sulfasalazine and a pharmaceutically acceptable polymer are provided. In certain of those embodiments, the pharmaceutical compositions are in the form of a solid dispersion. In certain embodiments, the pharmaceutically acceptable polymer may be selected from polyvinylpyrrolidone (PVP, including PVP VA64, homo- and copolymers of polyvinylpyrrolidone and homopolymers or copolymers of N-vinylpyrrolidone); crospovidone; polyoxyethylene-polyoxypropylene copolymers (also known as poloxamers); cellulose derivatives (including hydroxypropyl methyl cellulose acetate succinate (HPMCAS), hydroxypropyl methyl cellulose phthalate (HP-MCP), hydroxypropyl methylcellulose (HPMC), cellulose acetate phthalate (CAP), cellulose acetate trimellitate (CAT), hydroxypropyl methyl cellulose acetate phthalate, hydroxypropyl methyl cellulose acetate trimellitate, cellulose acetate succinate, methylcellulose acetate succinate, carboxymethyl ethyl cellulose (CMEC), hydroxypropyl methyl cellulose, hydroxypropyl methyl cellulose acetate, hydroxyethylcellulose and others); dextran; cyclodextrins; homo- and copolymers of vinyllactam, and mixtures thereof; gelatins; hypromellose phthalate; sugars; polyhydric alcohols; polyethylene glycol (PEG); polyethylene oxides; polyoxyethylene derivatives; polyvinyl alcohol; propylene glycol derivatives and the like; SLS; Tween; EUDRAGIT (a methacrylic acid and methyl methacrylate copolymer); and combinations thereof. The polymer may be water soluble or water insoluble. In certain embodiments, the ratio of the sulfasalazine to polymer in the composition is about 5:95 wt/wt to 50:50 wt/wt.

In certain embodiments, the present invention provides pharmaceutical compositions comprising sulfasalazine and PVP VA64, wherein the ratio of the sulfasalazine to PVP VA64 in the composition is about 20:80 wt/wt to 30:70 wt/wt. In certain of those embodiments, the ratio of sulfasalazine to PVP VA64 is about 25:75 wt/wt. In certain of those embodiments, the pharmaceutical composition further comprises a pharmaceutically acceptable excipient. In certain embodiments, the present invention provides pharmaceutical compositions comprising sulfasalazine and PVP VA64, wherein the ratio of the sulfasalazine to PVP VA64 in the composition is about 20:80 wt/wt to 30:70 wt/wt; and wherein the sulfasalazine dispersed in the polymer is in an amorphous form. In certain of those embodiments, the ratio of sulfasalazine to PVP VA64 is about 25:75 wt/wt. In certain of those embodiments, the pharmaceutical composition further comprises a pharmaceutically acceptable excipient. In certain embodiments, the present invention provides pharmaceutical compositions comprising sulfasalazine and PVP VA64, wherein the ratio of the sulfasalazine to PVP VA64 in the composition is about 40:60 wt/wt to about 60:40 wt/wt; and wherein the sulfasalazine dispersed in the polymer is in an amorphous form. In certain of those embodiments, the ratio of sulfasalazine to PVP VA64 is about 50:50 wt/wt. In certain embodiments of the methods in this paragraph, the pharmaceutical composition is formulated such that the in vitro solubility of the sulfasalazine is at least 500 µg/ml, at least 1200 µg/ml or at least 2300 µg/ml at a pH of 5.5 determined as in Example 9. In certain embodiments of the methods of this paragraph, the pharmaceutical composition is formulated such that the in vitro solubility of the sulfasalazine is about 500 µg/ml, about 1200

μg/ml or about 2300 μg/ml at a pH of 5.5 determined as in Example 9. In certain embodiments of the methods of this paragraph, the pharmaceutical composition is formulated such that the in vitro solubility of the sulfasalazine is between about 500 μg/ml and about 11,500 μg/ml, inclusive, at a pH of 5.5 determined as in Example 9. In other embodiments, the pharmaceutical composition is formulated such that the in vitro solubility of the sulfasalazine is between about 500 μg/ml and about 7,500 μg/ml, inclusive, at a pH of 5.5 determined as in Example 9. In certain embodiments of the methods of this paragraph, the pharmaceutical composition is formulated such that the in vitro solubility of the sulfasalazine is between about 500 μg/ml and about 2500 μg/ml, inclusive, at a pH of 5.5 determined as in Example 9. In certain embodiments of the methods of this paragraph, the pharmaceutical composition is formulated such that the in vitro solubility of the sulfasalazine is between about 2300 μg/ml and about 11,500 μg/ml, inclusive, at a pH of 5.5 determined as in Example 9. In another embodiment, the pharmaceutical composition is formulated such that the in vitro solubility of the sulfasalazine is between about 2300 μg/ml and about 5,500 μg/ml, inclusive, at a pH of 5.5 determined as in Example 9. In other embodiments, the pharmaceutical composition is formulated such that the in vitro solubility of the sulfasalazine is between about 2300 μg/ml and about 7,500 μg/ml, inclusive, at a pH of 5.5 determined as in Example 9.

In other embodiments, there is provided a spray dried dispersion composition comprising sulfasalazine and PVP VA64 polymer, wherein the ratio of the sulfasalazine to PVP VA64 in the composition is about 20:80 wt/wt to 30:70 wt/wt. In one aspect of the above embodiment, wherein the ratio of sulfasalazine to PVP VA64 is about 25:75 wt/wt. In certain of the embodiments, the pharmaceutical composition further comprises a pharmaceutically acceptable excipient. In other embodiments, there is provided a spray dried dispersion composition comprising sulfasalazine and PVP VA64 polymer, wherein the ratio of the sulfasalazine to PVP VA64 in the composition is about 20:80 wt/wt to 30:70 wt/wt; wherein the sulfasalazine dispersed in the polymer is in an essentially amorphous form. In certain of those embodiments, wherein the sulfasalazine dispersed in the polymer is in an amorphous form. In one aspect of the above embodiment, wherein the ratio of sulfasalazine to PVP VA64 is about 25:75 wt/wt. In certain of the embodiments, the pharmaceutical composition further comprises a pharmaceutically acceptable excipient. In another aspect of the above, the spray dried dispersion composition is formulated such that the in vitro solubility of the sulfasalazine is at least 500 μg/ml, at least 1200 μg/ml or at least 2300 μg/ml at a pH of 5.5 determined as in Example 9. In another aspect of the above, the spray dried dispersion composition is formulated such that the in vitro solubility of the sulfasalazine is about 500 μg/ml, about 1200 μg/ml or about 2300 μg/ml at a pH of 5.5 determined as in Example 9. In another aspect of the above, the spray dried dispersion composition is formulated such that the in vitro solubility of the sulfasalazine is between about 500 μg/ml and about 11,500 μg/ml, inclusive, at a pH of 5.5 determined as in Example 9. In another embodiment, the spray dried dispersion composition is formulated such that the in vitro solubility of the sulfasalazine is between about 500 μg/ml and about 7,500 μg/ml, inclusive, at a pH of 5.5 determined as in Example 9. In other embodiments, the spray dried dispersion composition is formulated such that the in vitro solubility of the sulfasalazine is between about 500 μg/ml and about 5,500 μg/ml, inclusive, at a pH of 5.5 determined as in Example 9. In other aspects of the above, the spray dried dispersion composition is formulated such that the in vitro solubility of the sulfasalazine is between about 500 μg/ml and about 2500 μg/ml, inclusive, at a pH of 5.5 determined as in Example 9. In other aspects of the above, the spray dried dispersion composition is formulated such that the in vitro solubility of the sulfasalazine is between about 2300 μg/ml and about 11,500 μg/ml, inclusive, at a pH of 5.5 determined as in Example 9.

In certain embodiments, the present invention provides pharmaceutical compositions comprising sulfasalazine and HPMCAS, wherein the ratio of the sulfasalazine to HPMCAS in the composition is about 20:80 wt/wt to 30:70 wt/wt. In certain of those embodiments, the ratio of sulfasalazine to HPMCAS is about 25:75 wt/wt. In certain embodiments, the present invention provides pharmaceutical compositions comprising sulfasalazine and HPMCAS, wherein the ratio of the sulfasalazine to HPMCAS in the composition is about 20:80 wt/wt to 30:70 wt/wt; wherein the sulfasalazine dispersed in the polymer is in an amorphous form. In certain of those embodiments, the ratio of sulfasalazine to HPMCAS is about 25:75 wt/wt. In certain embodiments of the pharmaceutical compositions of this paragraph, the pharmaceutical composition is formulated such that the in vitro solubility of the sulfasalazine is at least 500 μg/ml, at least 1200 μg/ml or at least 2300 μg/ml at a pH of 5.5 determined as in Example 9. In certain embodiments of the pharmaceutical compositions of this paragraph, the pharmaceutical composition is formulated such that the in vitro solubility of the sulfasalazine is about 500 μg/ml, about 1200 μg/ml or about 2300 μg/ml at a pH of 5.5 determined as in Example 9. In certain embodiments of the pharmaceutical compositions of this paragraph, the pharmaceutical composition is formulated such that the in vitro solubility of the sulfasalazine is between about 500 μg/ml and about 11,500 μg/ml, inclusive, at a pH of 5.5 determined as in Example 9. In other aspects of the above, the pharmaceutical composition is formulated such that the in vitro solubility of the sulfasalazine is between about 500 μg/ml and about 2500 μg/ml, inclusive, at a pH of 5.5 determined as in Example 9. In another aspect, the pharmaceutical composition is formulated such that the in vitro solubility of the sulfasalazine is between about 2300 μg/ml and about 5,500 μg/ml, inclusive, at a pH of 5.5 determined as in Example 9. In another aspect, pharmaceutical composition is formulated such that the in vitro solubility of the sulfasalazine is between about 2300 μg/ml and about 7,500 μg/ml, inclusive, at a pH of 5.5 determined as in Example 9. In other aspects of the above, the pharmaceutical composition is formulated such that the in vitro solubility of the sulfasalazine is between about 2300 μg/ml and about 11,500 μg/ml, inclusive, at a pH of 5.5 determined as in Example 9.

In certain embodiments, the present invention provides spray dried dispersion compositions comprising sulfasalazine and HPMCAS, wherein the ratio of the sulfasalazine to HPMCAS in the composition is about 20:80 wt/wt to 30:70 wt/wt. In certain of those embodiments, the ratio of sulfasalazine to HPMCAS is about 25:75 wt/wt. In certain embodiments, the present invention provides spray dried dispersion compositions comprising sulfasalazine and HPMCAS, wherein the ratio of the sulfasalazine to HPMCAS in the composition is about 20:80 wt/wt to 30:70 wt/wt; wherein the sulfasalazine dispersed in the polymer is in an essentially amorphous form. In certain of those embodiments, the sulfasalazine dispersed in the polymer is in an amorphous form. In some embodiments, there is provided a spray dried dispersion composition comprising sulfasalazine and HPMCAS polymer, wherein the ratio of the sulfasalazine to HPMCAS in the composition is about 20:80 wt/wt to 30:70 wt/wt; wherein the sulfasalazine dispersed in the polymer is in an essentially amorphous form and the spray dried dispersion composition is formulated such that the in vitro solubility of the sulfasalazine is at least 500 µg/ml, at least 1200 µg/ml or at least 2300 µg/ml at a pH of 5.5 determined as in Example 9. In one aspect of the above embodiment, the ratio of sulfasalazine to HPMCAS is about 25:75 wt/wt. In some embodiments, there is provided a spray dried dispersion composition comprising sulfasalazine and HPMCAS, wherein the ratio of the sulfasalazine to HPMCAS in the composition is about 20:80 wt/wt to 30:70 wt/wt; wherein the sulfasalazine dispersed in the polymer is in an essentially amorphous form and the spray dried dispersion composition is formulated such that the in vitro solubility of the sulfasalazine is between about 500 µg/ml and about 11,500 µg/ml, inclusive, at a pH of 5.5 determined as in Example 9. In another aspect, the spray dried dispersion composition is formulated such that the in vitro solubility of the sulfasalazine is between about 500 µg/ml and about 7,500 µg/ml, inclusive, at a pH of 5.5 determined as in Example 9. In certain of those embodiments, the spray dried dispersion composition is formulated such that the in vitro solubility of the sulfasalazine is between about 500 µg/ml and about 2500 µg/ml, inclusive, at a pH of 5.5 determined as in Example 9. In other of those embodiments, the spray dried dispersion composition is formulated such that the in vitro solubility of the sulfasalazine is between about 2300 µg/ml and about 11,500 µg/ml, inclusive, at a pH of 5.5 determined as in Example 9. In certain embodiments of the above embodiments, the ratio of sulfasalazine to HPMCAS is about 25:75 wt/wt.

In another embodiment, there is provided a spray dried dispersion composition comprising sulfasalazine and a pharmaceutically acceptable polymer. In certain embodiments, the pharmaceutically acceptable polymer may be selected from polyvinylpyrrolidone (PVP, including PVP VA64, homo- and copolymers of polyvinylpyrrolidone and homopolymers or copolymers of N-vinylpyrrolidone); crospovidone; polyoxyethylene-polyoxypropylene copolymers (also known as poloxamers); cellulose derivatives (including hydroxypropyl methyl cellulose acetate succinate (HPMCAS), hydroxypropyl methyl cellulose phthalate (HPMCP), hydroxypropyl methylcellulose (HPMC), cellulose acetate phthalate (CAP), cellulose acetate trimellitate (CAT), hydroxypropyl methyl cellulose acetate phthalate, hydroxypropyl methyl cellulose acetate trimellitate, cellulose acetate succinate, methylcellulose acetate succinate, carboxymethyl ethyl cellulose (CMEC), hydroxypropyl methyl cellulose, hydroxypropyl methyl cellulose acetate, hydroxyethylcellulose and others); dextran; cyclodextrins; homo- and copolymers of vinyllactam, and mixtures thereof; gelatins; hypromellose phthalate; sugars; polyhydric alcohols; polyethylene glycol (PEG); polyethylene oxides; polyoxyethylene derivatives; polyvinyl alcohol; propylene glycol derivatives and the like; SLS; Tween; EUDRAGIT (a methacrylic acid and methyl methacrylate copolymer); and combinations thereof. The polymer may be water soluble or water insoluble. In certain embodiments, the ratio of the sulfasalazine to polymer in the composition is about 5:95 wt/wt to 50:50 wt/wt. In certain of those embodiments, the sulfasalazine dispersed in the polymer is in an essentially amorphous form.

In certain embodiments of the compositions and methods provided in this application, the sulfasalazine is in an amorphous form or an essentially amorphous form. In certain embodiments of the compositions and methods provided in this application, the composition comprises PVP VA64 or HPMCAS. In certain of those embodiments, the ratio of the sulfasalazine to PVP VA64 or HPMCAS in the composition is about 20:80 wt/wt to 30:70 wt/wt or is about 25:75 wt/wt. In certain other of those embodiments, the ratio of the sulfasalazine to PVP VA64 in the composition is about 40:60 wt/wt to about 60:40 wt/wt or is about 50:50 wt/wt.

Treating Neurodegenerative Diseases and Disorders with the Formulations of the Invention In certain embodiments, the formulations of the present invention can be used in the treatment of neurodegenerative diseases and disorders as well as certain other diseases and disorders. For example, the various formulations and compositions comprising sulfasalazine described in this application can be used in the treatment of P-MS, ALS, neuropathic pain and other neurodegenerative diseases and disorders.

In certain embodiments, the application provides methods for treating P-MS in a patient comprising orally administering to the patient a pharmaceutical composition comprising a therapeutically effective amount of sulfasalazine and a pharmaceutically acceptable excipient, wherein the pharmaceutical composition is formulated such that the in vitro solubility of the sulfasalazine is at least 500 µg/ml, at least 1200 µg/ml or at least 2300 µg/ml at a pH of 5.5 determined as in Example 9. In certain embodiments, the application provides methods for treating P-MS in a patient comprising orally administering to the patient a pharmaceutical composition comprising a therapeutically effective amount of sulfasalazine and a pharmaceutically acceptable excipient, wherein the pharmaceutical composition is formulated such that the in vitro solubility of the sulfasalazine is at least 2300 µg/ml at a pH of 5.5 as determined in Example 9. In certain embodiments, the application provides methods for treating P-MS in a patient comprising orally administering to the patient a pharmaceutical composition comprising a therapeutically effective amount of sulfasalazine and a pharmaceutically acceptable excipient, wherein the pharmaceutical composition is formulated such that the in vitro solubility of the sulfasalazine is about 500 µg/ml, about 1200 µg/ml or about 2300 µg/ml at a pH of 5.5 as determined in Example 9. In certain embodiments, the application provides methods for treating P-MS in a patient comprising orally administering to the patient a pharmaceutical composition comprising a therapeutically effective amount of sulfasalazine and a pharmaceutically acceptable excipient, wherein the pharmaceutical composition is formulated such that the in vitro solubility of the sulfasalazine is between about 500 µg/ml and about 11,500 µg/ml, inclusive, at a pH of 5.5 determined as in Example 9. In certain of those embodiments, the pharmaceutical composition is formulated such that the in vitro solubility of the sulfasalazine is between about 500 µg/ml and about 2500 µg/ml, inclusive, at a pH of 5.5 determined as in Example 9. In another embodiment, the pharmaceutical composition is formulated such that the in vitro solubility of the sulfasalazine is between about 2300 µg/ml and about 5,500 µg/ml, inclusive, at a pH of 5.5 determined as in Example 9. In other embodiments, the pharmaceutical composition is formulated such that the in vitro solubility of the sulfasalazine is between about 2300 µg/ml and about 7,500 µg/ml, inclusive, at a pH of 5.5 determined as in Example 9. In certain other of those embodiments, the pharmaceutical composition is formulated such that the in vitro solubility of the sulfasalazine is between about 2300 µg/ml and about 11,500 µg/ml, inclusive, at a pH of 5.5 determined as in Example 9. In certain embodiments described in this paragraph, the pharmaceutical composition is one of the pharmaceutical compositions provided by the present application. In certain of those embodiments, the pharmaceutical composition is in an oral dosage form or in a spray dried dispersion form.

In certain embodiments, methods are provided for treating P-MS in a patient comprising orally administering to the patient a pharmaceutical composition comprising a therapeutically effective amount of sulfasalazine and a pharmaceutically acceptable excipient, wherein the pharmaceutical composition is formulated such that the in vitro solubility of the sulfasalazine at a pH of 5.5 as determined in Example 9 is at least 2 times higher than the in vitro solubility of crystalline sulfasalazine at a pH of 5.5 by AUC analysis. In certain of those embodiments, the pharmaceutical composition is formulated such that the in vitro solubility of the sulfasalazine at a pH of 5.5 as determined in Example 9 is at least 5 times or at least 8.8 times higher than the in vitro solubility of crystalline sulfasalazine at a pH of 5.5 by AUC analysis. In certain embodiments, methods are provided for treating P-MS in a patient comprising orally administering to the patient a pharmaceutical composition comprising a therapeutically effective amount of sulfasalazine and a pharmaceutically acceptable excipient, wherein the pharmaceutical composition is formulated such that the in vitro solubility of the sulfasalazine at a pH of 5.5 as determined in Example 9 is about 2 times, about 5 times, or about 8.8 times higher than the in vitro solubility of crystalline sulfasalazine at a pH of 5.5 by AUC analysis. In certain embodiments, methods are provided for treating P-MS in a patient comprising orally administering to the patient a pharmaceutical composition comprising a therapeutically effective amount of sulfasalazine and a pharmaceutically acceptable excipient, wherein the pharmaceutical composition is formulated such that the in vitro solubility of the sulfasalazine at a pH of 5.5 as determined in Example 9 is between about 2 times and about 44 times, inclusive, higher than the in vitro solubility of crystalline sulfasalazine at a pH of 5.5 by AUC analysis. In certain of those embodiments, the pharmaceutical composition is formulated such that the in vitro solubility of the sulfasalazine at a pH of 5.5 as determined as in Example 9 is between about 2 times and about 8.8 times, inclusive, higher than the in vitro solubility of crystalline sulfasalazine at a pH of 5.5 by AUC analysis. In certain other embodiments, the pharmaceutical composition is formulated such that the in vitro solubility of the sulfasalazine at a pH of 5.5 as determined as in Example 9 is between about 8.8 times and about 44 times, inclusive, higher than the in vitro solubility of crystalline sulfasalazine at a pH of 5.5 by AUC analysis. In certain embodiments described in this paragraph, the pharmaceutical composition is one of the pharmaceutical compositions provided by the present application. In certain of those embodiments, the pharmaceutical composition is in an oral dosage form or in a spray dried dispersion form.

In some embodiments, there are provided methods for treating a patient with P-MS comprising orally administering to the patient a pharmaceutical composition comprising a therapeutically effective amount of sulfasalazine and a pharmaceutically acceptable excipient, wherein the sulfasalazine is in an essentially amorphous form. In one aspect of the method, the in vitro solubility of the sulfasalazine from the composition is at least 500 µg/ml at a pH of 5.5 when measured by the method of Example 9. In another aspect of the invention, the in vitro solubility of the sulfasalazine is at least 1200 µg/ml or at least 2300 µg/ml. In certain embodiments, the application provides methods for treating P-MS in a patient comprising orally administering to the patient a pharmaceutical composition comprising a therapeutically effective amount of essentially amorphous sulfasalazine and a pharmaceutically acceptable excipient, wherein the in vitro solubility of the sulfasalazine is about 500 µg/ml, about 1200 µg/ml or about 2300 µg/ml at a pH of 5.5 as determined in Example 9. In other aspects of the invention, the in vitro solubility of the sulfasalazine is between about 500 µg/ml and about 11,500 µg/ml, inclusive. In other aspects of the invention, the in vitro solubility of the sulfasalazine is between about 500 µg/ml and about 2500 µg/ml, inclusive. In another aspect of the above, the in vitro solubility of the sulfasalazine is between about 2300 µg/ml and about 5,500 µg/ml, inclusive. In another aspect of the above, the in vitro solubility of the sulfasalazine is between about 2300 µg/ml and about 7,500 µg/ml, inclusive. In other aspects of the invention, the in vitro solubility of the sulfasalazine is between about 2300 µg/ml and about 11,500 µg/ml, inclusive.

In another aspect of the method, the pharmaceutical composition comprises a pharmaceutically acceptable polymer. In certain of those embodiments, the pharmaceutically acceptable polymer is a pyrrolidone polymer. In another aspect of the method, the pyrrolidone polymer is selected from polyvinylpyrrolidone, vinylpyrrolidone-vinyl acetate and crospovidone. In yet another aspect of the method, the pyrrolidone polymer is PVP VA64. In another aspect of the above method, the ratio of the sulfasalazine to PVP VA64 in the pharmaceutical composition is about 20:80 wt/wt to 30:70 wt/wt. In another aspect, the ratio of sulfasalazine to PVP VA64 is about 25:75 wt/wt. In certain embodiments described in this paragraph, the pharmaceutical composition is one of the pharmaceutical compositions provided by the present application. In certain of those embodiments, the pharmaceutical composition is in an oral dosage form or in a spray dried dispersion form.

In certain embodiments, the application provides methods for treating ALS in a patient comprising orally administering to the patient a pharmaceutical composition comprising a therapeutically effective amount of sulfasalazine and a pharmaceutically acceptable excipient, wherein the pharmaceutical composition is formulated such that the in vitro solubility of the sulfasalazine is at least 500 µg/ml, at least 1200 µg/ml or at least 2300 µg/ml at a pH of 5.5 determined as in Example 9. In certain embodiments, the application provides methods for treating ALS in a patient comprising orally administering to the patient a pharmaceutical composition comprising a therapeutically effective amount of sulfasalazine and a pharmaceutically acceptable excipient, wherein the pharmaceutical composition is formulated such that the in vitro solubility of the sulfasalazine is at least 2300 µg/ml at a pH of 5.5 as determined in Example 9. In certain embodiments, the application provides methods for treating ALS in a patient comprising orally administering to the patient a pharmaceutical composition comprising a therapeutically effective amount of sulfasalazine and a pharmaceutically acceptable excipient, wherein the pharmaceutical composition is formulated such that the in vitro solubility of the sulfasalazine is about 500 µg/ml, about 1200 µg/ml or about 2300 µg/ml at a pH of 5.5 as determined in Example 9. In certain embodiments, the application provides methods for treating ALS in a patient comprising orally administering to the patient a pharmaceutical composition comprising a therapeutically effective amount of sulfasalazine and a pharmaceutically acceptable excipient, wherein the pharmaceutical composition is formulated such that the in vitro solubility of the sulfasalazine is between about 500 µg/ml and about 11,500 µg/ml, inclusive, at a pH of 5.5 determined as in Example 9. In certain of those embodiments, the pharmaceutical composition is formulated such that the in vitro solubility of the sulfasalazine is between about 500 µg/ml and about 2500 µg/ml, inclusive, at a pH of 5.5 determined as in Example 9. In certain of those embodiments, the pharmaceutical composition is formulated such that the in vitro solubility of the sulfasalazine is between about 2300 µg/ml and about 11,500 µg/ml, inclusive, at a pH of 5.5 determined as in Example 9. In another embodiment of the above, the in vitro solubility of the sulfasalazine is between about 2300 µg/ml and about 7,500 µg/ml, inclusive, at a pH of 5.5 determined as in Example 9. In another embodiment of the above, the in vitro solubility of the sulfasalazine is between about 2300 µg/ml and about 5,500 µg/ml, inclusive, at a pH of 5.5 determined as in Example 9. In certain embodiments described in this paragraph, the pharmaceutical composition is one of the pharmaceutical compositions provided by the present application. In certain of those embodiments, the pharmaceutical composition is in an oral dosage form or in a spray dried dispersion form.

In certain embodiments, methods are provided for treating ALS in a patient comprising orally administering to the patient a pharmaceutical composition comprising a therapeutically effective amount of sulfasalazine and a pharmaceutically acceptable excipient, wherein the pharmaceutical composition is formulated such that the in vitro solubility of the sulfasalazine at a pH of 5.5 as determined in Example 9 is at least 2 times higher than the in vitro solubility of crystalline sulfasalazine at a pH of 5.5 by AUC analysis. In certain of those embodiments, the pharmaceutical composition is formulated such that the in vitro solubility of the sulfasalazine at a pH of 5.5 as determined in Example 9 is at least 5 times or at least 8.8 times higher than the in vitro solubility of crystalline sulfasalazine at a pH of 5.5 by AUC analysis. In certain embodiments, methods are provided for treating ALS in a patient comprising orally administering to the patient a pharmaceutical composition comprising a therapeutically effective amount of sulfasalazine and a pharmaceutically acceptable excipient, wherein the pharmaceutical composition is formulated such that the in vitro solubility of the sulfasalazine at a pH of 5.5 as determined in Example 9 is about 2 times, about 5 times, or about 8.8 times higher than the in vitro solubility of crystalline sulfasalazine at a pH of 5.5 by AUC analysis. In certain embodiments, methods are provided for treating ALS in a patient comprising orally administering to the patient a pharmaceutical composition comprising a therapeutically effective amount of sulfasalazine and a pharmaceutically acceptable excipient, wherein the pharmaceutical composition is formulated such that the in vitro solubility of the sulfasalazine at a pH of 5.5 as determined in Example 9 is between about 2 times and about 44 times, inclusive, higher than the in vitro solubility of crystalline sulfasalazine at a pH of 5.5 by AUC analysis. In certain of those embodiments, the pharmaceutical composition is formulated such that the in vitro solubility of the sulfasalazine at a pH of 5.5 as determined as in Example 9 is between about 2 times and about 8.8 times, inclusive, higher than the in vitro solubility of crystalline sulfasalazine at a pH of 5.5 by AUC analysis. In certain other embodiments, the pharmaceutical composition is formulated such that the in vitro solubility of the sulfasalazine at a pH of 5.5 as determined as in Example 9 is between about 8.8 times and about 44 times, inclusive, higher than the in vitro solubility of crystalline sulfasalazine at a pH of 5.5 by AUC analysis. In certain embodiments described in this paragraph, the pharmaceutical composition is one of the pharmaceutical compositions provided by the present application. In certain of those embodiments, the pharmaceutical composition is in an oral dosage form or in a spray dried dispersion form.

In some embodiments, there are provided methods for treating a patient with ALS comprising orally administering to the patient with ALS a pharmaceutical composition comprising a therapeutically effective amount of sulfasalazine and a pharmaceutically acceptable excipient, wherein the sulfasalazine is in an essentially amorphous form. In certain aspects of the method, the in vitro solubility of the sulfasalazine from the composition is at least 500 µg/ml at a pH of 5.5 when measured by the method of Example 9. In certain of those aspects, the in vitro solubility of the sulfasalazine is at least 1200 µg/ml or at least 2300 µg/ml. In certain embodiments, the application provides methods for treating ALS in a patient comprising orally administering to the patient a pharmaceutical composition comprising a therapeutically effective amount of essentially amorphous sulfasalazine and a pharmaceutically acceptable excipient, wherein the in vitro solubility of the sulfasalazine is about 500 µg/ml, about 1200 µg/ml or about 2300 µg/ml at a pH of 5.5 as determined in Example 9. In some embodiments, there are provided methods for treating a patient with ALS comprising orally administering to the patient with ALS a pharmaceutical composition comprising a therapeutically effective amount of essentially amorphous sulfasalazine and a pharmaceutically acceptable excipient, wherein the in vitro solubility of the sulfasalazine is between about 500 µg/ml and about 11,500 µg/ml, inclusive. In another embodiment, the in vitro solubility of the sulfasalazine is between about 500 µg/ml and about 7,500 µg/ml, inclusive. In another embodiment of the above, the in vitro solubility of the sulfasalazine is between about 500 µg/ml and about 5,500 µg/ml, inclusive. In certain of those embodiments, the in vitro solubility of the sulfasalazine is between about 500 µg/ml and about 2500 µg/ml, inclusive. In other of those embodiments, the in vitro solubility of the sulfasalazine is between about 2300 µg/ml and about 11,500 µg/ml, inclusive. In another aspect of the method, the pharmaceutical composition comprises a pharmaceutically acceptable polymer. In certain of those embodiments, the pharmaceutically acceptable polymer comprises a pyrrolidone polymer. In another aspect of the method, the pyrrolidone polymer is selected from polyvinylpyrrolidone, vinylpyrrolidone-vinyl acetate and crospovidone. In yet another aspect of the method, the pyrrolidone polymer is PVP VA64. In another aspect of the above method, the ratio of the sulfasalazine to PVP VA64 in the pharmaceutical composition is about 20:80 wt/wt to 30:70 wt/wt. In another aspect, the ratio of sulfasalazine to PVP VA64 is about 25:75 wt/wt. In certain embodiments described in this paragraph, the pharmaceutical composition is one of the pharmaceutical compositions provided by the present application. In certain of those embodiments, the pharmaceutical composition is in an oral dosage form or in a spray dried dispersion form.

In certain embodiments, the application provides methods for treating neuropathic pain in a patient comprising orally administering to the patient a pharmaceutical composition comprising a therapeutically effective amount of sulfasalazine and a pharmaceutically acceptable excipient, wherein the pharmaceutical composition is formulated such that the in vitro solubility of the sulfasalazine is at least 500 µg/ml, at least 1200 µg/ml or at least 2300 µg/ml at a pH of 5.5 determined as in Example 9. In certain embodiments, the application provides methods for treating neuropathic pain in a patient comprising orally administering to the patient a pharmaceutical composition comprising a therapeutically effective amount of sulfasalazine and a pharmaceutically acceptable excipient, wherein the pharmaceutical composition is formulated such that the in vitro solubility of the sulfasalazine is about 500 µg/ml, about 1200 µg/ml or about 2300 µg/ml at a pH of 5.5 as determined in Example 9. In certain embodiments, the application provides methods for treating neuropathic pain in a patient comprising orally administering to the patient a pharmaceutical composition comprising a therapeutically effective amount of sulfasalazine and a pharmaceutically acceptable excipient, wherein the pharmaceutical composition is formulated such that the in vitro solubility of the sulfasalazine is between about 500 µg/ml and about 11,500 µg/ml, inclusive, at a pH of 5.5 determined as in Example 9. In another embodiment, the in vitro solubility of the sulfasalazine is between about 500 µg/ml and about 7,500 µg/ml, inclusive, at a pH of 5.5 determined as in Example 9. In another embodiment, the in vitro solubility of the sulfasalazine is between about 500 µg/ml and about 5,500 µg/ml, inclusive, at a pH of 5.5 determined as in Example 9. In certain of those embodiments, the pharmaceutical composition is formulated such that the in vitro solubility of the sulfasalazine is between about 500 µg/ml and about 2500 µg/ml, inclusive, at a pH of 5.5 determined as in Example 9. In certain of those embodiments, the pharmaceutical composition is formulated such that the in vitro solubility of the sulfasalazine is between about 2300 µg/ml and about 11,500 µg/ml, inclusive, at a pH of 5.5 determined as in Example 9. In some of the embodiments in this paragraph, the neuropathic pain results from painful diabetic neuropathy. In certain embodiments, the neuropathic pain manifests as dysesthesia. In certain embodiments, the neuropathic pain manifests as allodynia. In certain embodiments described in this paragraph, the pharmaceutical composition is one of the pharmaceutical compositions provided by the present application. In certain of those embodiments, the pharmaceutical composition is in an oral dosage form or in a spray dried dispersion form.

In certain embodiments, methods are provided for treating neuropathic pain in a patient comprising orally administering to the patient a pharmaceutical composition comprising a therapeutically effective amount of sulfasalazine and a pharmaceutically acceptable excipient, wherein the pharmaceutical composition is formulated such that the in vitro solubility of the sulfasalazine at a pH of 5.5 as determined in Example 9 is at least 2 times higher than the in vitro solubility of crystalline sulfasalazine at a pH of 5.5 by AUC analysis. In certain of those embodiments, the pharmaceutical composition is formulated such that the in vitro solubility of the sulfasalazine at a pH of 5.5 as determined in Example 9 is at least 5 times or at least 8.8 times higher than the in vitro solubility of crystalline sulfasalazine at a pH of 5.5 by AUC analysis. In certain embodiments, methods are provided for treating neuropathic pain in a patient comprising orally administering to the patient a pharmaceutical composition comprising a therapeutically effective amount of sulfasalazine and a pharmaceutically acceptable excipient, wherein the pharmaceutical composition is formulated such that the in vitro solubility of the sulfasalazine at a pH of 5.5 as determined in Example 9 is about 2 times, about 5 times, or about 8.8 times higher than the in vitro solubility of crystalline sulfasalazine at a pH of 5.5 by AUC analysis. In certain embodiments, methods are provided for treating neuropathic pain in a patient comprising orally administering to the patient a pharmaceutical composition comprising a therapeutically effective amount of sulfasalazine and a pharmaceutically acceptable excipient, wherein the pharmaceutical composition is formulated such that the in vitro solubility of the sulfasalazine at a pH of 5.5 as determined in Example 9 is between about 2 times and about 44 times, inclusive, higher than the in vitro solubility of crystalline sulfasalazine at a pH of 5.5 by AUC analysis. In certain of those embodiments, the pharmaceutical composition is formulated such that the in vitro solubility of the sulfasalazine at a pH of 5.5 as determined as in Example 9 is between about 2 times and about 8.8 times, inclusive, higher than the in vitro solubility of crystalline sulfasalazine at a pH of 5.5 by AUC analysis. In certain other embodiments, the pharmaceutical composition is formulated such that the in vitro solubility of the sulfasalazine at a pH of 5.5 as determined as in Example 9 is between about 8.8 times and about 44 times, inclusive, higher than the in vitro solubility of crystalline sulfasalazine at a pH of 5.5 by AUC analysis. In some of the embodiments in this paragraph, the neuropathic pain results from painful diabetic neuropathy. In certain embodiments, the neuropathic pain manifests as dysesthesia. In certain embodiments, the neuropathic pain manifests as allodynia. In certain embodiments described in this paragraph, the pharmaceutical composition is one of the pharmaceutical compositions provided by the present application. In certain of those embodiments, the pharmaceutical composition is in an oral dosage form or in a spray dried dispersion form.

In some embodiments, there are provided methods for treating a patient with neuropathic pain comprising orally administering to the patient a pharmaceutical composition comprising a therapeutically effective amount of sulfasalazine and a pharmaceutically acceptable excipient, wherein the sulfasalazine is in an essentially amorphous form. In certain aspects of the method, the in vitro solubility of the sulfasalazine from the composition is at least 500 µg/ml at a pH of 5.5 when measured by the method of Example 9. In certain of those aspects, the in vitro solubility of the sulfasalazine is at least 1200 µg/ml or at least 2300 µg/ml. In certain embodiments, the application provides methods for treating neuropathic pain in a patient comprising orally administering to the patient a pharmaceutical composition comprising a therapeutically effective amount of sulfasalazine and a pharmaceutically acceptable excipient, wherein the in vitro solubility of the sulfasalazine is about 500 µg/ml, about 1200 µg/ml or about 2300 µg/ml at a pH of 5.5 as determined in Example 9. In some embodiments, there are provided methods for treating a patient with neuropathic pain comprising orally administering to the patient a pharmaceutical composition comprising a therapeutically effective amount of essentially amorphous sulfasalazine and a pharmaceutically acceptable excipient, wherein the in vitro solubility of the sulfasalazine is between about 500 µg/ml and about 11,500 µg/ml, inclusive. In certain of those embodiments, the in vitro solubility of the sulfasalazine is between about 500 µg/ml and about 2500 µg/ml, inclusive. In another embodiment, the in vitro solubility of the sulfasalazine is between about 2300 µg/ml and about 7,500 µg/ml, inclusive. In other of those embodiments, the in vitro solubility of the sulfasalazine is between about 2300 µg/ml and about 11,500 µg/ml, inclusive. In another aspect of the method, the pharmaceutical composition comprises a pharmaceutically acceptable polymer. In certain of those embodiments, the pharmaceutically acceptable polymer is a pyrrolidone polymer. In another aspect of the method, the pyrrolidone polymer is selected from polyvinylpyrrolidone, vinylpyrrolidone-vinyl acetate and crospovidone. In yet another aspect of the method, the pyrrolidone polymer is PVP VA64. In another aspect of the above method, the ratio of the sulfasalazine to PVP VA64 in the pharmaceutical composition is about 20:80 wt/wt to 30:70 wt/wt and wherein the sulfasalazine dispersed in the polymer is in an amorphous form. In another aspect, the ratio of sulfasalazine to PVP VA64 is about 25:75 wt/wt. In some of the embodiments in this paragraph, the neuropathic pain results from painful diabetic neuropathy. In certain embodiments, the neuropathic pain manifests as dysesthesia. In certain embodiments, the neuropathic pain manifests as allodynia. In certain embodiments described in this paragraph, the pharmaceutical composition is one of the pharmaceutical compositions provided by the present application. In certain of those embodiments, the pharmaceutical composition is in an oral dosage form or in a spray dried dispersion form.

In other embodiments, there are provided methods for treating a neurodegenerative disease or disorder in a patient comprising orally administering to the patient a pharmaceutical composition comprising a therapeutically effective amount of sulfasalazine and a pharmaceutically acceptable excipient, wherein the pharmaceutical composition is formulated such that the in vitro solubility of the sulfasalazine is at least 500 µg/ml, at least 1200 µg/ml, or at least 2300 µg/ml at a pH of 5.5 as determined as in Example 9. In other embodiments, there are provided methods for treating a neurodegenerative disease or disorder in a patient comprising orally administering to the patient a pharmaceutical composition comprising a therapeutically effective amount of sulfasalazine and a pharmaceutically acceptable excipient, wherein the pharmaceutical composition is formulated such that the in vitro solubility of the sulfasalazine is about 500 µg/ml, about 1200 µg/ml, or about 2300 µg/ml at a pH of 5.5 as determined as in Example 9. In other embodiments, there are provided methods for treating a neurodegenerative disease or disorder in a patient comprising orally administering to the patient a pharmaceutical composition comprising a therapeutically effective amount of sulfasalazine and a pharmaceutically acceptable excipient, wherein the pharmaceutical composition is formulated such that the in vitro solubility of the sulfasalazine is between about 500 µg/ml and about 11,500 µg/ml, inclusive, at a pH of 5.5 as determined as in Example 9. In another embodiment, the in vitro solubility of the sulfasalazine is between about 500 µg/ml and about 7,500 µg/ml, inclusive, at a pH of 5.5 as determined as in Example 9. In certain of those embodiments, the pharmaceutical composition is formulated such that the in vitro solubility of the sulfasalazine is between about 500 µg/ml and about 2500 µg/ml, inclusive, at a pH of 5.5 as determined as in Example 9. In other of those embodiments, the pharmaceutical composition is formulated such that the in vitro solubility of the sulfasalazine is between about 2300 µg/ml and about 11,500 µg/ml, inclusive, at a pH of 5.5 as determined as in Example 9. In certain embodiments described in this paragraph, the pharmaceutical composition is one of the pharmaceutical compositions provided by the present application. In certain of those embodiments, the pharmaceutical composition is in an oral dosage form or in a spray dried dispersion form. In certain embodiments in this paragraph, the neurodegenerative disease is selected from Parkinson's disease, Alzheimer's disease, epilepsy, traumatic brain injury, Huntington's disease, ischemic stroke, Rett Syndrome, Frontotemporal Dementia, HIV-associated Dementia, Tuberous Sclerosis and Alexander disease.

In other embodiments, there are provided methods for treating a neurodegenerative disease or disorder in a patient comprising orally administering to the patient a pharmaceutical composition comprising a therapeutically effective amount of sulfasalazine and a pharmaceutically acceptable excipient, wherein the pharmaceutical composition is formulated such that the in vitro solubility of the sulfasalazine at a pH of 5.5 as determined as in Example 9 is at least 2 times or 5 times higher than the in vitro solubility of crystalline sulfasalazine at a pH of 5.5. In certain of those embodiments, the in vitro solubility of the sulfasalazine at a pH of 5.5 as determined as in Example 9 is at least 8.8 times higher than the in vitro solubility of crystalline sulfasalazine at a pH of 5.5. In other embodiments, there are provided methods for treating a neurodegenerative disease or disorder in a patient comprising orally administering to the patient a pharmaceutical composition comprising a therapeutically effective amount of sulfasalazine and a pharmaceutically acceptable excipient, wherein the pharmaceutical composition is formulated such that the in vitro solubility of the sulfasalazine at a pH of 5.5 as determined as in Example 9 is between about 2 times and about 44 times, inclusive, higher than the in vitro solubility of crystalline sulfasalazine at a pH of 5.5. In certain of those embodiments, the pharmaceutical composition is formulated such that the in vitro solubility of the sulfasalazine at a pH of 5.5 as determined as in Example 9 is between about 2 times and about 8.8 times, inclusive, higher than the in vitro solubility of crystalline sulfasalazine at a pH of 5.5. In certain other embodiments, the pharmaceutical composition is formulated such that the in vitro solubility of the sulfasalazine at a pH of 5.5 as determined as in Example 9 is between about 8.8 times and about 44 times, inclusive, higher than the in vitro solubility of crystalline sulfasalazine at a pH of 5.5. In certain embodiments described in this paragraph, the pharmaceutical composition is one of the pharmaceutical compositions provided by the present application. In certain of those embodiments, the pharmaceutical composition is in an oral dosage form or in a spray dried dispersion form. In certain embodiments in this paragraph, the neurodegenerative disease is selected from Parkinson's disease, Alzheimer's disease, epilepsy, traumatic brain injury, Huntington's disease, ischemic stroke, Rett Syndrome, Frontotemporal Dementia, HIV-associated Dementia, Tuberous Sclerosis and Alexander disease.

In some embodiments, the present invention provides methods for treating a patient with a neurodegenerative disease or disorder in a patient comprising orally administering to the patient a pharmaceutical composition comprising a therapeutically effective amount of sulfasalazine and a pharmaceutical acceptable excipient, wherein the sulfasalazine is in an essentially amorphous form. In one aspect of the method, the in vitro solubility of the sulfasalazine from the composition is at least 500 µg/ml at a pH of 5.5 when measured by the method of Example 9. In another aspect of the invention, the in vitro solubility of the sulfasalazine from the composition is at least 1200 µg/ml or at least 2300 µg/ml. In other aspects of the invention, the in vitro solubility of the sulfasalazine from the composition is between about 500 µg/ml and about 11,500 µg/ml, inclusive. In another aspect, the in vitro solubility of the sulfasalazine from the composition is between about 500 µg/ml and about 7,500 µg/ml, inclusive. In other aspects of the invention, the in vitro solubility of the sulfasalazine from the composition is between about 500 µg/ml and about 2500 µg/ml. In other aspects of the invention, the in vitro solubility of the sulfasalazine from the composition is between about 2300 µg/ml and about 11,500 µg/ml. In another aspect of the method, the pharmaceutical composition comprises a pharmaceutically acceptable polymer. In certain of those embodiments, the pharmaceutically acceptable polymer is a pyrrolidone polymer. In another aspect of the method, the pyrrolidone polymer is selected from polyvinylpyrrolidone, vinylpyrrolidone-vinyl acetate and crospovidone. In yet another aspect of the method, the pyrrolidone polymer is PVP VA64. In another aspect of the above method, the ratio of the sulfasalazine to PVP VA64 in the pharmaceutical composition is about 20:80 wt/wt to 30:70 wt/wt. In another aspect, the ratio of sulfasalazine to PVP VA64 is about 25:75 wt/wt. In certain embodiments in this paragraph, the pharmaceutical composition is one of the pharmaceutical compositions provided by the present application. In certain of those embodiments, the pharmaceutical composition is in an oral dosage form or in a spray dried dispersion form. In certain embodiments in this paragraph, the neurodegenerative disease is selected from Parkinson's disease, Alzheimer's disease, epilepsy, traumatic brain injury, Huntington's disease, ischemic stroke, Rett Syndrome, Frontotemporal Dementia, HIV-associated Dementia, Tuberous Sclerosis and Alexander disease.

In other embodiments, there are provided methods for treating a patient with P-MS comprising orally administering to the patient a pharmaceutical composition comprising a therapeutically effective amount of sulfasalazine and PVP VA64; wherein the ratio of sulfasalazine to PVP VA64 is about 20:80 wt/wt to 30:70 wt/wt. In certain of those embodiments, the sulfasalazine dispersed in the polymer is in an essentially amorphous form. In certain of those embodiments, the sulfasalazine is dispersed in the polymer is in an amorphous form. In certain of the embodiments in this paragraph, the ratio of sulfasalazine to PVP VA64 is about 25:75 wt/wt. In certain embodiments in this paragraph, the pharmaceutical composition further comprises a pharmaceutically acceptable excipient.

In certain embodiments, methods are provided for treating a patient with P-MS comprising orally administering to the patient a pharmaceutical composition comprising sulfasalazine and HPMCAS, wherein the ratio of the sulfasalazine to HPMCAS in the composition is about 20:80 wt/wt to 30:70 wt/wt and wherein the sulfasalazine dispersed in the polymer is in an essentially amorphous form. In certain of those embodiments, the sulfasalazine is dispersed in the polymer is in an amorphous form. In certain embodiments, the ratio of sulfasalazine to HPMCAS is about 25:75 wt/wt. In certain embodiments in this paragraph, the pharmaceutical composition further comprises a pharmaceutically acceptable excipient.

In other embodiments, there are provided methods for treating a patient with ALS comprising orally administering to the patient a pharmaceutical composition comprising a therapeutically effective amount of sulfasalazine and PVP VA64; wherein the ratio of sulfasalazine to PVP VA64 is about 20:80 wt/wt to 30:70 wt/wt and wherein the sulfasalazine dispersed in the polymer is in an essentially amorphous form. In certain of those embodiments, the sulfasalazine is dispersed in the polymer is in an amorphous form. In certain embodiments, the ratio of sulfasalazine to PVP VA64 is about 25:75 wt/wt. In certain embodiments in this paragraph, the pharmaceutical composition further comprises a pharmaceutically acceptable excipient.

In certain embodiments, methods are provided for treating a patient with ALS comprising orally administering to the patient a pharmaceutical composition comprising sulfasalazine and HPMCAS; wherein the ratio of the sulfasalazine to HPMCAS in the composition is about 20:80 wt/wt to 30:70 wt/wt and wherein the sulfasalazine dispersed in the polymer is in an essentially amorphous form. In certain of those embodiments, the sulfasalazine is dispersed in the polymer is in an amorphous form. In certain embodiments, the ratio of sulfasalazine to HPMCAS is about 25:75 wt/wt. In certain embodiments in this paragraph, the pharmaceutical composition further comprises a pharmaceutically acceptable excipient.

In other embodiments, there are provided methods for treating a patient with neuropathic pain comprising orally administering to the patient a pharmaceutical composition comprising a therapeutically effective amount of sulfasalazine and PVP VA64; wherein the ratio of sulfasalazine to PVP VA64 is about 20:80 wt/wt to 30:70 wt/wt; wherein the sulfasalazine dispersed in the polymer is in an essentially amorphous form. In certain of those embodiments, the sulfasalazine is dispersed in the polymer is in an amorphous form. In certain embodiments, the ratio of sulfasalazine to PVP VA64 is about 25:75 wt/wt. In some of the embodiments in this paragraph, the neuropathic pain is diabetic neuropathic pain. In certain embodiments, the neuropathic pain manifests as dysesthesia. In certain embodiments, the neuropathic pain manifests as allodynia. In certain embodiments in this paragraph, the pharmaceutical composition further comprises a pharmaceutically acceptable excipient.

In certain embodiments, methods are provided for treating a patient with neuropathic pain comprising orally administering to the patient a pharmaceutical composition comprising sulfasalazine and HPMCAS; wherein the ratio of the sulfasalazine to HPMCAS in the composition is about 20:80 wt/wt to 30:70 wt/wt and wherein the sulfasalazine dispersed in the polymer is in an essentially amorphous form. In certain of those embodiments, the sulfasalazine is dispersed in the polymer is in an amorphous form. In certain embodiments, the ratio of sulfasalazine to HPMCAS is about 25:75 wt/wt. In some of the embodiments in this paragraph, the neuropathic pain results from painful diabetic neuropathy. In certain embodiments, the neuropathic pain manifests as dysesthesia. In certain embodiments, the neuropathic pain manifests as allodynia. In certain embodiments in this paragraph, the pharmaceutical composition further comprises a pharmaceutically acceptable excipient.

In other embodiments, there are provided methods for treating a neurodegenerative disease or disorder in a patient comprising orally administering to the patient a pharmaceutical composition comprising a therapeutically effective amount of sulfasalazine and PVP VA64; wherein the ratio of sulfasalazine to PVP VA64 is about 20:80 wt/wt to 30:70 wt/wt and wherein the sulfasalazine dispersed in the polymer is in an essentially amorphous form. In certain of those embodiments, the sulfasalazine is dispersed in the polymer is in an amorphous form. In certain of those embodiments, the ratio of sulfasalazine to PVP VA64 is about 25:75 wt/wt. In certain embodiments in this paragraph, the pharmaceutical composition further comprises a pharmaceutically acceptable excipient. In certain embodiments in this paragraph, the neurodegenerative disease is selected from Parkinson's disease, Alzheimer's disease, epilepsy, traumatic brain injury, Huntington's disease, ischemic stroke, Rett Syndrome, Frontotemporal Dementia, HIV-associated Dementia, Tuberous Sclerosis and Alexander disease.

In other embodiments, there are provided methods for treating a neurodegenerative disease or disorder in a patient comprising orally administering to the patient a pharmaceutical compositions comprising sulfasalazine and HPMCAS wherein the ratio of the sulfasalazine to HPMCAS in the composition is about 20:80 wt/wt to 30:70 wt/wt. In certain of those embodiments, the sulfasalazine is dispersed in an essentially amorphous form. In certain of those embodiments, the sulfasalazine is dispersed in the polymer is in an amorphous form. In certain of those embodiments, the ratio of sulfasalazine to HPMCAS is about 25:75 wt/wt. In certain embodiments in this paragraph, the pharmaceutical composition further comprises a pharmaceutically acceptable excipient. In certain embodiments in this paragraph, the neurodegenerative disease is selected from Parkinson's disease, Alzheimer's disease, epilepsy, traumatic brain injury, Huntington's disease, ischemic stroke, Rett Syndrome, Frontotemporal Dementia, HIV-associated Dementia, Tuberous Sclerosis and Alexander disease.

In certain embodiments, methods are provided for lowering excessive levels of glutamate in a patient with a neurodegenerative disease comprising orally administering to the patient a pharmaceutical composition comprising a therapeutically effective amount of sulfasalazine and a pyrrolidone polymer, wherein the ratio of the sulfasalazine to the pyrrolidone polymer in the composition is about 20:80 wt/wt to 30:70 wt/wt and wherein the sulfasalazine dispersed in the polymer is in an essentially amorphous form. In certain of those embodiments, the sulfasalazine is dispersed in the polymer is in an amorphous form. In certain of those embodiments, the ratio of sulfasalazine to pyrrolidone polymer is about 25:75 wt/wt. In certain embodiments in this paragraph, the pharmaceutical composition further comprises a pharmaceutically acceptable excipient.

In one aspect of each of the above embodiments, the neurodegenerative disease or disorder is selected from the group consisting of epilepsy, stroke or traumatic brain injury. In another aspect, the neurodegenerative disease or disorder is Parkinson's disease (PD), Alzheimer's disease (AD), or Huntington's. In another aspect of each of the above embodiments, the neurodegenerative disease or disorder is progressive MS (P-MS). In another aspect of each of the above embodiments, the neurodegenerative disease or disorder is amyotrophic lateral sclerosis (ALS). In another aspect of each of the above embodiments, the neurodegenerative disease or disorder is neuropathic pain. In another aspect of each of the above embodiments, the sulfasalazine is amorphous sulfasalazine. In another aspect of each of the above embodiments, the in vitro solubility of the sulfasalazine is at least 500 µg/ml or at least 1200 µg/ml at a pH of 5.5 as determined as in Example 9. In another aspect of each of the above embodiments, the methods comprise the use of one of the above-cited pharmaceutical compositions comprising sulfasalazine.

Combination Treatment Methods

In certain aspects of the invention, a patient with ALS is also administered riluzole in addition to a pharmaceutical composition of the invention. In certain of these embodiments, the riluzole is administered to the patient concurrently with the pharmaceutical composition. In certain embodiments, the riluzole is administered to the patient at different times than the pharmaceutical composition.

In certain aspects of the invention, a patient with P-MS is also administered Mitoxantrone, Gilenya, Masitinib, Siponimod, Tcelna, Tecfidera, Lemtrada, Laquinimod, Daclizumab, Ocrelizumab, Cladribine, Daclizumab, Tysabri, Campath, Rituximab, Fingolimod, Azathioprine or Ibudilast in addition to a pharmaceutical composition of the invention. In certain of these embodiments, the Mitoxantrone, Gilenya, Masitinib, Siponimod, Tcelna, Tecfidera, Lemtrada, Laquinimod, Daclizumab, Ocrelizumab, Cladribine, Daclizumab, Tysabri, Campath, Rituximab, Fingolimod, Azathioprine or Ibudilast is administered to the patient concurrently with the pharmaceutical composition. In certain embodiments, the Mitoxantrone, Gilenya, Masitinib, Siponimod, Tcelna, Tecfidera, Lemtrada, Laquinimod, Daclizumab, Ocrelizumab, Cladribine, Daclizumab, Tysabri, Campath, Rituximab, Fingolimod, Azathioprine or Ibudilast is administered to the patient at different times than the pharmaceutical composition.

Dosing Regimens for the Treatment of P-MS

In certain embodiments, the present invention provides methods of treating P-MS in patients by administering a therapeutically effective amount of a system $x_c^-$ inhibitor to such patients. In certain of those embodiments, the system $x_c^-$ inhibitor is sulfasalazine. Previous work has tested use of sulfasalazine for treatment of multiple sclerosis (both RR-MS and P-MS) in humans, e.g. Noseworthy et al, *Neurology* 15: 1342-1352 (1998). In this work, patients were treated with 2 grams of sulfasalazine per day, the typical maintenance dose used for non-CNS diseases, such as rheumatoid arthritis, e.g. Khan et al, *Gut* 21:232-240 (1980). Sulfasalazine did not slow disease progression in the RR-MS sub-group. In the P-MS subgroup, patients treated with sulfasalazine had a statistically significant reduction in their accumulation of disability, which the authors attributed to a "real treatment effect." See id. at p. 1346. However, no further clinical trials of sulfasalazine for the treatment of either P-MS or RR-MS have been performed. Other previous work demonstrated that a 2 g oral dose of sulfasalazine administered to humans produced plasma levels above 10 µg/ml that were maintained for only approximately 7 hours in people with the ABCG2 genotype (421C/C) (see Yamasaki et al, *Clin. Pharmac. Therap.* 84: 95-103 (2007)), which is the predominant ABCG2 genotype in European Caucasian and African American populations (77%-90%) see, e.g., de Jong et al, *Clin. Cancer Res.* 10:5889-5894 (2004). Prior work had also shown that the anti-epileptic effect of sulfasalazine administered to a mouse model at a dose of approximately 260-320 mg/kg intraperitoneal ("IP") disappears by three hours after administration (see Buckingham et al, *Nat Med.* 17:1269-1274 (2011)). As experiments described herein indicate that the plasma level of sulfasalazine in a mouse administered a 200 mg/kg dose IP of sulfasalazine (approximately 30-60% lower dose than the Buckingham study) is about 6 µg/ml three hours after administration (see Example 4), the inventors determined that a plasma level of sulfasalazine of at least approximately 8-10 µg/ml (adjusted for dose differences) is needed is needed for a therapeutic effect by sulfasalazine on the system $x_c^-$ in the CNS compartment. Based on this, the inventors hypothesize that the P-MS patients treated with sulfasalazine in the Noseworthy study were under-dosed. Thus, the invention also provides methods of treating P-MS with sulfasalazine using improved dosing regimens and formulations.

In certain embodiments, the present invention provides methods for treating P-MS in a patient comprising administering to the patient a pharmaceutical composition comprising sulfasalazine, wherein the sulfasalazine is dosed at levels and/or frequencies sufficient to produce improved therapeutic effects. In certain embodiments, methods are provided for treating a patient with P-MS comprising orally administering to the patient a pharmaceutical composition comprising sulfasalazine and a pharmaceutically acceptable excipient, wherein the dose of the pharmaceutical composition is sufficient to maintain a plasma level of sulfasalazine in the patient effective for treating P-MS for at least 14 total hours a day. In certain of those embodiments, a plasma level of sulfasalazine in the patient effective for treating P-MS is maintained for between 21 and 24, inclusive, total hours a day. In certain of those embodiments, a plasma level of sulfasalazine in the patient effective for treating P-MS is maintained for 24 hours a day.

In certain embodiments, methods are provided for treating a patient with P-MS comprising orally administering to the patient a pharmaceutical composition comprising sulfasalazine and a pharmaceutically acceptable excipient, wherein the dose of the pharmaceutical composition is sufficient to maintain a plasma level of sulfasalazine of at least 8 µg/ml for at least 14 total hours a day. In certain of those embodiments, a plasma level of sulfasalazine of at least 8 µg/ml is maintained for between 21 and 24, inclusive, total hours a day. In certain of those embodiments, a plasma level of sulfasalazine of at least 8 µg/ml is maintained for 24 hours a day. In certain embodiments in this paragraph, the dose of the pharmaceutical composition is sufficient to maintain a plasma level of sulfasalazine of between about 8 µg/ml and about 30 µg/ml, inclusive, or between about 8 µg/ml and about 16 µg/ml, inclusive, or between about 10 µg/ml and about 16 µg/ml, inclusive, for the given amount of time.

In certain embodiments, the present invention provides methods for treating a patient with P-MS comprising administering to the patient a pharmaceutical composition comprising sulfasalazine and a pharmaceutically acceptable excipient, wherein the dose of the pharmaceutical composition is sufficient to produce a plasma level of sulfasalazine in the patient of at least 8 µg/ml for the entire dosing interval. For the purposes of this application, the condition "for the entire dosing interval" will be considered to be met if the level of the sulfasalazine is at or above the designated level at the end of the dosing interval (but before any next administration of the sulfasalazine). In certain of those embodiments, the dose of the pharmaceutical composition is sufficient to produce a plasma level of sulfasalazine in the patient of at least 10 µg/ml for the entire dosing interval. In certain other embodiments, the dose of the pharmaceutical composition is sufficient to produce a plasma level of sulfasalazine in the patient of at least 16 µg/ml for the entire dosing interval. In certain embodiments, the present invention provides methods for treating a patient with P-MS comprising administering to the patient a pharmaceutical composition comprising sulfasalazine and a pharmaceutically acceptable excipient, wherein the dose of the pharmaceutical composition is sufficient to produce a plasma level of sulfasalazine in the patient of between about 8 µg/ml and about 30 µg/ml, inclusive, for the entire dosing interval. In certain of those embodiments, the dose of the pharmaceutical composition is sufficient to produce a plasma level of sulfasalazine in the patient of between about 10 µg/ml and about 30 µg/ml, inclusive, for the entire dosing interval. In certain other embodiments, the dose of the pharmaceutical composition is sufficient to produce a plasma level of sulfasalazine in the patient of between about 8 µg/ml and about 16 µg/ml, inclusive, for the entire dosing interval. In certain other embodiments, the dose of the pharmaceutical composition is sufficient to produce a plasma level of sulfasalazine in the patient of between about 8 µg/ml and about 12 µg/ml, inclusive, for the entire dosing interval. In certain embodiments of this paragraph, the sulfasalazine is in an essentially amorphous form.

One way to increase plasma levels of sulfasalazine is to administer higher daily doses of the standard formulation of sulfasalazine to patients. Previous work has demonstrated that, in humans, plasma levels of sulfasalazine are proportional to the oral dose, e.g. Khan et al, *Gut* 21:232-240 (1980). In certain embodiments, the present invention provides methods for treating a patient with P-MS comprising orally administering to the patient a pharmaceutical composition comprising sulfasalazine and a pharmaceutically acceptable excipient, wherein the pharmaceutical composition is a standard formulation of sulfasalazine and the total daily dose of sulfasalazine is between about 2.5 grams and about 8 grams, inclusive. In certain of those embodiments, the total daily dose of sulfasalazine is between about 3 grams and about 5 grams, inclusive. In certain embodiments, the present invention provides methods for treating a patient with P-MS comprising orally administering to the patient a pharmaceutical composition comprising sulfasalazine and a pharmaceutically acceptable excipient, wherein the pharmaceutical composition is a standard formulation of sulfasalazine and the total daily dose of sulfasalazine is about 3 grams, about 4 grams, or about 5 grams.

In certain embodiments, the present invention provides methods for treating a patient with P-MS comprising orally administering to the patient a pharmaceutical composition comprising sulfasalazine and a pharmaceutically acceptable excipient, wherein (a) the pharmaceutical composition is a standard formulation of sulfasalazine, (b) the dose at each dosing time point is not more than about 4 grams of sulfasalazine, (c) there are at least two dosing time points in a day, and (d) the total daily dose is between about 2.5 grams and about 8 grams, inclusive. In certain of those embodiments, there are two dosing time points in a day. In certain of those embodiments, there are three dosing time points in a day. In certain other embodiments, there are four dosing time points in a day.

In certain embodiments, methods are provided for treating P-MS in a patient comprising orally administering to the patient a pharmaceutical composition comprising sulfasalazine and a pharmaceutically acceptable excipient, wherein the pharmaceutical composition is a standard formulation of sulfasalazine and the dose of sulfasalazine is between about 2.5 grams and about 6 grams, inclusive, and is administered once a day. In certain of those embodiments, the dose of sulfasalazine is between about 3 grams and about 5 grams, inclusive, and is administered once a day. In certain of those embodiments, the dose of sulfasalazine is about 3 grams, about 4 grams, or about 5 grams and is administered once a day.

Treatment of Diseases and Disorders Other than Neurodegenerative Diseases and Disorders In other embodiments, there is provided a method for treating diseases where sulfasalazine is currently used clinically and is believed to act systemically, including rheumatoid arthritis and ankylosing spondylitis, wherein such method comprises administering a composition of the invention comprising sulfasalazine in which the solubility and/or the bioavailability of the sulfasalazine is increased. In rheumatoid arthritis, the typical maintenance dose of sulfasalazine is 2 g/day. Higher doses have been shown to result in greater efficacy, but, unfortunately, the higher doses of sulfasalazine also result in a higher incidence of toxicity, e.g. Khan et al, *Gut* 21:232-240 (1980). By increasing the solubility and/or the bioavailability of the sulfasalazine, the present invention provides a method of increasing the therapeutic dose of sulfasalazine without an increase in the toxicity.

The present invention provides methods for treating a patient with rheumatoid arthritis and/or ankylosing spondylitis comprising orally administering to the patient a pharmaceutical composition comprising a therapeutically effective amount of sulfasalazine and a pharmaceutically acceptable excipient, wherein the sulfasalazine is in an essentially amorphous form. In certain of those embodiments, the pharmaceutical composition is one of the pharmaceutical compositions provided by the present application. In certain of those embodiments, the pharmaceutical composition is in an oral dosage form or in a spray dried dispersion form. In certain embodiments, the pharmaceutical composition comprises a pharmaceutically acceptable polymer. In certain of those embodiments, the pharmaceutically acceptable polymer is a pyrrolidone polymer. In certain of those embodiments, the pyrrolidone polymer is selected from the group consisting of polyvinylpyrrolidone, vinylpyrrolidone-vinyl acetate and crospovidone. In certain embodiments, the pyrrolidone polymer is PVP VA64. In certain of those embodiments, the ratio of the sulfasalazine to PVP VA64 in the pharmaceutical composition is about 20:80 wt/wt to 30:70 wt/wt. In certain embodiments, the ratio of sulfasalazine to PVP VA64 is about 25:75 wt/wt.

In certain embodiments, there are provided methods for treating rheumatoid arthritis and/or ankylosing spondylitis in a patient comprising orally administering to the patient a pharmaceutical composition comprising a therapeutically effective amount of sulfasalazine and a pharmaceutically acceptable excipient, wherein the pharmaceutical composition is formulated such that oral administration of the formulated pharmaceutical composition to a rat results in a plasma level of sulfasalazine thirty minutes after such administration that is at least 25%, at least 50%, at least 100%, at least 150%, at least 200%, at least 250% or at least 300% higher than the plasma level of sulfasalazine thirty minutes after administration of the same dose level of crystalline sulfasalazine to a rat as determined by the method of Example 10. In certain embodiments, there are provided methods for treating rheumatoid arthritis and/or ankylosing spondylitis in a patient comprising orally administering to the patient a pharmaceutical composition comprising a therapeutically effective amount of sulfasalazine and a pharmaceutically acceptable excipient, wherein the pharmaceutical composition is formulated such that oral administration of the formulated pharmaceutical composition to a rat results in a plasma level of sulfasalazine thirty minutes after such administration that is about 25%, about 50%, about 100%, about 150%, about 200%, about 250% or about 300% higher than the plasma level of sulfasalazine thirty minutes after administration of the same dose level of crystalline sulfasalazine to a rat as determined by the method of Example 10. In certain embodiments, the pharmaceutical composition is formulated such that oral administration of the formulated pharmaceutical composition to a rat results in a plasma level of sulfasalazine thirty minutes after such administration that is between about 25% and about 500%, inclusive, higher than the plasma level of sulfasalazine thirty minutes after administration of the same dose level of crystalline sulfasalazine to a rat as determined by the method of Example 10. In certain of those embodiments, the pharmaceutical composition is formulated such that oral administration of the formulated pharmaceutical composition to a rat results in a plasma level of sulfasalazine thirty minutes after such administration that is between about 75% and about 300%, inclusive, higher than the plasma level of sulfasalazine thirty minutes after administration of the same dose level of crystalline sulfasalazine to a rat as determined by the method of Example 10. In certain other of those embodiments, the pharmaceutical composition is formulated such that oral administration of the formulated pharmaceutical composition to a rat results in a plasma level of sulfasalazine thirty minutes after such administration that is between about 100% and about 200%, inclusive, higher than the plasma level of sulfasalazine thirty minutes after administration of the same dose level of crystalline sulfasalazine to a rat as determined by the method of Example 10. In certain embodiments described in this paragraph, the pharmaceutical composition is one of the pharmaceutical compositions provided by the present application. In certain of those embodiments, the pharmaceutical composition is in an oral dosage form or in a spray dried dispersion form.

In certain embodiments, methods are provided for treating a patient with rheumatoid arthritis and/or ankylosing spondylitis comprising orally administering to the patient a pharmaceutical composition comprising a therapeutically effective amount of sulfasalazine and a pharmaceutically acceptable excipient, wherein the pharmaceutical composition comprises PVP VA 64 and the ratio of the sulfasalazine to PVP VA64 in the pharmaceutical composition is about 20:80 wt/wt to 30:70 wt/wt. In certain of those embodiments, the ratio of sulfasalazine to PVP VA64 is about 25:75 wt/wt. In certain of the above embodiments, wherein the sulfasalazine dispersed in the polymer is in an essentially amorphous form.

In certain embodiments, methods are provided for treating a patient with rheumatoid arthritis and/or ankylosing spondylitis comprising orally administering to the patient a pharmaceutical composition comprising a therapeutically effective amount of sulfasalazine and HPMCAS, wherein the ratio of the sulfasalazine to HPMCAS in the composition is about 20:80 wt/wt to 30:70 wt/wt. In certain of those embodiments, the ratio of sulfasalazine to HPMCAS is about 25:75 wt/wt. In certain of those embodiments, the sulfasalazine is dispersed in an essentially amorphous form.

In certain embodiments, the application provides methods for treating rheumatoid arthritis and/or ankylosing spondylitis in a patient comprising orally administering to the patient a pharmaceutical composition comprising a therapeutically effective amount of sulfasalazine and a pharmaceutically acceptable excipient, wherein the pharmaceutical composition is formulated such that the in vitro solubility of the sulfasalazine is at least 500 µg/ml, at least 1200 µg/ml or at least 2300 µg/ml at a pH of 5.5 determined as in Example 9. In certain embodiments, the application provides methods for treating rheumatoid arthritis and/or ankylosing spondylitis in a patient comprising orally administering to the patient a pharmaceutical composition comprising a therapeutically effective amount of sulfasalazine and a pharmaceutically acceptable excipient, wherein the pharmaceutical composition is formulated such that the in vitro solubility of the sulfasalazine is about 500 µg/ml, about 1200 µg/ml or about 2300 µg/ml at a pH of 5.5 as determined in Example 9. In certain embodiments, the application provides methods for treating rheumatoid arthritis and/or ankylosing spondylitis in a patient comprising orally administering to the patient a pharmaceutical composition comprising a therapeutically effective amount of sulfasalazine and a pharmaceutically acceptable excipient, wherein the pharmaceutical composition is formulated such that the in vitro solubility of the sulfasalazine is between about 500 µg/ml and about 11,500 µg/ml, inclusive, at a pH of 5.5 determined as in Example 9. In certain of those embodiments, the pharmaceutical composition is formulated such that the in vitro solubility of the sulfasalazine is between about 2300 µg/ml and about 11,500 µg/ml, inclusive, at a pH of 5.5 determined as in Example 9. In certain other of those embodiments, the pharmaceutical composition is formulated such that the in vitro solubility of the sulfasalazine is between about 500 µg/ml and about 2500 µg/ml, inclusive, at a pH of 5.5 determined as in Example 9. In certain embodiments described in this paragraph, the pharmaceutical composition is one of the pharmaceutical compositions provided by the present application. In certain of those embodiments, the pharmaceutical composition is in an oral dosage form or in a spray dried dispersion form.

In certain embodiments, methods are provided for treating rheumatoid arthritis and/or ankylosing spondylitis in a patient comprising orally administering to the patient a pharmaceutical composition comprising a therapeutically effective amount of sulfasalazine and a pharmaceutically acceptable excipient, wherein the pharmaceutical composition is formulated such that the in vitro solubility of the sulfasalazine at a pH of 5.5 as determined in Example 9 is at least 2 times higher than the in vitro solubility of crystalline sulfasalazine at a pH of 5.5 by AUC analysis. In certain of those embodiments, the pharmaceutical composition is formulated such that the in vitro solubility of the sulfasalazine at a pH of 5.5 as determined in Example 9 is at least 5 times or at least 8.8 times higher than the in vitro solubility of crystalline sulfasalazine at a pH of 5.5 by AUC analysis. In certain embodiments, methods are provided for treating rheumatoid arthritis and/or ankylosing spondylitis in a patient comprising orally administering to the patient a pharmaceutical composition comprising a therapeutically effective amount of sulfasalazine and a pharmaceutically acceptable excipient, wherein the pharmaceutical composition is formulated such that the in vitro solubility of the sulfasalazine at a pH of 5.5 as determined in Example 9 is about 2 times, about 5 times, or about 8.8 times higher than the in vitro solubility of crystalline sulfasalazine at a pH of 5.5 by AUC analysis. In certain embodiments, methods are provided for treating rheumatoid arthritis and/or ankylosing spondylitis in a patient comprising orally administering to the patient a pharmaceutical composition comprising a therapeutically effective amount of sulfasalazine and a pharmaceutically acceptable excipient, wherein the pharmaceutical composition is formulated such that the in vitro solubility of the sulfasalazine at a pH of 5.5 as determined in Example 9 is between about 2 times and about 44 times, inclusive, higher than the in vitro solubility of crystalline sulfasalazine at a pH of 5.5 by AUC analysis. In certain of those embodiments, the pharmaceutical composition is formulated such that the in vitro solubility of the sulfasalazine at a pH of 5.5 as determined in Example 9 is between about 2 times and about 8.8 times, inclusive, higher than the in vitro solubility of crystalline sulfasalazine at a pH of 5.5 by AUC analysis. In certain of those embodiments, the pharmaceutical composition is formulated such that the in vitro solubility of the sulfasalazine at a pH of 5.5 as determined in Example 9 is between about 8.8 times and about 44 times, inclusive, higher than the in vitro solubility of crystalline sulfasalazine at a pH of 5.5 by AUC analysis. In certain embodiments described in this paragraph, the pharmaceutical composition is one of the pharmaceutical compositions provided by the present application. In certain of those embodiments, the pharmaceutical composition is in an oral dosage form or in a spray dried dispersion form.

In other embodiments, there is provided a method for increasing the bioavailability of sulfasalazine in a mammal, the method comprises orally administering a spray dried dispersion composition comprising a therapeutically effective amount of sulfasalazine and a pyrrolidone polymer, wherein the sulfasalazine dispersed in the polymer is in an essentially amorphous form. In certain of those embodiments, the sulfasalazine is in an amorphous form. In certain of those embodiments, the spray dried dispersion further comprises a pharmaceutically acceptable excipient.

Other System $x_c^-$ Inhibitors

In some embodiments, methods for treating a patient with a neurodegenerative disease or disorder comprising administering to the patient an effective amount of an inhibitor of system $x_c^-$ other than sulfasalazine are provided. In certain of those embodiments, the system $x_c^-$ inhibitor is selected from (S)-4-carboxyphenylglycine, 2-hydroxy-5-((4-(N-pyridin-2-ylsulfamoyl)phenyl)ethynyl)benzoic acid, aminoadipate (AAA),4-(1-(2-(3,5-bis(trifluoromethyl)phenyl)hydrazono)ethyl)-5-(4 (trifluoromethyl)benzyl)isoxazole-3-carboxylic acid, 5-benzyl-4-(1-(2-(3,5-bis(trifluoro-methyl)phenyl)hydrazono)ethyl)isoxazole-3-carboxylic acid and 2-hydroxy-5-[2-[4-[(3-methylpyridin-2-yl)sulfamoyl]phenyl]ethynyl]benzoic acid.

The following embodiments, aspects and variations thereof are exemplary and illustrative are not intended to be limiting in scope.

DESCRIPTIONS OF THE FIGURES

Figure 6:
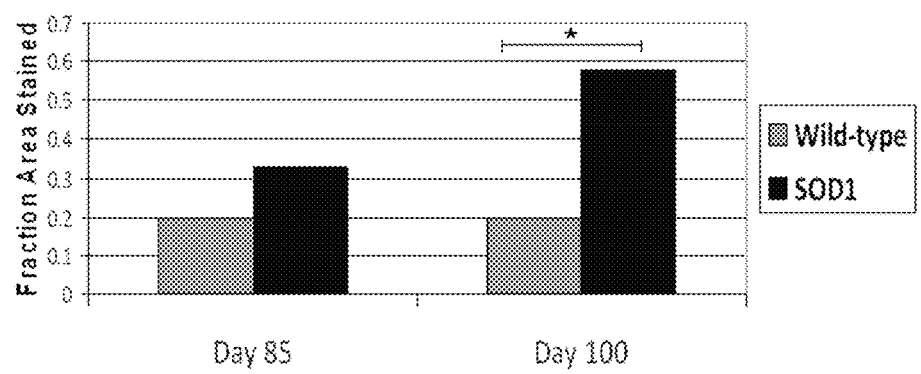

FIG. 6 shows a representative graph of an area fraction analysis comparing xCT expression in day 85 and day 100 mice. The y-axis quantifies the xCT expression in the ventral horn of the combined cervical, thoracic and lumbar spinal cord regions in vehicle treated SOD1 mice and wild-type mice. The symbol '*' indicates the indicated measurement between groups reached a statistical significance of $p<0.05$.

Figure 7:
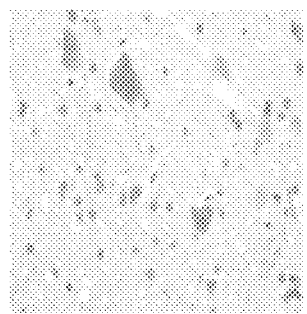
Figure 7:
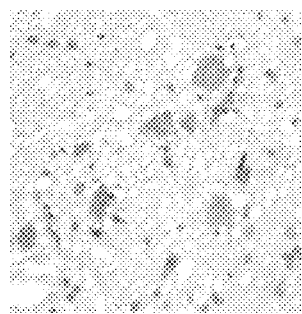
Figure 7:
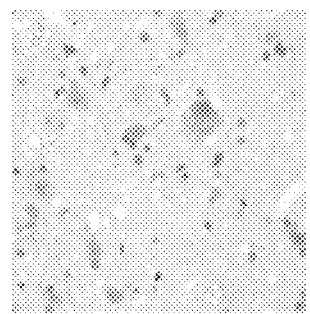

FIG. 7 shows representative images from the ventral horn of the spinal cord from Day 85 mice stained for microglial activation using anti-F4/80 antibody. Activated microglia are stained brown.

Figure 8:
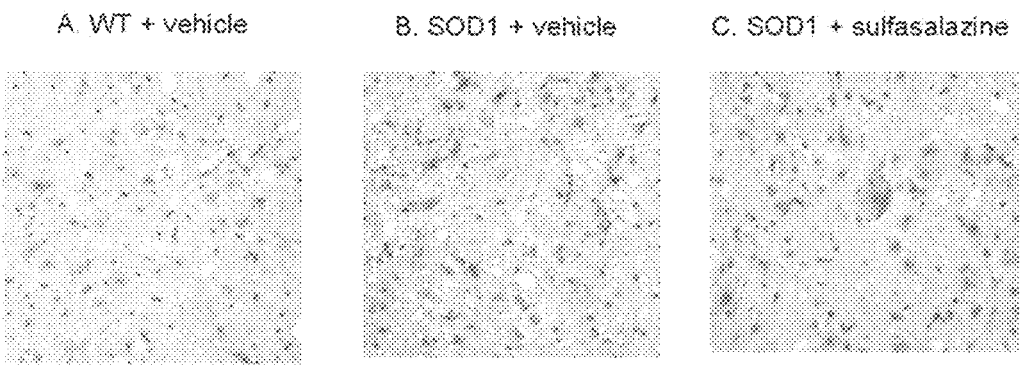

FIG. 8 shows representative samples from Day 100 mice stained for astrocyte activation using anti-GFAP antibody. Activated astrocytes are stained brown.

Figure 9:
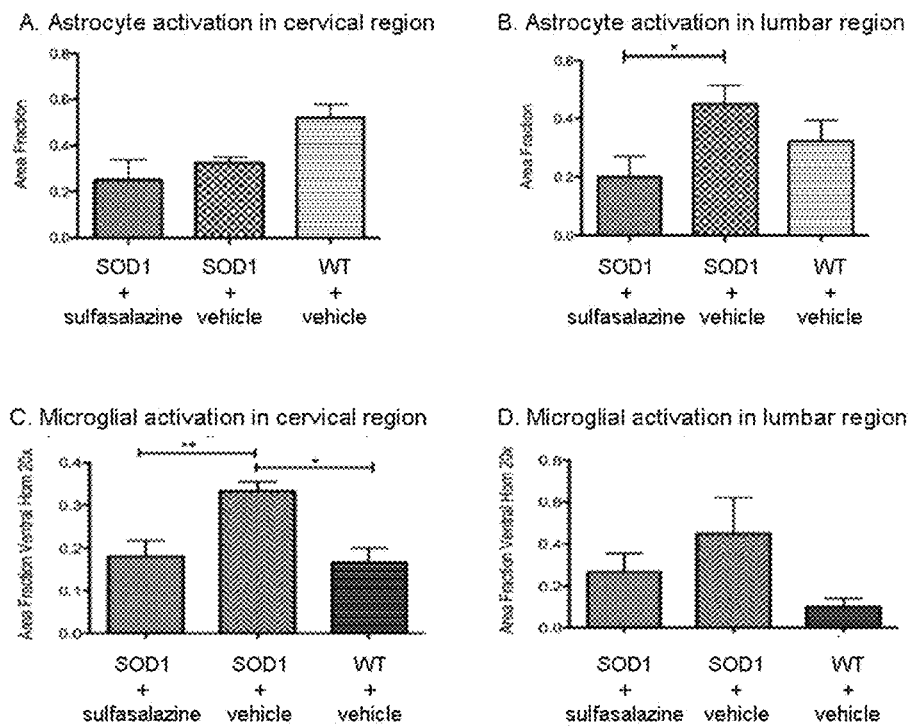

FIG. 9 shows area fraction quantitation of the activated astrocytes and microglial cells in the ventral horn from the cervical and lumbar regions in day 85 mice. Images were analyzed in a blinded fashion and mean area fraction occupied by stain was tabulated. The symbols '*' and '**' indicate the indicated measurement between groups reached a statistical significance of $p<0.05$ and $p<0.01$, respectively.

Figure 10:
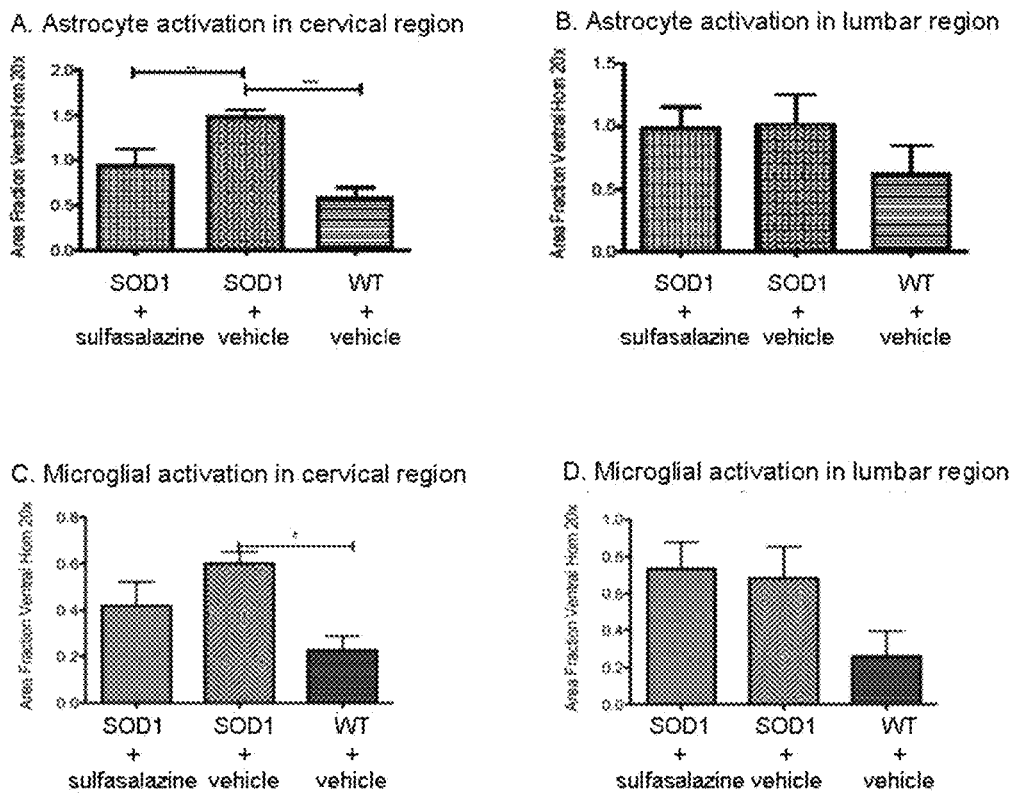

FIG. 10 shows area fraction quantitation of the activated astrocytes and microglial cells in the ventral horn from the cervical and lumbar regions in day 100 mice. The symbols '*', '' and '*' indicate the measurement between groups reached a statistical significance of $p<0.05$, $p<0.01$ and $p<0.001$, respectively.

Figure 11:
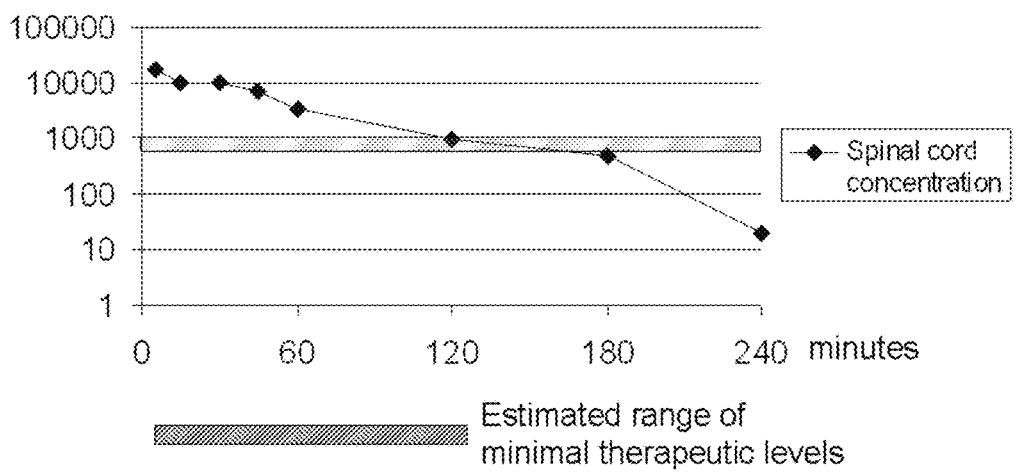

FIG. 11 shows a representative graph of sulfasalazine concentration in the spinal cord of SOD1 mice versus time.

Figure 12:
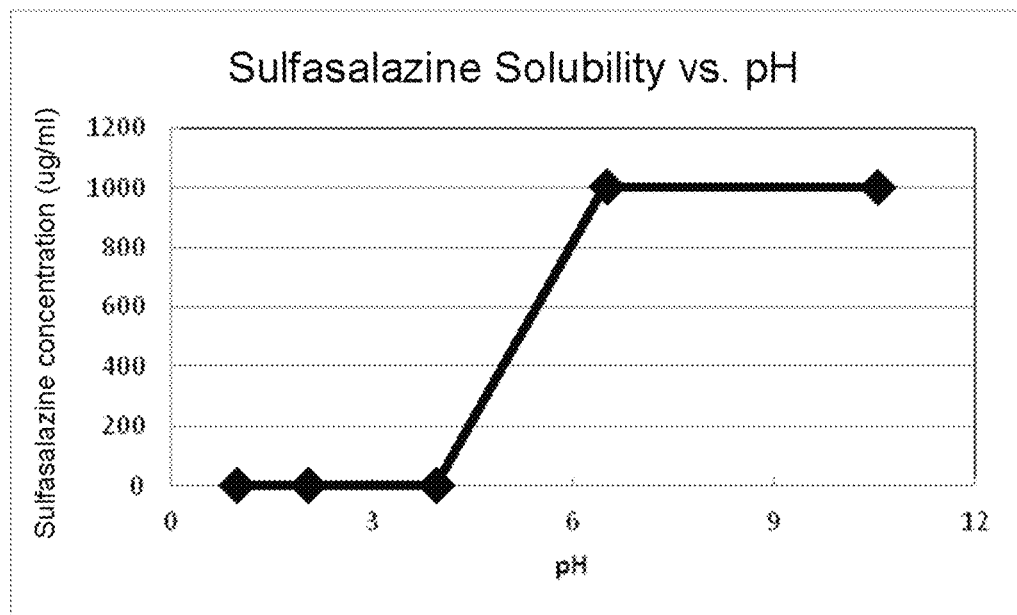

FIG. 12 is a graphical representation of the in vitro solubility of sulfasalazine as a function of pH.

Figure 13:
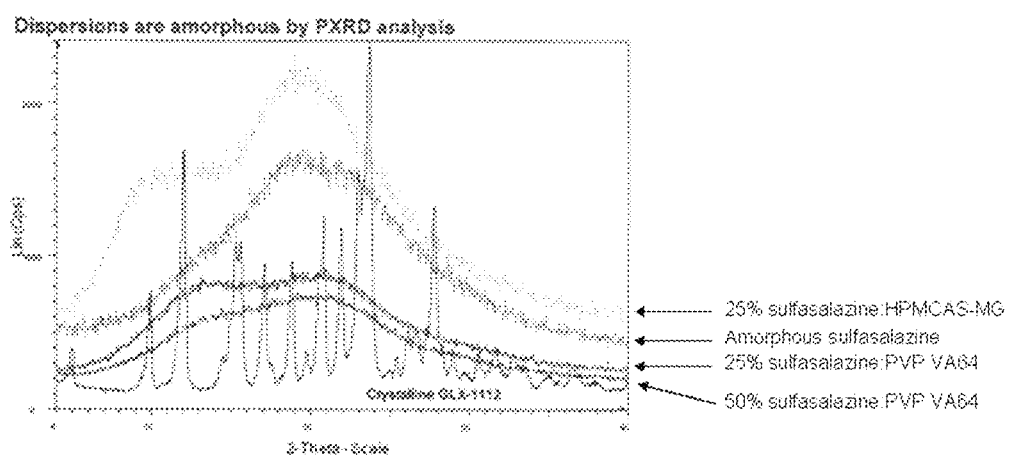

FIG. 13 is a representative graph of results from powder X-ray diffraction (PXRD) analysis of various sulfasalazine formulations.

Figure 14:
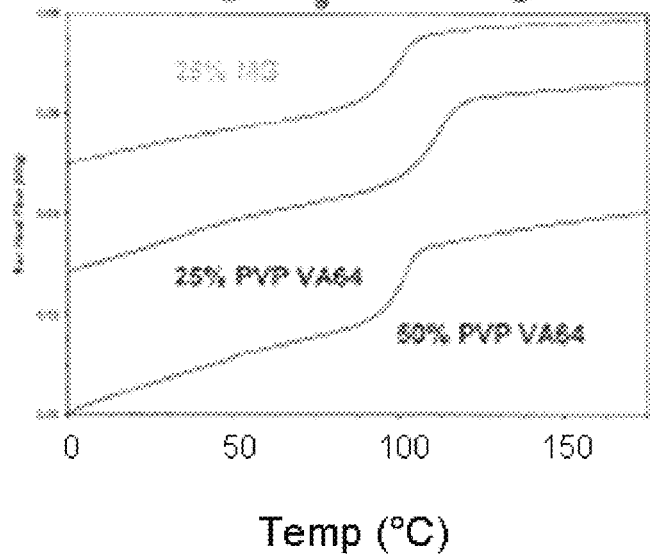

FIG. 14 is a representative graph of results from modulated differential scanning calorimetry (mDSC) analysis of sulfasalazine compositions. The resulting glass-transition temperature (Tg) curve is used to determine the homogeneity of the composition.

Figure 15:
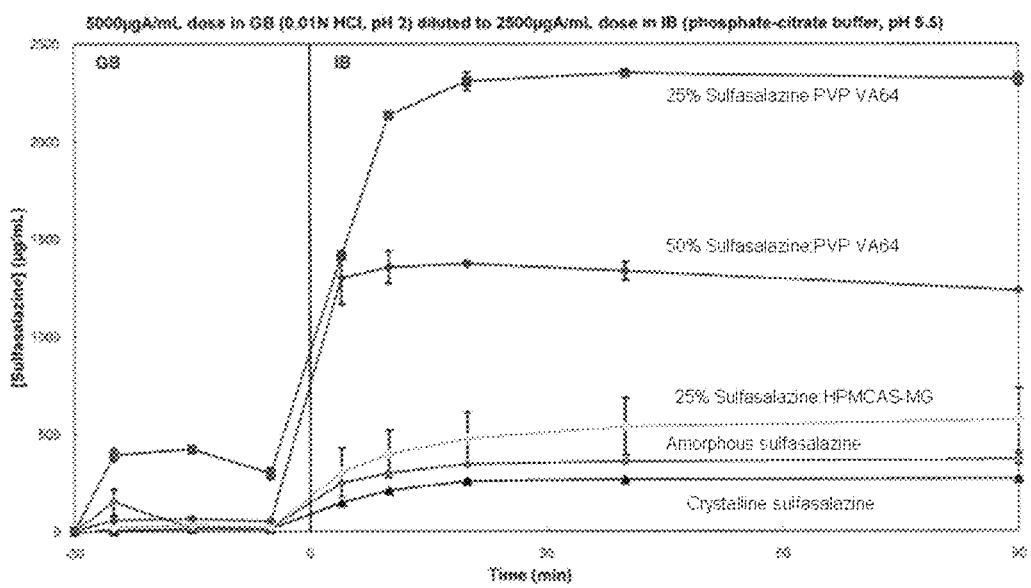

FIG. 15 is a representative graph of results measuring solubility of sulfasalazine preparations at gastric buffer (GB) and intestinal buffer (IB) of the sulfasalazine formulations.

Figure 16:
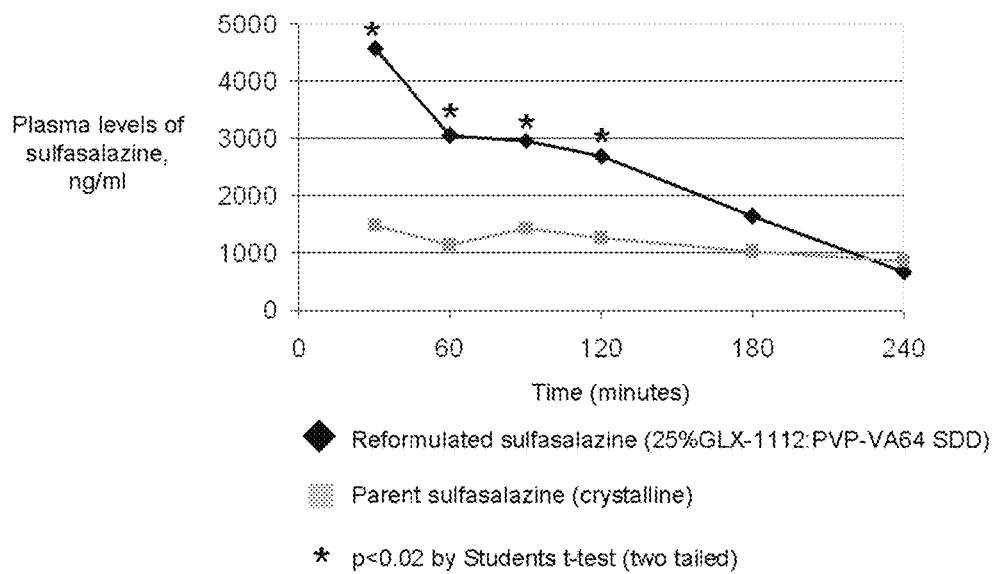

FIG. 16 is a representative graph of results showing an increase in oral bioavailability of sulfasalazine in a Sprague-Dawley rats following reformulation.

In addition to the exemplary embodiments, aspects and variations described above, further embodiments, aspects and variations will become apparent by reference to the drawings and figures and by examination of the following descriptions.

DETAILED DESCRIPTION OF THE INVENTION

Definitions

Unless specifically noted otherwise herein, the definitions of the terms used are standard definitions used in the art of organic synthesis and pharmaceutical sciences. Exemplary embodiments, aspects and variations are illustrated in the figures and drawings, and it is intended that the embodiments, aspects and variations, and the figures and drawings disclosed herein are to be considered illustrative and not limiting.

As used herein, "neurodegenerative disease or disorder" means diseases of the nervous system that are caused, at least in part, by excessive glutamate signaling. Examples of neurodegenerative diseases where anti-glutamatergics are used clinically include Parkinson's disease (Amantadine and Budipine), Alzheimer's disease (Memantine), neuropathic pain (Topamax, Pregabalin), epilepsy (Carbamazepine, Lamictal, Keppra), and ALS (Rilutek). Anti-glutamatergic agents are also being investigated for use in traumatic brain injury, Huntington's disease, ischemic stroke and multiple sclerosis.

"Amorphous" refers to a solid state form of a compound (e.g., sulfasalazine) that is non-crystalline, having no or substantially no molecular lattice structure, wherein the three dimensional structure positions of the molecules relative to one another are essentially random. See for example, Hancock et al. "Characteristics and significance of the amorphous state in pharmaceutical systems" J. Pharm. Sci. Vol. 86, pp. 1-12 (1997). As a result, an amorphous material will have liquid-like short range order and, when examined by X-ray diffraction, will generally produce broad, diffuse scattering and will result in peak intensity sometimes centered on one or more broad bands (known as an amorphous halo). Thus, PXRD analysis of an amorphous material will provide a 2-theta pattern with one or more broad bands with no distinctive peaks; unlike the patterns of a crystalline solid material. As used herein, "essentially amorphous" means that the compound in the material is in at least 80% amorphous form (that is, no more than 20% crystalline compound), which means such material may exhibit one or more distinctive peaks in a PXRD analysis.

"Bioavailability" refers the percentage of a dose of a drug that enters the circulation when that dose of the drug is administered orally to a human, rodent, or other animal.

"In vitro solubility" in reference to the solubility of sulfasalazine means the $C_{max}$ IB at 90 minutes value for the solubility of sulfasalazine (as exemplified in Table 9) when measured by the methods of Example 9.

"Standard formulation of sulfasalazine" refers to formulations of sulfasalazine that are considered to be essentially equivalent to Azulfidine in terms of the bioavailability of the sulfasalazine in the formulation. These formulations include, but are not limited to, Azulfidine®, Azulfidine® EN (enteric coated), Salazopyrin®, Salazopyrin® EN (enteric coated), SULFASALAZINE TABLETS (Watson Laboratories), SULFAZINE© (Vintage Pharmaceuticals, Inc.), Sazo En (Wallace Pharmaceuticals Ltd.), Salazopyrin EN (Wallace Pharmaceuticals Ltd.), Salazopyrin (Wallace Pharmaceuticals Ltd.), Sazo EC (Wallace Pharmaceuticals Ltd.), Saaz (IPCA Laboratories Ltd.), Saaz DS (IPCA Laboratories Ltd.), Zemosal (Sun Pharmaceutical Industries Ltd.), Colizine (Synmedic Laboratories), Iwata (Cadila Pharmaceuticals Ltd.), and Salazar EC (Cadila Pharmaceuticals Ltd.).

"Dosing interval" in this application means the period of time between administrations of a composition to a patient. For example, if a drug is administered to a patient every 8 hours, then the dosing interval is the 8 hour period that follows the administration of the drug. For the purposes of this application, the condition "for the entire dosing interval" will be considered to be met if the level of the sulfasalazine is at or above the designated level at the end of the dosing interval (but before any next administration of the sulfasalazine).

"Excipient" is a material used in the compositions of the present application, and may be solid, semisolid or liquid materials which serve as vehicles, carriers or medium for the active compound, such as sulfasalazine. Typical excipients may be found in Remington: The Science and Practice of Pharmacy, A. Gennaro, ed., 20th edition, Lippincott, Williams & Wilkins, Philadelphia, Pa..; Handbook of Pharmaceutical Excipients by Raymond C. Rowe, Paul J. Sheskey, Walter G. Cook and Marian E. Fenton. 7th Edition, Pharmaceutical Press, London, UK and The United States Pharmacopeia and National Formulary (USP-NF), Rockville, Md. Excipients include, but are not limited to, pharmaceutically acceptable polymers.

"Pharmaceutically acceptable salts" means salt compositions that is generally considered to have the desired pharmacological activity, is considered to be safe, non-toxic and is acceptable for veterinary and human pharmaceutical applications. Such salts include acid addition salts formed with inorganic acids such as hydrochloric acid, hydrobromic acid, sulfuric acid, phosphoric acid, and the like; or with organic acids such as acetic acid, propionic acid, hexanoic acid, malonic acid, succinic acid, malic acid, citric acid, gluconic acid, salicylic acid and the like.

"PVP VA64," as used herein, means vinylpyrrolidone-vinyl acetate copolymers with the general formula $(C_6H_9NO)_n \times (C_4H_6O_2)_m$. Sources of PVP VA64 include, but are not limited to, BASF (Ludwigshafen, Germany) as Kollidon® VA 64 and Shanghai Lite Chemical Technology Co., Ltd. As Copovidone (PVP/VA64).

"Copolyvidone," "Crospovidone" or "polyvinylpyrrolidone polyvinylacetate" is a polyvinylpyrrolidone polyvinylacetate copolymer.

"Polyvinylpyrrolidone" or "PVP" refers to a polymer, either a homopolymer or copolymer, containing N-vinylpyrrolidone as the monomeric unit. Typical PVP polymers are homopolymeric PVPs and the copolymer vinyl acetate vinylpyrrolidone. The homopolymeric PVPs are known to the pharmaceutical industry under a variety of designations including Povidone, Polyvidone, Polyvidonum, Polyvidonum soluble and Poly(1-vinyl-2-pyrrolidone). The copolymer vinyl acetate vinylpyrrolidone is known to the pharmaceutical industry as Copolyvidon, Copolyvidone and Copolyvidonum.

"Progressive multiple sclerosis" or "P-MS" refers to all the sub-types of Progressive Multiple Sclerosis characterized by chronic accumulation of disability, which are Primary Progressive Multiple Sclerosis (PP-MS), Secondary Progressive Multiple Sclerosis (SP-MS) and Progressive-Relapsing Multiple Sclerosis (PR-MS).

"Therapeutically effective amount" means an amount of sulfasalazine or other active ingredient of the application that elicits any of the treatment effects listed in the specification. To be clear, when a unit dose of an active ingredient in the present application is administered in multiple doses a day, the term "therapeutically effective amount" includes unit doses that are themselves sub-therapeutic, but that cumulatively result in an administered amount that elicits a treatment effect.

"Treating" or "treatment" of a disease as used herein means (a) inhibiting or delaying progression of the disease, (b) reducing the extent of the disease, (c) reducing or preventing recurrence of the disease, and/or (d) curing the disease. Treating or treatment include, but are not limited to, one or more of (1) limiting, inhibiting or reducing the rate of accumulation of disability and/or loss of motor neuron function; (2) delaying the progression of the disease, such as P-MS or ALS; (3) limiting, inhibiting or reducing neuronal dysfunction and/or muscular atrophy, (4) limiting or arresting its development, (5) relieving the disease, such as P-MS or ALS, i.e., causing the regression of P-MS or ALS; (6) reducing or preventing the recurrence of the accumulation of disability and/or the loss of motor neuron function; (7) reducing or preventing the recurrence of neuronal dysfunction and/or muscular atrophy; (8) palliating the symptoms of the disease, such as P-MS ALS, (9) increase in survival after onset of P-MS or ALS; and/or, (10) attenuation of neuroinflammation.

Therapeutic Compositions

The invention provides pharmaceutical compositions for use in treating neurodegenerative diseases or disorders. In some embodiments, the pharmaceutical compositions comprising sulfasalazine are formulated such that the bioavailability of the sulfasalazine in the administered pharmaceutical composition is increased in comparison to administration of crystalline sulfasalazine or the standard formulation of sulfasalazine.

In one aspect, the pharmaceutical compositions of the invention may employ PVP VA64 or polymer compositions that are related to PVP VA64, and such compositions may include polyvinyl pyrrolidone and polyoxyethylene-polyoxypropylene copolymers (also known as poloxamers). In another aspect, the pharmaceutical compositions of the invention may also employ one or more polymer compositions and additives that are related to HPMCAS-MG such as hydroxypropyl methyl cellulose acetate succinate (the L, M, and H grades, known as AQUAT-L, AQUAT-M and AQUAT-H grades), hydroxypropyl methyl cellulose phthalate (HPMCP), cellulose acetate phthalate (CAP), cellulose acetate trimellitate (CAT), cellulose acetate succinate, methylcellulose acetate succinate, carboxymethyl ethyl cellulose (CMEC), hydroxypropyl methyl cellulose, and hydroxypropyl methyl cellulose acetate.

Pharmaceutically acceptable polymers include, but are not limited to, PVP VA64, polyvinyl pyrrolidone, polyoxyethylene-polyoxypropylene copolymers (also known as poloxamers), hydroxypropyl methyl cellulose acetate succinate (HPMCAS), hydroxypropyl methyl cellulose phthalate (HPMCP), cellulose acetate phthalate (CAP), cellulose acetate trimellitate (CAT), hydroxypropyl methyl cellulose acetate phthalate, hydroxypropyl methyl cellulose acetate trimellitate, cellulose acetate succinate, methylcellulose acetate succinate, carboxymethyl ethyl cellulose (CMEC), hydroxypropyl methyl cellulose, and hydroxypropyl methyl cellulose acetate, hydroxypropyl methyl cellulose acetate succinate (the L, M, and H grades, known as AQUAT-L, AQUAT-M and AQUAT-H grades).

In one aspect, the pharmaceutical compositions of the invention comprise sulfasalazine and a polymer, wherein the ratio of sulfasalazine to polymer in the composition is about 1:99 wt/wt to 50:50 wt/wt. In another aspect, the ratio of sulfasalazine to polymer is about 5:95 wt/wt to 45:55 wt/wt, about 10:90 wt/wt to about 40:60 wt/wt, about 15:85 wt/wt to about 35:65 wt/wt, or about 20:80 wt/wt to about 30:70 wt/wt.

Also provided are pharmaceutical compositions comprising pharmaceutically acceptable excipients. Such excipients include, but are not limited to, polyvinylpyrrolidinone, gelatin, hydroxycellulose, acacia, polyethylene glycol, mannitol, sodium chloride, sodium citrate, and pharmaceutically acceptable polymers.

Pharmaceutically acceptable solid or liquid carriers may be added to enhance or stabilize the composition, or to facilitate preparation of the composition. Liquid carriers include syrup, peanut oil, olive oil, glycerin, saline, alcohols or water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulation and compressing, when necessary, for tablet forms; or milling, mixing and filling for hard gelatin capsule forms. When a liquid carrier is used, the preparation will be in the form of a syrup, elixir, emulsion, or an aqueous or non-aqueous suspension. Such a liquid formulation may be administered directly by mouth or filled into a soft gelatin capsule.

In some embodiments, pharmaceutical compositions of the invention include a pharmaceutically acceptable, non-toxic composition formed by the incorporation of any of the normally employed excipients, such as, for example, mannitol, lactose, starch, magnesium stearate, sodium saccharine, talcum, cellulose, sodium crosscarmellose, glucose, gelatin, sucrose, magnesium carbonate, and combinations thereof. Such compositions include suspensions, tablets, dispersible tablets, pills, capsules, powders, sustained release formulations and the like.

In addition, the compositions can comprise pharmaceutically acceptable carriers or customary auxiliary substances, such as glidants; wetting agents; emulsifying and suspending agents; preservatives; antioxidants; anti-irritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; silicone derivatives; spreading auxiliaries; stabilizers; sterilants; suppository bases; tablet auxiliaries, such as binders, fillers, disintegrants or coatings; propellants; drying agents; pacifiers; thickeners; waxes; plasticizers and white mineral oils.

In some embodiments, the pharmaceutical compositions of the invention are administered in oral dosage form. Oral dosage forms that may be used in the invention include, but are not limited to, pills, tablets, chewable tablets, capsules, syrups, sustained release formulations, and suspensions. In some embodiments, where the composition is a pill or tablet, the composition may contain, along with sulfasalazine, a diluent such as lactose, sucrose, dicalcium phosphate, or the like; a lubricant such as magnesium stearate or the like; and a binder such as starch, gum acacia, gelatin, polyvinylpyrolidinecellulose and derivatives thereof, and the like. In other embodiments, tablet forms of the composition may include one or more of lactose, sucrose, mannitol, corn starch, potato starch, alginic acid, microcrystalline cellulose, acacia, gelatin, guar gum, colloidal silicon dioxide, crosscarmellose sodium, talc, magnesium stearate, calcium stearate, zinc stearate, stearic acid, preservatives, flavoring agents, pharmaceutically acceptable disintegrating agents, moistening agents and pharmacologically compatible carriers; and combinations thereof. In other embodiments, formulations suitable for oral administration can consists of liquid suspensions such as an effective amount of sulfasalazine suspended in diluents such as water, saline, or orange juice; sachets, lozenges and troches, each containing a predetermined amount of sulfasalazine as solids or granules; powders, suspensions in the above appropriate liquid; and suitable emulsions.

In certain embodiments, pharmaceutical compositions containing a solid dispersion of sulfasalazine and at least one polymer are provided wherein the sulfasalazine is present in essentially amorphous form. In other embodiments, a method for the preparation of amorphous sulfasalazine is provided. One method for producing a solid molecular dispersion of amorphous sulfasalazine provided herein involves solvent spray drying. Other techniques that can be used to prepare solid molecular dispersions of amorphous sulfasalazine include, without limitation: (1) milling; (2) extrusion; (3) melt processes, including high melt-congeal processes and melt-congeal processes; (4) solvent modified fusion; (5) solvent processes, including spray coating, lyophilization, solvent evaporation (e.g., rotary evaporation) and spray-drying; and (6) non-solvent precipitation.

In one aspect, pharmaceutical compositions of the invention are formulated through spray drying. There are various methods for creating spray dried compositions, e.g., see EP1469830, EP1469833, EP1653928, WO 2010/111132, WO 96/09814; WO 97/44013; WO 98/31346; WO 99/66903; WO 00/10541; WO 01/13893, WO 2012/031133, WO 2012/031129, and U.S. Pat. Nos. 6,763,607, 6,973,741, 7,780,988, and 8,343,550. In certain of these embodiments, the volume mean diameter of the spray dried dispersion is less than about 500 micrometers in diameter or less than about 200 micrometers or less than about 100 micrometers or less than about 50 micrometers or less than about 10 micrometers. In certain embodiments, the pharmaceutical compositions of the invention are formulated as nanoparticles. There are multiple approaches for formulating pharmaceutical compositions as nanoparticles, e.g., see WO 2009/073215, U.S. Pat. Nos. 8,309,129; 8,034,765 and 5,118,528.

Typical loadings of sulfasalazine in the formulation can range from 1 wt % API to 50 wt % in the compositions, although more likely they will range from 5 wt % API to 50 wt %, or 10 wt % to 40 wt %. This will depend on several factors, including (1) the nature of the polymers in the composition, and (2) the storage stability of the composition (e.g., its tendency to phase separate). The sulfasalazine prepared and used in the compositions of the present application may be amorphous. In one particular aspect, the PXRD spectrum of the amorphous sulfasalazine shows a 2-theta pattern with a broad band having no distinctive peaks. In another aspect, the sulfasalazine used in the compositions of the present application are at least 80% amorphous, 90% amorphous, at least 93% amorphous, at least 95% amorphous, at least 97% amorphous, at least 98% amorphous, at least 99% amorphous, at least 99.5% amorphous or about 100% amorphous. In another aspect, the remaining or the balance of the sulfasalazine used in the compositions are crystalline material, semi-crystalline material or combination of crystalline and semi-crystalline materials as determined by PXRD.

Also included in the above embodiments, aspects and variations are salts of sulfasalazine, such as arginate and the like, gluconate, and galacturonate. Certain of the compounds of the present invention can exist in unsolvated forms as well as solvated forms, including hydrated forms, and are intended to be within the scope of the present invention. Certain of the above compounds may also exist in one or more solid or crystalline phases or polymorphs, the variable biological activities of such polymorphs or mixtures of such polymorphs are also included in the scope of this invention.

The invention also provides methods for treatment of P-MS, ALS or other neurodegenerative diseases comprising administering pharmaceutical compositions comprising effective amounts of inhibitors of system $x_c^-$ other than sulfasalazine. In various embodiments, inhibitors of system $x_c^-$ include, but are not limited to (S)-4-carboxyphenylglycine, 2-hydroxy-5-((4-(N-pyridin-2-ylsulfamoyl)phenyl)ethynyl)benzoic acid, aminoadipate (AAA), 4-(1-(2-(3,5-bis(trifluoromethyl)phenyl)hydrazono)ethyl)-5-(4 (trifluoromethyl)benzyl)isoxazole-3-carboxylic acid, 5-benzyl-4-(1-(2-(3,5-bis(trifluoro-methyl)phenyl)hydrazono) ethyl)isoxazole-3-carboxylic acid, and 2-hydroxy-5-[2-[4-[(3-methylpyridin-2-yl)sulfamoyl]phenyl]ethynyl] benzoic acid. Formulations of pharmaceutical compositions comprising these inhibitors can be generated by various methods, including those described in Remington: The Science and Practice of Pharmacy, A. Gennaro, ed., 20th edition, Lippincott, Williams & Wilkins, Philadelphia, Pa.

Administration

In various embodiments, pharmaceutical compositions of the invention may be administered to patients by oral dosing. In certain of those embodiments, the pharmaceutical composition comprising sulfasalazine is formulated such that the oral bioavailability of the sulfasalazine is higher than that of crystalline sulfasalazine or than the current on-market formulation of sulfasalazine.

In various embodiments, pharmaceutical compositions of the invention may be administered to a patient by various routes other than oral dosing such as, but not limited to, intravenously, intramuscular, buccal and rectal administration. Suitable formulations for each of these methods of administration may be found in, for example, Remington: The Science and Practice of Pharmacy, A. Gennaro, ed., as noted above.

The specific dose of a pharmaceutical composition of the invention administered to a patient may be determined considering the various circumstances of the patient being treated such as the route of administration, the formulation of the pharmaceutical composition, the patient's medical history, the weight of the patient, the age and sex of the patient, and the severity of the condition being treated. In some embodiments, the patient is administered a pharmaceutical composition comprising sulfasalazine where in the amount of sulfasalazine is between 100 to 20,000 milligrams/dose. In some embodiments, the patient is administered an amount of sulfasalazine between 200 and 10,000 milligrams/dose. In some embodiments, the patient is administered an amount of sulfasalazine between 400 and 4000 milligrams/dose. In some embodiments, the patient is administered a pharmaceutical composition comprising sulfasalazine where in the amount of sulfasalazine is between 500 and 2,000 milligrams/dose.

The frequency of administration of a pharmaceutical composition of the invention to a patient may be determined considering the various circumstances of the patient being treated such as the route of administration, the formulation of the pharmaceutical composition, the patient's medical history, the weight of the patient, the age and sex of the patient, the rate of disease progression and the severity of the condition being treated. In some embodiments, the patient is administered a dose of the pharmaceutical composition more than once. In some embodiments, the patient is administered a dose of the pharmaceutical composition once a day. In some embodiments, the patient is administered a dose of the pharmaceutical composition comprising sulfasalazine twice a day, three times a day, or four times a day. In some embodiments, a patient is administered a dose of the pharmaceutical composition of the invention less frequently than once a day, e.g., once every two days or once a week.

The length of treatment by the methods of the invention may be determined considering the various circumstances of the patient being treated such as the patient's medical history, the weight of the patient, the age and sex of the patient, the rate of disease progression and the severity of the condition being treated. In some embodiments, the patient is treated for the rest of their lifetime. In some embodiments, the patient is treated for as long as the disease is active. In some embodiments, the patient is treated for less than one month. In some embodiments, the patient is treated for more than one month, e.g., for one year.

In some embodiments, pharmaceutical compositions of the invention are administered to a patient in combination with one or more other drug compositions. Such one or more other drug compositions may be administered concurrently with pharmaceutical compositions of the invention or may be administered at separate times. In certain embodiments, the one or more other drug compositions are formulated into pharmaceutical compositions of the invention. In other embodiments, the one or more drug composition and the pharmaceutical composition of the invention are administered as separate compositions. In some embodiments, Mitoxantrone, Gilenya, Masitinib, Siponimod, Tcelna, Tecfidera, Lemtrada, Laquinimod, Daclizumab, Ocrelizumab, Cladribine, Daclizumab, Tysabri, Campath, Rituximab, Fingolimod, Azathioprine or Ibudilast is administered in combination with a pharmaceutical composition of the invention to patients with P-MS. In certain of those embodiments, Mitoxantrone, Gilenya, Masitinib, Siponimod, Tcelna, Tecfidera, Lemtrada, Laquinimod, Daclizumab, Ocrelizumab, Cladribine, Daclizumab, Tysabri, Campath, Rituximab, Fingolimod, Azathioprine or Ibudilast is administered in combination with a pharmaceutical composition of the invention comprising sulfasalazine. In certain embodiments, Mitoxantrone, Gilenya, Masitinib, Siponimod, Tcelna, Tecfidera, Lemtrada, Laquinimod, Daclizumab, Ocrelizumab, Cladribine, Daclizumab, Tysabri, Campath, Rituximab, Fingolimod, Azathioprine or Ibudilast is administered to a patients with P-MS in combination with a pharmaceutical composition comprising sulfasalazine and PVP VA64, wherein the ratio of the sulfasalazine to PVP VA64 in the composition is about 20:80 wt/wt to 30:70 wt/wt. In some embodiments, riluzole is administered in combination with a pharmaceutical composition of the invention to patients with ALS. In certain of those embodiments, riluzole is administered in combination with a pharmaceutical composition of the invention comprising sulfasalazine. In certain embodiments, riluzole is administered to a patients with ALS in combination with a pharmaceutical composition comprising sulfasalazine and PVP VA64, wherein the ratio of the sulfasalazine to PVP VA64 in the composition is about 20:80 wt/wt to 30:70 wt/wt.

EXAMPLES

The following examples below are intended to be purely exemplary of the invention and should not be considered to limit the invention in any way. The examples are not intended to represent that the experiments below are all or the only experiments performed. Efforts have been made to ensure accuracy with respect to numbers used but some experimental errors and deviations should be accounted for. Unless otherwise indicated, parts and percentages are by weight, temperature in degrees Celsius (° C.) and pressure is at or near atmosphere. These examples may be employed for the preparation of the compositions and formulation of the present application.

Example 1

Treatment with Sulfasalazine Increases Absolute Survival and Increases the Lifespan of SOD1 Mice after Onset of Definitive Neurological Disease The following experiments demonstrate that treatment with sulfasalazine: (1) increased the absolute lifespan of SOD1 mice, and (2) extended lifespan of SOD1 mice after onset of definitive neurological disease. This latter survival parameter is relevant to human patients, who typically will not begin therapy until after definitive diagnosis of ALS.

High-copy SOD1$^{G93A}$ transgenic mice were derived from the B6SJL-TgN(SOD1G93A)1Gur strain, obtained from The Jackson Laboratory (Bar Harbor, Me.) and originally produced by Gurney, e.g. Gurney et al., *Science* 264: 1772-1775 (1994).

Animal experiments with the SOD1 model were performed at ALS Therapy Development Institute (herein "ALS-TDI"; Cambridge, Mass.). All mice were genotyped to verify copy number of the SOD1 transgene. Animal handling and study protocols were as previously described by ALS-TDI, e.g. Scott et al., *Amyotroph. Lateral Scler.* 9: 4-15 (2008).

Groups were balanced with respect to gender and body weight within gender. In addition, groups were age-matched and littermate-matched. Each male and female in the drug treatment group had a corresponding male and female littermate in the vehicle control group. A total of 59 mice were used in the study, divided into 2 cohorts as shown in Table 1. Each cohort of was balanced between males and females.

TABLE 1

Cohorts used in the survival study

| Cohort | Genotype | Treatment | Male/Female |
|---|---|---|---|
| 1 (n = 32) | SOD1 | Vehicle Control | 16/16 |
| 2 (n = 27) | SOD1 | Sulfasalazine (Drug Treatment) | 14/13 |

Starting at an age of 50 days, mice were administered sulfasalazine or saline two times per day (8 hours apart), 7 days per week at a dose of 200 mg/kg. Sulfasalazine was prepared by weighing 100 mg of compound into a 50 mL corning tube. 5 mL of 0.1 N NaOH was added and the tube gently sonicated. Approximately 140 µL of 1 N HCl was then added to bring the pH to 8.00. The resulting 20 mg/mL solution was delivered by intraperitoneal injection at 10 ml/kg. Vehicle treated mice were administered saline.

Neurological scores were assessed daily from day 50 for both hind legs. The neurological score was based on a scale of 0 to 4. Criteria used to assign each score level are from Scott et al., *Amyotroph. Lateral Scler.* 9: 4-15 (2008) and are described in Table 2.

TABLE 2

Criteria for assigning neurological scores

| Score | Criteria |
|---|---|
| 0 | No ALS symptomology. Full extension of hind legs away from lateral midline when mouse is suspended by its tail, and mouse can hold this for 2 seconds, suspended 2-3 times. |
| 1 | Initial Pre-ALS symptomology. Collapse or partial collapse of leg extension towards lateral midline (weakness) or trembling of hind legs during tail suspension. |
| 2 | Definitive neurological disease. Toes curl under at least twice during walking 2 paper towel lengths (≈12 inches), or any part of foot is dragging along cage bottom/table. |
| 3 | Advanced disease. Rigid paralysis or minimal joint movement, foot not being used for forward motion. |
| 4 | End stage. Mouse cannot right itself within 30 seconds from either side. |

The date of definitive neurological disease was the day that the mouse first scored a "2" on the Neurological Score. Upon reaching a score of Neurological Score of "4", mice were euthanized and the date of death was recorded.

Figure 1:
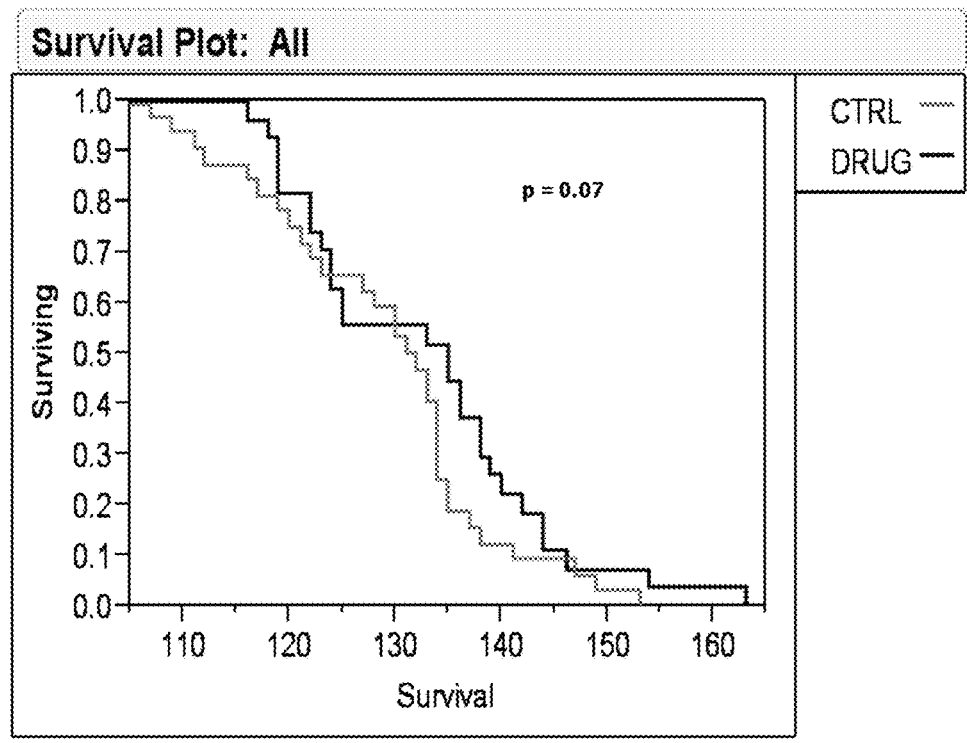
FIG. 1 shows a representative Kaplan-Meier absolute survival curves in SOD1$^{G93A}$ mice (herein after "SOD1 mice"). The vehicle-treated (CTRL) and sulfasalazine-treated (DRUG) cohorts are plotted in gray and black, respectively.

Sulfasalazine had no statistical effect on time of disease onset. Treatment with sulfasalazine increased median absolute survival of the SOD1 mice by 3.5 days, with a p-value of p=0.07 using the Cox proportional hazard likelihood ratio (FIG. 1). While the effect of sulfasalazine on absolute survival is modest, it is 68% greater than riluzole, the only approved therapy for ALS, when tested in the same SOD1 model under similar conditions (sulfasalazine, 2.7% increased absolute lifespan vs. riluzole, 1.6% increased absolute lifespan; see e.g. Lincecum et al., *Supplementary Material, Nat. Genetics* 42: 392-411 (2010)).

Figure 2:
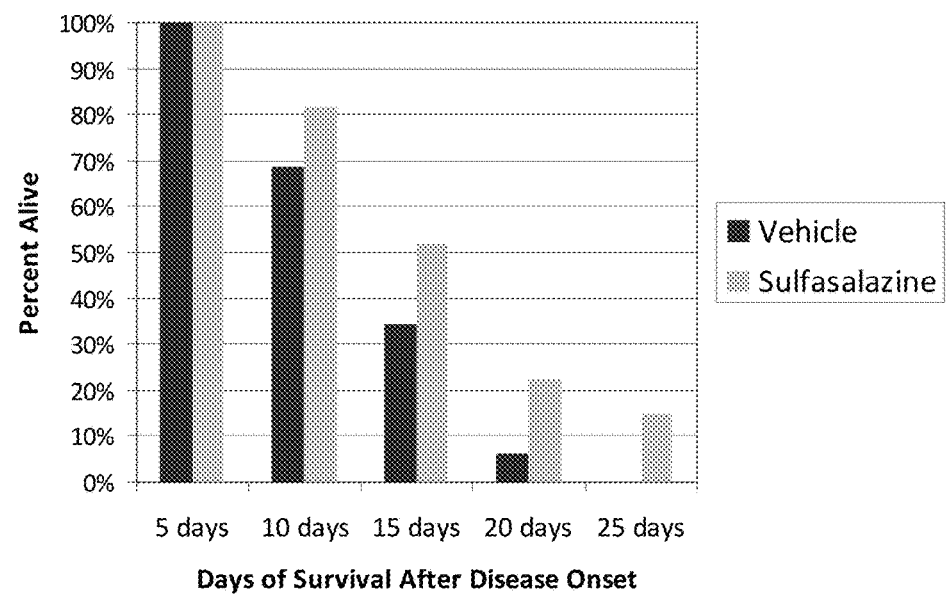
FIG. 2 is representative of histograms showing the distribution of lifespan in vehicle and sulfasalazine treated mice after onset of definitive neurological disease.

Sulfasalazine had a much stronger effect on survival after onset on definitive neurological disease. Survival after onset of definitive neurological disease is defined as the total number of days the mice lived after reaching definitive neurological disease (Neurological Score of 2) and before death (Neurological Score of 4). Survival after onset of definitive neurological disease was analyzed in two ways. The first analysis used the mean ages of definitive disease onset and death to calculate the mean lifespan of the SOD1 mice after disease onset, with and without sulfasalazine treatment. The mean lifespan of the SOD1 mice after onset of definitive neurological disease is shown in Table 3. A histogram plot of the survival of the SOD1 mice treated with vehicle and sulfasalazine following onset of definitive neurological disease is shown in FIG. 2. These analyses showed that sulfasalazine treated mice lived, on average, 39% longer than vehicle treated mice after onset of definitive neurological disease (p=0.02, t-test with Welch's correction for unequal variances). The 95% confidence interval ranged from a lifespan increase of 21% to 52% compared to the untreated mice.

TABLE 3

Mean lifespan after onset of definitive neurological disease.

| Group | Mean Day of Definitive Neurological Disease | Mean Day of Death | Total Days of Survival after Onset of Definitive Disease | Lower 95% Confidence Interval | Upper 95% Confidence Interval |
|---|---|---|---|---|---|
| Vehicle | 116.4 | 128.9 | 12.5 | 10.73 | 14.27 |
| Sulfasalazine | 115.2 | 132.6 | 17.4 | 12.94 | 21.73 |
| Absolute Change | −1.2 | 3.7 | 4.9 | 2.21 | 7.46 |
| Percent Change | −1.0% | 2.9% | 39.2% | 20.6% | 52.3% |
| p-value | p = 0.64 | p = 0.12 | p = 0.02 | | |

The second method used to analyze the survival data was to compare the expected and observed number of days the sulfasalazine treated mice spent in one of 3 disease categories to determine if there was a significant difference between the expected and observed values. The first day that a neurological score was determined was day 50 of age; measurements were collected daily afterwards until death.

The three categories were: (1) days spent before definitive neurological disease, e.g. with a neurological score of 0 or 1; (2) days spent during definitive neurological disease, e.g. with a neurological score of 2 or 3; and (3) days at death, e.g. with a neurological score of 4. By definition, mice were only in the dead state for 1 day, as they were euthanized upon reaching a neurological score of 4; this category was included as a positive control to ensure the integrity of the data and analysis.

The expected distribution of days the sulfasalazine treated mice spent in each of these three disease categories was calculated from the observed distribution of the vehicle treated mice, with the null hypothesis that sulfasalazine treatment had no effect on the distribution. The observed distribution of sulfasalazine treated mice is based on daily scoring and is normalized to the number of mice in the groups.

The results of this analysis are shown in Table 4. The sulfasalazine treated mice, as a group, survived a total of 112 days longer than expected after onset of definitive neurological disease (neurological score of 2 or 3). This result was highly significant by Chi-Square analysis, with a p-value of less than 0.0004 by the Wald test and 0.0003 by the Likelihood ratio test. There was no significant difference in the total days spent in the pre-disease state (neurological score of 0 or 1) or death (neurological score of 4).

TABLE 4

Expected and observed distribution of sulfasalazine neurological scores and calculated p-values.

| Measurement | Disease Category | Vehicle | Expected Days, Sulfasalazine[1] | Observed Days, Sulfasalazine | Observed Days Minus Expected Days | Effect (Wald Tests)[2] Prob > ChiSq | Effect (Likelihood Ratio Tests)[2] Prob > ChiSq |
|---|---|---|---|---|---|---|---|
| Total Days | Before definitive disease onset (neurological score = 0 or 1) | 2041 | 1722 | 1708 | −14 | 0.0004 | 0.0003 |
| | Definitive neurological disease (neurological score = 2 or 3) | 357 | 301 | 413 | 112 | | |
| | Death (neurological score = 4) | 32 | 27 | 27 | 0 | | |
| | Total Observations (Days) | 2430 | 2050 | 2148 | 98 | | |

[1]Expected days for sulfasalazine treated animals if sulfasalazine has no effect on disease; values predicted from vehicle-treated cohort and normalized for number of animals in treated cohort.
[2]Prob > ChiSq is the probability of obtaining a greater Chi-square value by chance alone if treatment has no effect on time spent within each disease category. All statistics performed using the JMP10 statistics program (SAS Institute).

Figure 3:
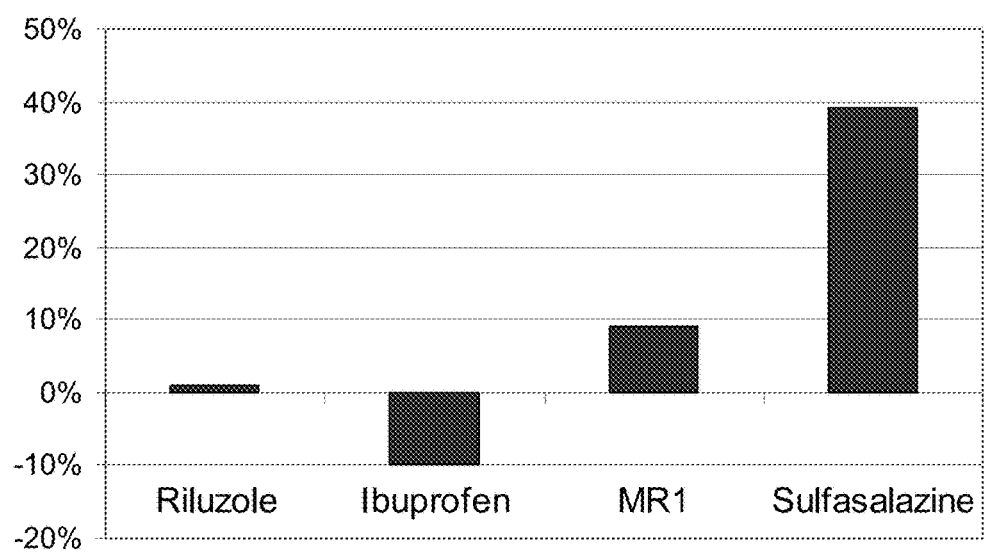
FIG. 3 shows a representative graph of the percent change in lifespan after onset of definitive neurological disease in SOD1 mice treated with riluzole, ibuprofen, MR1 and sulfasalazine.

The increased lifespan following onset of definitive neurological disease seen with sulfasalazine was also compared to published results of other compounds tested in the SOD1 mouse model. FIG. 3 shows the percent difference in survival following onset of neurological disease for sulfasalazine, two general anti-inflammatory compounds (ibuprofen and MR1, an antibody to CD40L) and riluzole, the only drug currently approved for ALS. Sulfasalazine increased lifespan by 39%, anti-CD40L increased lifespan by 9%, riluzole increased lifespan by 1% and ibuprofen decreased lifespan after onset of neurological disease by 10%. See, e.g., Shin et al., *J. Neurochem.* 122: 952-961 (2012); Lincecum et al., *Nat. Genetics* 42: 392-411 (2010).

This comparison illustrates that the increased lifespan observed with sulfasalazine is significantly larger than is observed with other tested compounds, including two general anti-inflammatory compounds (ibuprofen and anti-CD40L) and the only approved therapy for ALS (riluzole).

The experiments in the SOD1 animal model of ALS demonstrate that, while the effect of sulfasalazine on absolute survival is modest, it was superior to riluzole, the only approved therapy for ALS. Importantly, the benefit in survival by sulfasalazine after onset of definitive neurological disease is large, in terms of absolute size (approximately 40%), the statistical significance and when compared to other compounds, including riluzole. It is noteworthy that the entire increase in survival noticed in the absolute survival analysis (median 3.7 days) occurs after the definitive onset of neurological disease. This result is consistent with the expression data (FIG. 6, below) that shows xCT expression escalates with disease progression. Based on the expression profile of the target, it is expected that sulfasalazine would have little effect on delaying the onset of disease, but would have a progressively beneficial effect as disease progresses, as was observed in the survival study.

These experiments demonstrate that sulfasalazine has modest efficacy on absolute survival and strong efficacy on survival after onset of definitive neurological disease in the SOD1 mouse model of ALS. As most ALS patients do not begin therapy until after diagnosis of neurological disease, the latter measurement is especially relevant to the treatment of human disease.

Example 2

Expression of xCT (SLC7A11) is Elevated in the Spinal Cord of SOD1 Mice

The following studies used quantitative immunohistochemistry to determine: (1) if the expression of xCT in the spinal cord was elevated in SOD1 mice, (2) if so, whether xCT over-expression increased with disease progression, and (3) whether treatment with sulfasalazine affected xCT expression in the spinal cord of SOD1 mice.

Two ages of mice were chosen for this analysis: day 85, when SOD1 mice show no overt sign of the ALS-like symptomology, and day 100, when SOD1 mice typically begin displaying the first signs of ALS-like symptomology, such as partial collapse of leg extension towards lateral midline (weakness) or trembling of hind legs during a tail suspension test. For the immunohistochemical studies, a total of 48 mice were divided into 6 cohorts of 8 mice each (4 females and 4 males) as shown in Table 5.

TABLE 5

Cohorts used in the Immunohistochemical Studies

| Cohort (n = 8) | Genotype | Treatment | Age of mouse at sacrifice |
|---|---|---|---|
| 1 | Wild-type | vehicle | 85 days |
| 2 | SOD1 | vehicle | 85 days |
| 3 | SOD1 | sulfasalazine | 85 days |
| 4 | Wild-type | vehicle | 100 days |
| 5 | SOD1 | vehicle | 100 days |
| 6 | SOD1 | sulfasalazine | 100 days |

Starting at an age of 50 days, mice were administered sulfasalazine or saline two times per day (8 hours apart), 7 days per week at a dose of 200 mg/kg. Sulfasalazine was prepared by weighing 100 mg of compound into a 50 mL corning tube. 5 mL of 0.1 N NaOH was added and the tube gently sonicated. Approximately 140 µL, of 1 N HCl was then added to bring the pH to 8.00. The resulting 20 mg/mL solution was delivered by intraperitoneal injection at 10 ml/kg. Vehicle treated mice were administered saline.

Mice were sacrificed by $CO_2$ asphyxiation according to IACUC approved protocols. The spinal cord was extruded with cold PBS into a bath of cold PBS from the vertebral column of mice using an 18 gauge needle inserted in the sacral vertebral column to a friction fit. Upon extrusion, the spinal cord tissue was rinsed and dropped into 4% paraformaldehyde for 24 hours at room temperature (RT, approximately 25° C.). The tissue was then transferred to a 1× phosphate buffered saline (PBS) solution. Samples were then processed by TissueTek processors for paraffin embedding. Spinal cord samples were then embedded in paraffin blocks and oriented for transverse sectioning. Spinal cord samples were sectioned at 10 microns thickness. Three representative sections were cut from lumbar, thoracic and cervical regions of the spinal cord. Samples were pretreated with Pronase for 20 minutes at RT, followed by treatment with 3% $H_2O_2$ for 12 minutes at RT. Horse serum was added to 2% and samples incubated for 20 minutes at RT. The samples were then incubated with the primary antibody (Anti-xCT; purchased from Abcam (Cambridge, Mass.); Catalog #Ab37185; diluted 1:500 in PBS) overnight at 4° C. The secondary antibody (Biotin labeled goat anti-rabbit IgG; 1:500 dilution in PBS) was then added and the reaction incubated overnight at RT. Reaction products were developed using the Vector ABC system (Vector Labs, Burlingame, Calif.) using avidin-conjugated horseradish peroxidase. xCT expression was visualized by addition of the chromogenic substrate DAB (3,3'-diaminobenzidine) for 10 minutes at RT. Each stained section was imaged at objectives: 4×, 10×, 20× and 40×. For each objective image, light parameters were optimized and kept consistent across all sections. For SLC7A11 analysis, all images that were captured at 20× were then imported into ImageJ freeware (NIH, Bethesda, Md.). A maximum entropy threshold algorithm was applied to all images in a completely blinded fashion to filter out all pixels that were not stained as DAB positive. The key parameter measured and reported is area fraction. Area fraction is the proportion of total pixels that are DAB positive in the ventral horn of the spinal cord. All statistical analyses were performed using JMP® 7.0, SAS Institute, Inc. Area fraction was compared with respect to treatment using 1-way ANOVA analysis, with a p-value of 0.05 considered significant.

Figure 4:
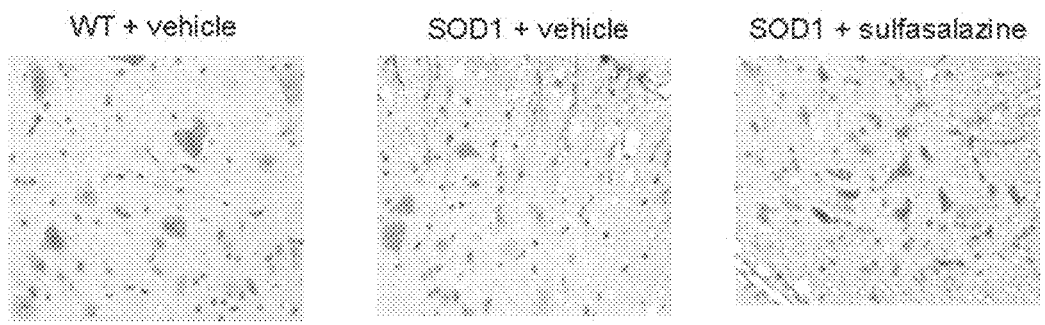
FIG. 4 shows a representative samples from Day 100 mice stained for xCT protein expression (brown).

FIG. 4 shows representative images from day 100 mice. Increased expression of xCT is visible in the sections from the SOD1 mice, with and without sulfasalazine treatment.

Figure 5:
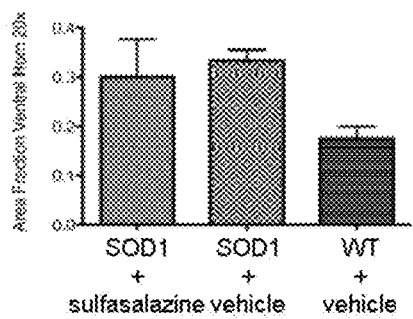
FIG. 5 is representative of an area fraction analysis of xCT expression in the ventral horn of the cervical and lumbar regions of the spinal cord in day 85 and day 100 mice. The symbol '*' indicates the indicated measurement between groups reached a statistical significance of $p<0.05$.
Figure 5:
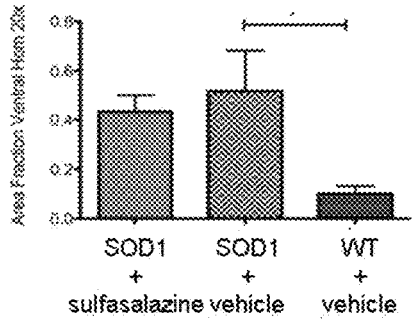
Figure 5:
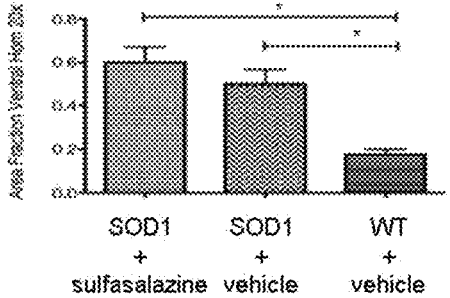
Figure 5:
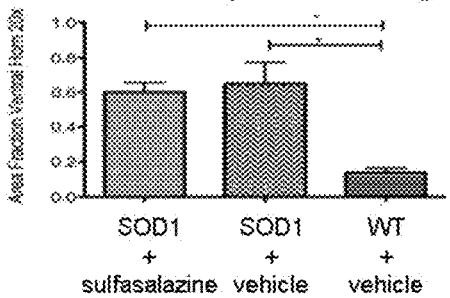

FIG. 5 shows the quantitation of xCT area fraction for the cervical and lumbar regions of the spinal cord in day 85 and day 100 mice. At day 85, xCT protein levels were elevated in both the cervical and lumbar regions in SOD1 mice, reaching statistical significance (p<0.05) in the lumbar region (FIG. 5, panel B). At day 100, xCT protein levels were elevated in both the cervical and lumbar regions in SOD1 mice, reaching statistical significance (p<0.05) in both regions (FIG. 5, Panels C and D).

FIG. 6 compares total xCT expression levels in the ventral horn of the spinal cord in day 85 and day 100 mice. For this analysis, values for the cervical, thoracic and lumbar regions were combined into a single value. In the day 85 SOD1 mice, xCT protein levels were elevated by approximately 50% in the combined spinal cord sections compared to day 85 wild-type mice. In the day 100 SOD1 mice, xCT protein levels were elevated by approximately 300% across in the combined spinal cords sections compared to day 100 wild-type mice.

These results demonstrate that (1) xCT target expression is elevated in the diseased tissue—the ventral portion of the spinal cord-of SOD1 mice; (2) expression of xCT escalates significantly during disease progression in the SOD1 mice (day 85 versus day 100, FIGS. 6), and (3) treatment with sulfasalazine did not have a significant effect on xCT expression (FIG. 5, Panels A-D). Thus, there does not appear to be a compensatory or rebound effect on xCT levels when it is inhibited by sulfasalazine. Such a rebound effect could lead to loss of efficacy upon treatment.

The increased expression of xCT observed during disease progression is consistent with sulfasalazine having greatest efficacy during the later stages of disease.

Example 3

Sulfasalazine Reduces Levels of Neuroinflammatory Cells in the Spinal Cord of SOD1 Mice The following experiments employed quantitative immunohistochemistry to: (1) compare the neuroinflammatory cell populations in the spinal cord of SOD1 mice to the cell populations in wild-type mice, and (2) test whether the treatment with sulfasalazine decreases neuroinflammatory cell populations in the spinal cord of SOD1 mice.

The same test mice, spinal cord preparations and methods of analysis used in the neuroinflammatory study were identical to those used in the xCT quantitation study. Two neuroinflammatory cell populations were quantitated: (1) activated microglial cells using an antibody to the F4/80 antigen, and (2) activated astrocytes, using an antibody to the GFAP antigen. For each objective image, light parameters were optimized and kept consistent across all sections. Images that were captured at 20× were then imported into ImageJ freeware (NIH, Bethesda, Md.). A maximum entropy threshold algorithm was applied to all images in a completely blinded fashion to filter out all pixels that were not stained as DAB positive. 20× images were analyzed in a blinded fashion and mean area fraction occupied by stain was tabulated. Levels of neuroinflammation in the spinal cord were assessed by measuring the area fraction of the area of the ventral horn in the spinal cord occupied by activated astrocytes or microglia. Area fraction was compared with respect to treatment using 1-way ANOVA analysis, with a p-value of 0.05 considered significant.

For quantitation of microglial activation, samples were pretreated with Pronase for 20 minutes at room temperature, followed by treatment with 3% $H_2O_2$ for 12 minutes at room temperature (25° C.). Goat serum was added to 2% and samples incubated for 20 minutes at room temperature. The samples were then incubated with the primary antibody (Anti-F4/80) purchased from Serotec (Catalog # MCA497R; Oxford, United Kingdom), diluted 1:250 in PBS overnight at 4° C. The secondary antibody (Biotin labeled goat anti-rabbit IgG; 1:250 dilution in PBS) was then added and the reaction incubated 1 hour at room temperature. Reaction products were developed using the Vector ABC system (Vector Labs, Burlingame, Calif.) using avidin-conjugated horseradish peroxidase (45 minutes at room temperature). Activated microglia were visualized by addition of the chromogenic substrate DAB (3,3'-diaminobenzidine) for 6 minutes at room temperature.

For quantitation of astrocyte activation, samples were pretreated with heated citrate buffer for 20 minutes, followed by treatment with 3% $H_2O_2$ for 12 minutes at room temperature. Horse serum was added to 2% and samples incubated for 20 minutes at room temperature. The samples were then incubated with the primary antibody (Anti-GFAP) purchased from Abcam (Catalog # Ab10062; Cambridge, Mass.), diluted 1:1000 in PBS overnight at 4° C. Reaction products were developed using the Vector ImmPress system (Vector Labs, Burlingame, Calif.) using an anti-mouse IgG-conjugated horseradish peroxidase. Activated astrocytes were visualized by addition of the chromogenic substrate DAB (3,3'-diaminobenzidine) for 90 seconds at room temperature.

FIG. 7 shows representative images from tissue from day 85 mice stained for activated microglia. FIG. 8 shows representative images from tissue from day 100 mice stained for activated astrocytes.

FIG. 9 shows area fraction quantitation of the activated astrocytes and microglial cells in the ventral horn from the cervical and lumbar regions of the spinal cord in day 85 mice. A strong trend toward astrocyte activation was observed in diseased mice (SOD1) compared to non-diseased mice (WT) in the lumbar region (FIG. 9, Panel B). Sulfasalazine treatment significantly lowered astrocyte activation in the lumbar region (FIG. 9, Panel B). Astrocyte activation was not elevated in the cervical region in SOD1 mice vs. WT mice (FIG. 9, Panel A).

In day 85 mice, increased microglial activation was observed in diseased mice (SOD1) compared to non-diseased mice (WT) in both the cervical region (FIG. 9, Panel C) and in the lumbar region (FIG. 9, Panel D), although activation in the lumbar region did not reach statistical significance. Sulfasalazine treatment significantly decreased microglial activation in the cervical region of SOD1 mice (FIG. 9, Panel C) and also reduced microglial activation in the lumbar region in SOD1 mice, although this effect did not reach statistical significance.

These results demonstrate that in day 85 SOD1 mice: (1) increased levels of neuroinflammatory cells (activated astrocytes and microglia) are present in the spinal cord before ALS-like symptomology is observed, and (2) treatment with sulfasalazine lowers the overall levels of neuroinflammatory cells (activated astrocytes and/or microglia) in both the cervical and lumbar regions of the spinal cord.

FIG. 10 shows area fraction quantitation of the activated astrocytes and microglial cells in the ventral horn from the cervical and lumbar regions of the spinal cord in day 100 mice. Significantly increased astrocyte activation was observed in diseased mice (SOD1) compared to non-diseased mice (WT) in the cervical region (FIG. 10, Panel A). Sulfasalazine treatment significantly lowered astrocyte activation in the cervical region (FIG. 10, Panel A). In the lumbar region, there was a trend towards increased astrocyte activation in the lumber region, but it was not statistically significant. Sulfasalazine treatment did not effect astrocyte activation in the lumbar region (Panel B).

At day 100, increased microglial activation was observed in diseased mice (SOD1) compared to non-diseased mice (WT) in the cervical region (FIG. 10, Panel C) and in the lumbar region (FIG. 10, Panel D), although activation in the lumbar region did not reach statistical significance. Sulfasalazine treatment resulted in a trend towards decreased microglial activation in the cervical region (FIG. 10, Panel C) and did not affect such activation in the lumbar region (FIG. 10, Panel D).

These results demonstrate that in Day 100 SOD1 mice: (1) increased levels of neuroinflammatory cells (activated astrocytes and microglia) are present in the spinal cord, in particular the cervical region, and (2) treatment with sulfasalazine lowers the overall levels of neuroinflammatory cells in the cervical region of the spinal cord.

Table 6 contains a summary of all the data from the neuroinflammation experiment presented in tabular format. The changes in area fraction staining in the cervical, thoracic, and lumbar regions of the spinal cord, as well as the combined changes across the whole spinal cord (sum of cervical, thoracic and lumbar regions) are scored for the following group comparisons:

(1) Whether increased activation of microglia and astrocytes was observed in diseased (SOD1, vehicle treated) mice vs. non-diseased (wild-type) mice (Column 4). In a total of 16 measurements, evidence for astrocyte and/or microglial activation was observed 14 times, reaching statistical significance 5 times; and (2) Whether treatment with sulfasalazine decreased activation of microglia and astrocytes compared to vehicle treatment in SOD1 mice (Column 5). From the total of 14 tissues that showed activation of astrocytes and/or microglia in SOD1 mice, sulfasalazine treatment was observed to decrease activation 8 times, reaching statistical significance 4 times.

TABLE 6

Summary of Neuroinflammation Data

| Tissue | Day | Cell type | Column 4: Increased activation in SOD1 (vehicle) vs. WT mice | Column 5: Decreased activation in sulfasalazine treated SOD1 vs. vehicle treated SOD1 mice |
| --- | --- | --- | --- | --- |
| Cervical | 85 | Astrocytes | No increase | No decrease |
| Cervical | 100 | Astrocytes | Strong increase ($p < 0.001$) | Strong decrease ($p < 0.01$) |
| Thoracic | 85 | Astrocytes | Trend | Trend |
| Thoracic | 100 | Astrocytes | Trend | No decrease |
| Lumbar | 85 | Astrocytes | Trend | Decrease ($p < 0.05$) |
| Lumbar | 100 | Astrocytes | Trend | No decrease |
| Combined | 85 | Astrocytes | Trend | Decrease ($p < 0.05$) |
| Combined | 100 | Astrocytes | Trend | Trend |
| Cervical | 85 | Microglia | Increase ($p < 0.05$) | Strong decrease ($p < 0.01$) |
| Cervical | 100 | Microglia | Increase ($p < 0.05$) | Trend |
| Thoracic | 85 | Microglia | No increase | No decrease |
| Thoracic | 100 | Microglia | Trend | No decrease |
| Lumbar | 85 | Microglia | Trend | Trend |
| Lumbar | 100 | Microglia | Trend | No decrease |
| Combined | 85 | Microglia | Increase ($p < 0.05$) | Trend |
| Combined | 100 | Microglia | Increase ($p < 0.05$) | No decrease |

This experiment establishes that sulfasalazine treatment lowers the levels of both activated microglial cells and activated astrocytes in the spinal cord.

The results from the neuroinflammatory study suggest that xCT activity is required for maximum levels of neuroinflammation to occur.

Example 4

Sulfasalazine Reaches Therapeutic Concentrations in the Spinal Cord and Spinal Cord Levels Are Proportional to Concentrations in the Plasma The experimental procedures and results provided below demonstrate the exposure and pharmacokinetics of sulfasalazine in the spinal cord and plasma of SOD1 mice.

Study Protocol and Sample Analysis

SOD1 mice were dosed with sulfasalazine at 200 mg/kg intraperitoneally and spinal cords and plasma (50 µl) harvested at indicated times (n=3 mice per time point). The zero time point was taken before drug was administered to serve as a negative control for drug quantitation. Analytical methods were developed and performed by MicroConstants (San Diego, Calif.). Spinal cords and blood plasma samples (50 µl) were homogenized in 150 µl of phosphate buffer and then extracted by a mixture of methylene chloride and MTBE (1:4 dilution). Sample extracts were analyzed and quantitated by high-performance liquid chromatography using a BetaMax Acid column maintained at 35° C. The mobile phase was nebulized using heated nitrogen in a Z-spray source/interface and the ionized compositions were detected and identified using a tandem quadrupole mass spectrometer (MS/MS).

Analytical Method Qualification

A reference standard of sulfasalazine (Sigma-Aldrich, Catalog # S0883) was used to generate a standard curve in rat plasma. The assay gave a linear response to concentrations of sulfasalazine from 10 to 20,000 ng/ml (Table 7). Dilution controls showed that samples could be diluted up to 1:100 and give a linear response in the assay. Curve fitting from this data generated the following parameters for the equation used to calculate unknown concentrations:

General Equation: $LOG(y)=A+B*LOG(x)$ where y=peak height ratio and x=concentration Specific Parameters for sulfasalazine: A=3.06, B=0.976; Correlation coefficient=1.00 the mouse spinal cord. The half-life of sulfasalazine in the spinal cord and plasma was approximately one hour, with the levels in the spinal cord proportional to the levels in the plasma. The observed half-life in the spinal cord and plasma is consistent with the reported half-life of sulfasalazine in mouse plasma, see, e.g., Zaher et al., *Mol. Pharmaceutics* 3: 55-61 (2005). Therapeutically relevant concentrations of sulfasalazine were present in the spinal cord for approximately 2-2.5 hours, corresponding to a concentration of sulfasalazine in the CNS of approximately 800-1000 ng/g. Corresponding concentrations of sulfasalazine in the plasma during this time period ranged from approximately 8,000-19,000 ng/ml.

TABLE 7

Standard Curve Values of Sulfasalazine.

| Analyte | Standard Concentrations (ng/mL) | | | | | | | | | | |
|---|---|---|---|---|---|---|---|---|---|---|---|
| | 10.0 | 20.0 | 50.0 | 100 | 250 | 500 | 1,000 | 2,000 | 5,000 | 10,000 | 20,000 |
| Sulfasalazine (measured) | 9.80  9.88 | 18.5 | 46.4 | 109 | 255 | 519 | 1,100 | 2,150 | 5,360 | 10,200 | 17,800  18,100 |
| Mean (ng/mL) | 9.84 | 18.5 | 46.4 | 109 | 255 | 519 | 1,100 | 2,150 | 5,360 | 10,200 | 18,000 |
| Percent standard deviation | −1.60 | −7.50 | −7.20 | 9.00 | 2.00 | 3.80 | 10.0 | 7.50 | 7.20 | 2.00 | −10.0 |

Separately, an internal standard (deuterated sulfasalazine) was used to determine compound extraction efficiency from mouse CNS (brain) tissue and plasma. The extraction efficiency of sulfasalazine was determined to be >98% from mouse brain tissue and plasma.

Table 8 shows the mean values for the concentrations of sulfasalazine in the spinal cord and in the plasma, and also the standard deviations (SD) of the measurements and the ratio of sulfasalazine in the spinal cord to the plasma.

TABLE 8

Mean concentrations of sulfasalazine in the CNS (spinal cord) and plasma, standard deviations (SD) and ratios in CNS (spinal cord) to plasma. BQL = below quantitative limit of detection (10 ng/ml)

| Time (min) | Spinal cord, mean (ng/g) | Spinal cord, SD (ng/g) | Plasma, mean (ng/ml) | Plasma, SD (ng/ml) | Ratio (Spinal cord/plasma) |
|---|---|---|---|---|---|
| 0 | BQL | BQL | BQL | BQL | BQL |
| 5 | 17,719 | 8,081 | 77,629 | 6,815 | 23% |
| 15 | 10,419 | 2,479 | 67,143 | 3,672 | 16% |
| 30 | 10,213 | 2,257 | 60,235 | 2,731 | 17% |
| 45 | 7,065 | 1,312 | 54,687 | 1,762 | 13% |
| 60 | 3,276 | 612 | 40,354 | 5,198 | 8% |
| 120 | 991 | 457 | 19,234 | 3,279 | 5% |
| 180 | 653 | 119 | 6,090 | 994 | 11% |
| 240 | 20 | 18 | 2,580 | 622 | 1% |
| 360 | BQL | BQL | 630 | 121 | n/a |

FIG. 11 shows the mean logarithmic concentration of sulfasalazine in the spinal cord versus time following administration. Sulfasalazine showed immediate penetration into the spinal cord, reaching levels of approximately 18 μg/gram of tissue within 5 minutes of drug administration. The levels in the spinal cord ranged from approximately 5-17% of the levels in the plasma over the next three hours. The minimum therapeutic range of sulfasalazine, estimated to be 2 to 2.5 micromolar (equivalent to 800-1,000 ng/ml; assuming a conversion of 1 gram tissue=1 ml volume), is shown in the shaded rectangle in the figure. These results show that sulfasalazine reached immediate and therapeutic levels in Results of the SOD1 experiments provide strong support that sulfasalazine has therapeutic applications for ALS, despite the short half-life of sulfasalazine and resulting sub-optimal drug coverage in these particular studies. Levels of the target-xCT-were elevated in diseased tissue and escalated with disease progression. Treatment with sulfasalazine demonstrated significant efficacy in two important components of disease: (1) survival after onset of neurological disease and, (2) attenuation of neuroinflammation.

Example 5

Determination of Solubility of Crystalline Compound at Different pH

The following procedure was used to determine the effect of pH on the solubility of sulfasalazine in aqueous solutions. A 1.8 mg sample of sulfasalazine was placed in a microcentrifuge tube. A 0.9 mL of 0.01N HCl was then added to the tube, which was capped and mixed using a vortex mixer for 1 minute. The sample in the tube was then centrifuged at 15,800 relative centrifugal force (RCF) for 1 minute. A 50 μL sample of the liquid was diluted into 250 μL HPLC solvent, and the tube was capped and vortexed for 20 seconds and allowed to stand undisturbed at 37° C. until the next sample was collected. After 30 minutes, a 0.9 mL portion of buffer solution (at twice the concentration of buffer salts) was added to the microcentrifuge tube, and the procedure repeated as described above. Samples were collected at predetermined time intervals and analyzed by HPLC. The solubility of sulfasalazine as a function of pH was then determined, as shown in FIG. 12. This data indicates that crystalline drug alone may have good bioavailability based on solubility if the pH of the absorption window is high (pH 6 or above). This data also indicates that crystalline drug alone may have poor bioavailability based on solubility if the pH of the absorption window is low (below pH 6).

Example 6

Reformulation of Sulfasalazine to Increase Oral Bioavailability

Novel formulations of sulfasalazine that increase the solubility of sulfasalazine at enteric pH (i.e., below pH 6) were prepared, including a formulation of sulfasalazine that increases the oral bioavailability of the sulfasalazine by at least three-fold in a rat model.

Preparation of Sulfasalazine Formulations

Sulfasalazine Formulation Exemplar 1: 25% Sulfasalazine: 75% HPMCAS SDD

A spray dried dispersion (SDD) of 25 wt % sulfasalazine and 75 wt % HPMCAS (hereafter "25% sulfasalazine: HPMCAS") was prepared using a spray drying process as follows. A spray solution was prepared by dissolving 100 mg sulfasalazine and 300 mg HPMCAS (Hydroxypropylmethylcellulose acetate succinate; AQOAT M grade, Shin Etsu, Tokyo, Japan) in 19.6 gm of solvent (95/5 w/w tetrahydrofuran/water), to form a spray solution containing 2 wt % solids. This solution was spray dried using a small-scale spray-dryer, which consisted of an atomizer in the top cap of a vertically oriented 11-cm diameter stainless steel pipe. The atomizer was a two-fluid nozzle, where the atomizing gas was nitrogen delivered to the nozzle at 70° C. at a flow rate of 31 standard L/min (SLPM), and the solution to be spray dried was delivered to the nozzle at room temperature at a flow rate of 1.3 mL/min using a syringe pump. The outlet temperature of the drying gas and evaporated solvent was 31.5° C. Filter paper with a supporting screen was clamped to the bottom end of the pipe to collect the solid spray-dried material and allow the nitrogen and evaporated solvent to escape. The resulting spray dried powder was dried under vacuum overnight, with a yield of 89%.

Sulfasalazine Formulation Exemplar 2: 25% Sulfasalazine: 75% PVP VA64 SDD

A spray dried dispersion (SDD) of 25 wt % sulfasalazine and 75 wt % PVP VA64 (hereafter "25% sulfasalazine:PVP VA64") was prepared using a spray drying process as follows. The procedure of sulfasalazine formulation Exemplar 1 was repeated except that the polymer was vinylpyrrolidone-vinyl acetate copolymer (PVP VA64, purchased from BASF as Kollidon® VA 64, Ludwigshafen, Germany). The spray drying conditions were the same as sulfasalazine formulation Exemplar 1. The resulting spray dried powder was dried under vacuum overnight, with a yield of 95.7%.

Sulfasalazine Formulation Exemplar 3: 50% Sulfasalazine: 50% PVP VA64 SDD

A spray dried dispersion (SDD) of 50 wt % sulfasalazine and 50 wt % PVP VA64 (hereafter "50% sulfasalazine:PVP VA64") was prepared using a spray drying process as follows. A spray solution was prepared by dissolving 200 mg sulfasalazine and 200 mg PVP VA64 in 19.6 gm of solvent (90/10 w/w tetrahydrofuran/water), to form a spray solution containing 2 wt % solids. This solution was spray dried using a small-scale spray-dryer, as described in sulfasalazine formulation Exemplar 1. The resulting spray dried powder was dried under vacuum overnight, with a yield of 95.7%.

Example 7

Characterization of the Compositions Showing Amorphous Dispersion Using PXRD Analysis The three exemplar formulations were analyzed by powder X-ray diffraction (PXRD) using an AXS D8 Advance PXRD measuring device (Bruker, Inc. of Madison, Wis.) using the following procedure. Samples (approximately 100 mg) were packed in Lucite sample cups fitted with Si(511) plates as the bottom of the cup to give no background signal. Samples were spun in the φ plane at a rate of 30 rpm to minimize crystal orientation effects. The X-ray source (KCu$_\alpha$, λ=1.54 Å) was operated at a voltage of 45 kV and a current of 40 mA. Data for each sample were collected over a period of 30 minutes in continuous detector scan mode at a scan speed of 2 seconds/step and a step size of 0.04°/step. Diffractograms were collected over the 2θ range of 4° to 40°. FIG. 13 shows the diffraction pattern of the formulations, revealing an amorphous halo, indicating the sulfasalazine in each of the exemplar formulations was essentially amorphous.

Example 8

Characterization of Compositions Showing Homogeneity Using mDSC Analysis

The exemplar formulations were analyzed using modulated differential scanning calorimetry (mDSC) as follows. Samples of the formulations (about 2 to 4 mg) were equilibrated at <5% RH overnight in an environmental chamber at ambient temperature. The samples were then loaded into pans and sealed inside the environmental chamber. The samples were then analyzed on a Q1000 mDSC (TA Instruments, New Castle, Del.). Samples were scanned over the temperature range of −40° C. to 200° C., at a scan rate of 2.5° C./min, and a modulation rate of ±1.5° C./min. The glass-transition temperature (Tg) was calculated based on half height. The mDSC results are shown in FIG. 14, and the Tg is also reported in Table 9 (data are reported as an average of 3 replicates). In all cases, the dispersions exhibited a single Tg, indicating the active agent in the dispersion was molecularly dispersed and homogeneous in the SDD.

TABLE 9

Glass transition temperatures of sulfasalazine preparations

| Sample | Tg at <5% RH (° C.) |
| --- | --- |
| Formulation Exemplar 1<br>25% Sulfasalazine:HPMCAS SDD | 98.1 ± 0.3 |
| Formulation Exemplar 2<br>25% Sulfasalazine:PVP VA64 SDD | 110.5 ± 0.03 |
| Formulation Exemplar 3<br>50% Sulfasalazine:PVP VA64 SDD | 118.0 ± 0.2 |

Example 9

Determination of Solubility of Reformulated Compounds at Enteric pH

The release of sulfasalazine from the dispersions of formulation exemplars 1-3, crystalline sulfasalazine, and amorphous sulfasalazine formulation (made by spray drying) was determined using the following procedures. A sample mass of 4.5 mg of the test material was placed in a microcentrifuge tube. To this was added 0.9 mL of gastric buffer (GB) solution (0.01 N HCl, pH 2). The tubes were vortexed for one minute, then centrifuged for one minute before taking each sample. Samples (the liquid phase) were taken at 5, 15, and 25 minutes. At 30 minutes after the start of the test, 0.9 mL of intestinal buffer (IB) solution (a phosphate/citrate buffer at pH 5.5) was added to the tubes (at a double concentration of the buffer salts to result in the desired pH level and buffer strength). The tubes were vortexed for one minute, then centrifuged for one minute before taking each sample. Samples were taken at 4, 10, 20, 40, 90 and 1200 minutes after addition of the intestinal buffer solution. The concentration of sulfasalazine was determined by HPLC as previously described. Table 10 shows the data from the solubility experiment and FIG. 15 shows the data in graphical format. This data demonstrated that the amorphous sulfasalazine preparation has higher solubility than the crystalline sulfasalazine, by approximately 36%. When the amorphous sulfasalazine was prepared with polymers, the solubility further increased. The 25% sulfasalazine:HPMCAS-MG formulation had an increase in solubility of approximately 200% compared to the crystalline sulfasalazine and of approximately 46% over the amorphous sulfasalazine. The 50% sulfasalazine:PVP VA64 polymer had an increase in solubility of approximately 508% compared to the crystalline sulfasalazine and of approximately 372% over the amorphous sulfasalazine. The 25% sulfasalazine:PVP VA64 polymer had an increase in solubility of approximately 883% compared to the crystalline sulfasalazine and of approximately 647% over the amorphous sulfasalazine.

mixing in a mortar and pestle until the composition were evenly resuspended to form the non-reformulated composition. Separately, a sample of 25% sulfasalazine:PVP VA64 SDD (Formulation Exemplar 2) was resuspended in 0.5% Methocel to a concentration of 40 mg/ml sulfasalazine per ml. The 25% sulfasalazine:PVP VA64 SDD composition was re-suspended by adding the 0.5% Methocel drop-wise to the composition and mixing in a mortar and pestle until the composition were evenly resuspended, forming the reformulated composition.

Animal Study Design, Dosing and Plasma Collection:

A total of 6 Sprague-Dawley rats were used in the study, divided into 2 cohorts as shown in Table 10. All rats were males that ranged in weight from 202 grams to 214 grams apiece. Rats were allowed to eat ad libitum before testing. Independently, the crystalline sulfasalazine formulation and the reformulated 25% sulfasalazine:75% PVP VA64 SDD composition were administered by gastric lavage at a dose of 400 mg/kg. Following drug administration, 200 µl of plasma was collected from each animal at the following time points:

TABLE 10

Solubility of Compounds in Gastric Buffer and Intestinal Buffer

| Sample | Cmax GB (ug/mL) | Cmax IB (ug/mL) | Cmax IB (ug/mL) at 90 min | Cmax IB (ug/mL) at 1200 min | AUC (min*ug/mL) | Ratio of AUC to cystalline sulfasalazine | Ratio of AUC to amorphous sulfasalazine |
|---|---|---|---|---|---|---|---|
| Crystalline sulfasalazine | 15 | 282 | 271 | 282 | 22,200 | 100.0% | 73.3% |
| Amorphous sulfasalazine | 154 | 372 | 372 | 367 | 30,300 | 136.5% | 100.0% |
| 25% sulfasalazine:HPMCAS-MG | 34 | 725 | 571 | 725 | 44,400 | 200.0% | 146.5% |
| 50% sulfasalazine:PVP VA64 | 67 | 1,372 | 1,232 | 1,073 | 112,800 | 508.1% | 372.3% |
| 25% sulfasalazine:PVP VA64 | 425 | 2,350 | 2,319 | 2,290 | 196,200 | 883.8% | 647.5% |

Example 10

Reformulation of Sulfasalazine Increases Oral Bioavailability In Vivo

The following experiments demonstrate that administration of a 25% sulfasalazine:PVP VA64 SDD composition results in a significant increase in oral bioavailability compared to administration of crystalline sulfasalazine in a rat model. Preparation of Compounds Crystalline sulfasalazine was obtained from Sigma-Aldrich (St. Louis, Mo.), Catalog # S0883. Crystalline sulfasalazine was re-suspended in 0.5% Methocel (Methocel A4M Premium, Dow Chemical, Midland, Mich.) to a concentration of 40 mg/ml sulfasalazine. Re-suspension of the crystalline sulfasalazine composition was accomplished by adding the 0.5% Methocel drop-wise to the composition and 30, 60, 90, 120, 160 and 240 minutes. Plasma samples were snap frozen in liquid $N_2$ and stored at −80° C. until analysis.

Levels of sulfasalazine detected in the rat plasma at the different time points are given in Table 11, the summary and statistical values are given in Table 12 and the data presented in graphical format in FIG. 16. One rat (#6326) showed evidence that drug was partially administered to the lungs, resulting in high plasma levels, and values from this rat were not included in calculating mean values or in the statistical analysis. Oral administration of sulfasalazine, both the crystalline and the 25% sulfasalazine:PVP VA64 SDD formulation showed immediate plasma accumulation within the first 30 minutes of administration. The reformulated sulfasalazine (25% sulfasalazine:PVP VA64 SDD) showed higher plasma levels, ranging from approximately 300% at the first 30 minute time point to about 160% at the 3 hour time point, when compared to the crystalline sulfasalazine composition following oral administration.

TABLE 11

Concentrations of sulfasalazine in plasma.

Analyte
Sulfasalazine Levels, Plasma (ng/ml)
Treatment

| | | Reformulation (25% GLX-1112:PVP-VA64 SDD) | | | | Parent (Crystalline) | | | |
|---|---|---|---|---|---|---|---|---|---|
| | | Subject ID | | | | | | | |
| | | 6326* | 6327 | 6328 | Mean Levels | 6329 | 6330 | 6331 | Mean Levels |
| Time Points | 0.5 h | 23,200 | 4,760 | 4,370 | 4,565 | 1,390 | 1,270 | 1,800 | 1,487 |
| | 1 h | 27,400 | 3,020 | 3,080 | 3,050 | 1,050 | 1,380 | 991 | 1,140 |
| | 1.5 h | 17,100 | 2,980 | 2,910 | 2,945 | 1,340 | 1,810 | 1,130 | 1,427 |

TABLE 11-continued

Concentrations of sulfasalazine in plasma.

Analyte
Sulfasalazine Levels, Plasma (ng/ml)
Treatment

| | | Reformulation (25% GLX-1112:PVP-VA64 SDD) | | | | Parent (Crystalline) | | |
|---|---|---|---|---|---|---|---|---|
| | | | | | Subject ID | | | |
| | 6326* | 6327 | 6328 | Mean Levels | 6329 | 6330 | 6331 | Mean Levels |
| 2 h | 10,400 | 2,720 | 2,660 | 2,690 | 1,050 | 1,380 | 1,340 | 1,257 |
| 3 h | 7,130 | 1,520 | 1,780 | 1,650 | 939 | 787 | 1,360 | 1,029 |
| 4 h | 3,790 | 271 | 1,050 | 661 | 872 | 790 | 887 | 850 |

*Test animal exhibited evidence that drug was partialty administered to lung; values for this animal were ommitted from mean value calculation.

TABLE 12

Summary and statistics of bioavailability experiment.
All statistics were calculated using two-tailed Students t-test.

| Time Points | Refomulation (25% GLX-1112:PVP-VA64 SDD) Mean Values | Parent (Crystalline) Mean Values | Percent difference: Reformulated/Parent | p-value |
|---|---|---|---|---|
| 0.5 h | 4,565 | 1,487 | 307% | 0.0012 |
| 1 h | 3,050 | 1,140 | 267% | 0.0012 |
| 1.5 h | 2,945 | 1,427 | 206% | 0.0100 |
| 2 h | 2,690 | 1,257 | 214% | 0.0018 |
| 3 h | 1,650 | 1,029 | 160% | 0.0820 |
| 4 h | 661 | 850 | 78% | 0.7755 |

FIG. 16 shows the mean values of plasma sulfasalazine plotted in graphical format.

The results of the above experiments demonstrate that: (1) the reformulated sulfasalazine attains higher plasma concentrations following oral administration than the crystalline formulation of sulfasalazine and that (2) the increase in plasma concentrations are approximately 300% percent to 160% over the first 3 hours of administration. These results demonstrate that sulfasalazine can be reformulated to increase oral bioavailability.

While a number of exemplary embodiments, aspects and variations have been provided herein, those of skill in the art will recognize certain modifications, permutations, additions and combinations and certain sub-combinations of the embodiments, aspects and variations. It is intended that the following claims are interpreted to include all such modifications, permutations, additions and combinations and certain sub-combinations of the embodiments, aspects and variations are within their scope.

The entire disclosure of all documents cited throughout this application are incorporated herein by reference. All ranges set forth in this specification include the endpoints provided in those ranges unless clearly indicated otherwise.

REFERENCES

1. Compton A., et al, 2008. Multiple sclerosis. *Lancet* 372:1502-1517.
2. Trapp, B. et al. (2008). Multiple sclerosis: an immune or neurodegenerative disorder? *Annu. Rev. Neurosci.* 31:247-269.
3. Kremenchutsky M., et al. (2006). The natural history of multiple sclerosis: a geographically based study 9: Observations on the progressive phase of the disease. Brain 129:584-594.
4. Lassmann H., et al. (2012). Progressive multiple sclerosis: pathology and pathogenesis. *Nat. Rev. Neurology* 8:647-656.
5. Stys P., et al. (2012). Will the real multiple sclerosis please stand up? *Nat. Rev. Neuroscience* 13:507-514.
6. Fox, R., et al. 2012. Setting a research agenda for progressive multiple sclerosis: the International Collaborative on Progressive Miss. *Multiple Sclerosis Journal* 18:1534-1540.
7. Fitzner, D., et al. Chronic progressive multiple sclerosis—pathogenesis of neurodegeneration and therapeutic strategies. *Curr. Neuropharmacology* 8:305-315 (2008).
8. Weiner, H. 2008. A shift from adaptive to innate immunity: a potential mechanism of disease progression in multiple sclerosis. *J. Neurology* 255, Suppl. 1:3-11.
9. Burns S., et al. 2012. Mitoxantrone repression of astrocyte activation: Relevance to multiple sclerosis. *Brain Res.* 1473: 236-241.
10. Frigo, M. 2012. Glutamate and Multiple Sclerosis. *Curr. Medicin. Chem.* 19:1295-1299.
11. Matute, 2011. Glutamate and ATP signaling in white matter pathology. *J. Anatomy* 219:53-64.
12. Sarchielli, P. et al. 2003. Excitatory amino acids and multiple sclerosis: Evidence from cerebrospinal fluid. *Arch. Neurol.* 60:1082-1088.
13. Eriksson, M., et al. 2002. Epileptic seizures, cranial neuralgias and paroxysmal symptoms in remitting and progressive multiple sclerosis. *Mult. Scler.* 8:495-499.
14. Svendsen, K., et al. 2004. Sensory function and quality of life in patients with multiple sclerosis and pain. *Pain* 114: 473-481.
15. Bogaert, E., et al. 2010. Amyotrophic lateral sclerosis and excitotoxicity: from pathological mechanism to therapeutic target. *CNS Neurol. Disord. Drug Targets* 9:297-304.
16. Philips. T., et al. 2011. Neuroinflammation in amyotrophic lateral sclerosis: role of glial activation in motor neuron disease. *Lancet Neurol.* 10:253-263.
17. Ilieva, H., et al. 2009. Non-cell autonomous toxicity in neurodegenerative disorders: ALS and beyond. *J. Cell Biol.* 187: 761-772.
18. Lin, L., et al. 2010. The interaction of the neuroprotective compounds riluzole and phenobarbital with AMPA-type glutamate receptors: a patch-clamp study. *Pharmacology.* 85:54-62.
19. Baron, R., et al. 2010. Neuropathic pain: diagnosis, pathophysiological mechanisms, and treatment. Lancet Neurology 9: 807-819.
20. Berti-Mattera, L., et al. 2008. Sulfasalazine Blocks the Development of Tactile Allodynia in Diabetic Rats. *Diabetes* 57: 2801-2808.

21. Ungard, R., et al. 2014. Inhibition of breast cancer-cell glutamate release with sulfasalazine limits cancer-induced bone pain. *Pain* 155: 28-36.
22. Weaver, A., et al. 1999. Improved gastrointestinal tolerance and patient preference of enteric-coated sulfasalazine versus uncoated sulfasalazine tablets in patients with rheumatoid arthritis. *J. Clin. Rheumatol.* 5: 193-200.
23. Peppercorn, M. 1987. Sulfasalazine and related new drugs. *J Clin Pharmacol.* 27: 260-265.
24. Watkinson, G. 1986. Sulphasalazine: a review of 40 years' experience. *Drugs.* 32: Suppl 1:1-11.
25. Noseworthy, J., et al. 1998. The Mayo clinic-Canadian cooperative trial of sulfasalazine in active multiple sclerosis. *Neurology* 15: 1342-1352.
26. Khan, A., et al. 1980. Optimum dose of sulfasalazine for maintenance treatment in ulcerative colitis. *Gut* 21:232-240.
27. Yamasaki, Y., et al. 2007. Pharmacogenetic characterization of sulfasalazine disposition based on NAT2 and ABCG2 (Bcrp) gene polymorphisms in humans. *Clin. Pharmac. Therap.* 84: 95-103.
28. de Jong, F., et al. 2004. ABCG2 Pharmacogenetics: Ethnic differences in allele frequency and assessment of influence on irinotecan disposition. *Clin. Cancer Res.* 10:5889-5894.
29. Buckingham, S., et al. 2011. Glutamate release by primary brain tumors induces epileptic activity. *Nat Med.* 17:1269-1274.
30. Gurney M, et al. 1994. Motor neuron degeneration in mice that express a human Cu/Zn superoxide dismutase mutation. *Science* 264: 1772-1775.
31. Scott S, et al. 2008. Design, power, and interpretation of studies in the standard murine model of ALS. *Amyotroph Lateral Scler* 9: 4-15.
32. Shin, J., et al. 2012. Concurrent blockade of free radical and microsomal prostaglandin E synthase-1-mediated PGE(2) production improves safety and efficacy in a mouse model of amyotrophic lateral sclerosis. *J. Neurochem.* 122: 952-961.
33. Lincecum, J., et al. 2010. From transcriptome analysis to therapeutic anti-CD40L treatment in the SOD1 model of amyotrophic lateral sclerosis. *Nat. Genetics* 42: 392-411.
34. Zaher, H., et al. 2005. Breast cancer resistance protein (Bcrp/abcg2) is a major determinant of sulfasalazine absorption and elimination in the mouse. *Mol. Pharmaceutics* 3: 55-61.

What is claimed is:

1. A method for treating a patient with a neurodegenerative disorder wherein the disorder is selected from the group consisting of tuberous sclerosis and epilepsy, the method comprising orally administering to the patient a pharmaceutical composition comprising a solid dispersion of sulfasalazine in essentially amorphous form and PVP VA64, wherein the ratio of sulfasalazine to PVP VA64 is between 20:80 wt./wt. and 30:70 wt./wt.

2. The method of claim 1, wherein the solid dispersion is a spray-dried dispersion.

3. The method of claim 1, wherein the ratio of sulfasalazine to PVP VA64 is 25:75 wt./wt.

4. The method of claim 1, wherein the neurodegenerative disorder is tuberous sclerosis.

5. The method of claim 1, wherein the neurodegenerative disorder is epilepsy.

6. A method for treating a patient with tuberous sclerosis, the method comprising orally administering to the patient a pharmaceutical composition comprising a solid dispersion of sulfasalazine in essentially amorphous form and PVP VA64, wherein the ratio of sulfasalazine to PVP VA64 is between 20:80 wt./wt. and 30:70 wt./wt.

7. The method of claim 6, wherein the solid dispersion is a spray-dried dispersion.

8. The method of claim 6, wherein the ratio of sulfasalazine to PVP VA64 is 25:75 wt./wt.

9. A method for treating a patient with epilepsy, the method comprising orally administering to the patient a pharmaceutical composition comprising a solid dispersion of sulfasalazine in essentially amorphous form and PVP VA64, wherein the ratio of sulfasalazine to PVP VA64 is between 20:80 wt./wt. and 30:70 wt./wt.

10. The method of claim 9, wherein the solid dispersion is a spray-dried dispersion.

11. The method of claim 9, wherein the ratio of sulfasalazine to PVP VA64 is 25:75 wt./wt.

* * * * *